US009713632B2

(12) United States Patent
Van Der Weerden et al.

(10) Patent No.: US 9,713,632 B2
(45) Date of Patent: Jul. 25, 2017

(54) METHOD OF TREATMENT

(71) Applicant: Hexima Limited, Bundoora (AU)

(72) Inventors: Nicole Louise Van Der Weerden, Coburg (AU); Marilyn Anne Anderson, Keilor (AU)

(73) Assignee: Hexima Limited, Bundoora (AU)

( * ) Notice: Subject to any disclaimer, the term of this patent is extended or adjusted under 35 U.S.C. 154(b) by 27 days.

(21) Appl. No.: 14/726,400

(22) Filed: May 29, 2015

(65) Prior Publication Data

US 2016/0106807 A1 Apr. 21, 2016

Related U.S. Application Data

(60) Provisional application No. 62/066,808, filed on Oct. 21, 2014.

(51) Int. Cl.
*A61K 38/16* (2006.01)
*A61K 45/06* (2006.01)
*A61K 9/00* (2006.01)

(52) U.S. Cl.
CPC .......... *A61K 38/168* (2013.01); *A61K 9/0014* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,298,368 A | 1/1967 | Charos | |
| 4,087,675 A | 5/1978 | Sansonetti | |
| 4,267,852 A | 5/1981 | Hullinger | |
| 4,331,137 A | 5/1982 | Sarui | |
| 5,098,415 A | 3/1992 | Levin | |
| 5,156,591 A | 10/1992 | Gross et al. | |
| 5,181,914 A | 1/1993 | Zook | |
| 5,449,658 A | 9/1995 | Unhoch et al. | |
| 5,668,084 A | 9/1997 | Unhoch et al. | |
| 5,696,164 A | 12/1997 | Sun et al. | |
| 5,795,314 A | 8/1998 | Berenstein | |
| 6,231,875 B1 | 5/2001 | Sun et al. | |
| 6,245,347 B1 | 6/2001 | Zhang et al. | |
| 6,281,239 B1 | 8/2001 | Glassman | |
| 6,391,879 B1 | 5/2002 | Reeves | |
| 6,465,709 B1 | 10/2002 | Sun et al. | |
| 6,477,410 B1 | 11/2002 | Henley et al. | |
| 6,528,697 B1 | 3/2003 | Knutson et al. | |
| 6,585,963 B1 | 7/2003 | Quan et al. | |
| 6,634,367 B2 | 10/2003 | Abraham et al. | |
| 6,641,601 B1 | 11/2003 | Augustine et al. | |
| 6,727,401 B1 | 4/2004 | Venkateshwaran et al. | |
| 6,735,470 B2 | 5/2004 | Henley et al. | |
| 6,821,508 B2 | 11/2004 | Zatz et al. | |
| 6,846,837 B2 | 1/2005 | Maibach et al. | |
| 6,881,418 B2 | 4/2005 | Morita et al. | |
| 6,911,577 B2 * | 6/2005 | Simmons ............. | C07K 14/415 424/93.2 |
| 6,921,529 B2 | 7/2005 | Maley | |
| 2002/0007191 A1 | 1/2002 | Feldman | |
| 2003/0144625 A1 | 7/2003 | Sherman et al. | |
| 2004/0096410 A1 | 5/2004 | Maley et al. | |
| 2004/0161452 A1 | 8/2004 | Petit | |
| 2005/0038375 A1 | 2/2005 | Nitzan et al. | |
| 2005/0261755 A1 | 11/2005 | Bacino et al. | |
| 2006/0013862 A1 | 1/2006 | Held | |
| 2006/0052739 A1 | 3/2006 | Henley et al. | |
| 2006/0234981 A1 | 10/2006 | Baker et al. | |
| 2007/0027481 A1 | 2/2007 | Weinfield | |
| 2007/0049998 A1 | 3/2007 | Conrad et al. | |
| 2007/0104664 A1 | 5/2007 | Maltezos et al. | |
| 2007/0155699 A1 | 7/2007 | Baker et al. | |
| 2007/0265226 A1 | 11/2007 | Lee et al. | |
| 2007/0292355 A1 | 12/2007 | Tamarkin et al. | |
| 2008/0312579 A1 | 12/2008 | Chang et al. | |
| 2009/0048590 A1 | 2/2009 | Conrad et al. | |

FOREIGN PATENT DOCUMENTS

| | | |
|---|---|---|
| EP | 2664327 | 11/2013 |
| WO | PCT/US2009/004361 | 7/2009 |
| WO | PCT/US2009/004361 | 1/2010 |

OTHER PUBLICATIONS

Hay et al., "The topical treatment of onychomycosis using a new combined urea/imidazole preparation", Clinical Experimental Dermatology, 1988, pp. 164-167.*
Ashburn, M.A., et al. The pharmacokinetics of transdermal fentanyl delivered with and without controlled heat. The Journal of Pain 4(6): 291-297 (Aug. 2003).
Ausubel, F.M., et al. Current protocols in molecular biology, Supplement 46, Unit 19.3 Informatics. John Wiley & Sons: 19.3.1-19.3.29 (1999).
Baran, R., et al. Textbook of Cosmetic Dermatology: 58 (2004).
U.S. Appl. No. 60/730,545, filed Jul. 26, 2005, Maltezos, et al.
U.S. Appl. No. 62/066,808, filed Oct. 21, 2014, Van Der Weerden et al.
Bloch, C. A new family of small (5 kDa) protein inhibitors of insect α-amylases from seeds or sorghum (*Sorghum bicolor* (L) *Moench*) have sequence homologies with wheat γ-purothionins. Federation of European Biochemical Societies 279(1): 101-104 (Feb. 1991).
Botek, G. Fungal nail infection: assessing the new treatment options. Cleveland Clinic Journal of Medicine 70(2): 110-114 (2003).

(Continued)

*Primary Examiner* — Lianko Garyu

(57) ABSTRACT

The present disclosure relates to the control of fungal infection of horn-like envelopes covering dorsal and terminal phalanges in humans and animals and related cerebral protrusions in animals as well as keratin comprising material on surfaces of humans and animals. Agents and natural and synthetic formulations and extracts useful for the control of fungal infection of these envelopes and related protrusions and keratin comprising material are also encompassed by the subject disclosure. In an embodiment, the present disclosure teaches the treatment of fungal infection of nails and in particular onychomycosis in humans.

10 Claims, 22 Drawing Sheets

(56) References Cited

OTHER PUBLICATIONS

Boukes, R. J., et al. Analysis of human tear protein profiles using high performance liquid chromatography (HPLC). Doc Ophthalmol 67(1-2): 105-113 (Sep.-Oct. 1987).

Broekaert, W.F., et al. An automated quantitative assay for fungal growth inhibition. FEMS Microbiology Letters 69: 55-60 (1990).

Burge, H. How does heat affect fungi? The Environmental Reporter 4(3) (Mar. 2006).

Cabral, K.M.S., et al. Production of the active antifungal Pisum sativum defensin 1 (Psd1) in Pichia pastoris: overcoming the inefficiency of the STE13 protease. Protein Expression and Purification 31: 115-122 (2003).

Chato, J., Electrical Engineer. An oral history conducted in 2000 by Frederik Nebeker. IEEE History Center, Rutgers University, New Brunswick, N.J.

Chato, J.C. Thermal therapy of toe nail fungus. Advances in Heat and Mass Transfer in Biotechnology: 139-140 (Nov. 2000).

Colilla, F.J., et al. γ-Purothionins: amino acid sequence of two polypeptides of a new family of thionins from wheat endosperm. Federation of European Biochemical Societies 270(1,2): 191-194 (Sep. 1990).

Elewski, B.E., et al. Fungal diseases, chap 77. Dermatology $3^{rd}$ ed. Elsevier Saunders, Philadelphia (2012).

Fisher, B.D., et al. Invasive aspergillosis: progress in early diagnosis and treatment. American Journal of Medicine 71: 571-577 (Oct. 1981).

Goddard, D.R., et al. A study on keratin. Journal of Biogical. Chemistry 106: 605-614 (1934).

Gomes, M.Z.R., et al. Mucormycosis caused by unusual mucormycetes, non-rhizopus, -mucor, and -lichtheimia species. Clinical Microbiology Reviews 24(2): 411-445 (Apr. 2011).

Gupchup-Malhotra, G., et al. Characterization of the physical factors affecting nail permeation using water as a probe. Journal of Cosmetic Science 51(6): 367-377 (2000).

Hayes, B.M.E., et al. Identification and mechanism of action of the plant defensin NaD1 as a new member of the antifungal drug arsenal against candida albicans. Antimicrobial Agents and Chemotherapy 57(8): 3667-3675 (Aug. 2013).

Hayes, B.M., et al. Activation of stress signaling pathways enhances tolerance of fungi to chemical fungicides and antifungal proteins, Cellular and Molecular Life Sciences 71(14): 2651-2666 (2014).

Hui, X., et al. Enhanced human nail drug delivery: nail inner drug content assayed by new unique method. Journal of Pharmaceutical Sciences 91(1): 189-195 (Jan. 2002).

Hull, W. Heat-enhanced transdermal drug delivery: a survey paper. The Journal of Applied Research 2(1) (Winter 2002).

Jaffe, R. Onychomycosis. Arch Fam Med 7: 587-592 (1988).

Janssen, B.J.C., et al. Structure of petunia hybrid defensin 1, a novel plant defensin with five disulfide bonds. Biochemistry 42(27): 8214-8222 (2003).

Johnson, M.E., and Kahn, M., Peptide turn mimetics, Biotechnology and Pharmacy, Pezzuto et al., Eds., Chapman and Hall:New York, 1993, pp. 366-378.

Kent, W.J. BLAT—the BLAST-like alignment tool. Genome Research 12: 656-664 (2002) (downloaded from genome.cshlp.org on May 31, 2015—Published by Cold Spring Harbor Laboratory Press).

Khengar, R.H., et al. Nail swelling as a pre-formulation screen for the selection and optimisation of ungual penetration enhancers. Pharmaceutical Research 24(12): 2207-2212 (2007).

Kobayashi, Y., et al. Drug permeation through the three layers of the human nail plate. Journal of Pharmacy and Pharmacology Sciences 51(3): 271-278 (Mar. 1999).

Kobayashi, Y., et al. In vitro permeation of several drugs through the human nail plate: relationship between physicochemical properties and nail permeability of drugs. European Journal of Pharmaceutical Sciences 21: 471-477 (2004).

Lamberg, S.I. Blackwell's primary care essentials. Dermatology, $2^{nd}$ Edition (2002).

Langmead, B., et al. Ultrafast and memory-efficient alignment of short DNA sequences to the human genome. Genome Biology 10R25: 1-10 (2009).

Leeming, M.N., et al. Low voltage, direct-current burns. JAMA 214(9): 1681-1684 (Nov. 1970).

Li, H, et al. Fast and accurate long-read alignment with Burrows-Wheeler transform. Bioinformatics 26(5): 589-595 (2010).

Malhotra, G.G. Investigation of nail permeation enhancement by chimcal modification using water as a probe. Journal of Pharmaceutical Sciences 91(2): 312-323 (Feb. 2002).

Mertin, D., and Lippold, B.C. In vitro permeability of the human nail and of a keratin membrane from bovine hooves: prediction of the penetration rate of antimycotics through the nail plate and their efficacy. Journal of Pharmacology and Pharmacotherapeutics 49: 866-872 (1997).

Mitchell, T.G., and Perfect, J.R. Cryptococcosis in the era of AIDS—100 years after the discovery of cryptococcus neoformans. Clinical Microbiology Reviews 8(4): 515-548 (Oct. 1995).

Moritz, A.R., et al. Studies of thermal injury II: the relative importance of time and surface temperature in the causation of cutaneous burn. American Journal of Pathology 23: 695-720 (1947).

Murdan, S. Drug delivery to the nail following topical application. International Journal of Pharmaceutics 236(1-2): 1-26 (Apr. 2002).

Murdan, S. Enhancing the nail permeability of topically applied drugs. Expert Opinion on Drug Delivery 5(11): 1267-1282 (2008).

Murthy, S.N., et al. TransScreen-N: method for rapid screening of trans-ungual drug delivery enhancers. Journal of Pharmaceutical Sciences 98(11): 4264-4271 (Nov. 2002).

Nair, A.B., et al. A study on the effect of inorganic salts in transungual drug delivery of terbinafine. Journal of Pharmacy and Pharmacology 61(4): 431-437 (2009).

Patterson, T.F., et al. Invasive aspergillosis: disease spectrum, treatment practices, and outcomes. Medicine 79(4): 250-260 (2000).

Querinjean, P., et al. Molecular weight single-chain structure and amino acid compostion of human lactoferrin. European Journal of Biochemistry 20(3): 420-425 (Jun. 1971).

Quintanar-Guerrero et al. The effect of keratolytic agents on the permeability of three imlazole antimycotic drugs through the human nail. Drug Development and Industrial Pharmacy 24(7): 685-690 (1998).

Reid, G., et al. Microbiota restoration: natural and supplemented recovery of human microbial communities. Nature Reviews Microbiology 9: 27-38 (Jan. 2011).

Reinauer, S. et al., Iontophoresis with alternating current and direct current offset (AC/DC iontophoresis): a new approach for the treatment of hyperhidrosis. British Journal of Dermatology 129(2): 166-169 (Aug. 1993).

Richer, D.L. Synergism—a patent view. Pesticide Science 19: 309-315 (1987).

Roberts, D.F., et al. A possible climatic effect on nail growth. Journal of Applied Physiology 13: 135-138 (1958).

Robbins, C.R. Chemical and Physical Behavior of Human Hair 4th Ed., 2004, p. 238.

Rogers, P., and Bassler, M. Treating onychomycosis. American Family Physician 63(4): 663-672 (Feb. 2001).

Sagaram, U.S., et al. Structure-activity determinants in antifungal plant defensins MsDef1 and MtDef4 with different modes of action against fusarium graminearum. PLoS One 6(4): 1-13 (Apr. 2011).

Scifers, J.R. Iontophoresis: maximizing treatment effectiveness. [online] [retrieved Aug. 11, 2009] URL: http://www.hnppharmaceuticals.com/pub_dwnlds/pdf/therapists/Ionto/Ionto_Max_effectivness.pdf.

Shomaker, T.S., et al. A pilot study assessing the impact of heat on the transdermal delivery of testosterone. Journal of Clinical Pharmacology 44: 677-682 (2001).

Singh, A., et al. Oral candidiasis: an overview. Journal of Oral and Maxillofacial Pathology 18(4): 81-85 (Sep. 2014).

Sotiriou, E., et al. Photodynamic therapy for distal and lateral subungual toenail onychomycosis caused by trichophyton rubrum: preliminary results of a single-centre open trial. Acta Dermato-Venereologica 90(2): 216-217 (2010).

Speakman, J., The micelle structure of the wool fibre. Proceedings of the Royal Society of London A 132: 167-191 (1931).

(56) References Cited

OTHER PUBLICATIONS

Speakman, J., and Elliot, G. Symposium on Fibrous Proteins, Soc. Dyers CoL, Leeds, UK, vol. 116 (1946).
Supparatpinyo, K., et al. Disseminated penicillium marneffei infection in southeast asia. The Lancet 344: 110-113 (Jul. 1994).
Swarbrick, J. Encyclopedia of Pharmaceutical Technology: 3848 (Oct. 2006).
Thevissen, K., et al. The plant defensin RsAFP2 induces cell wall stress, septin mislocation and accumulation of ceramides in candida albicans. Molecular Microbiology 84(1): 166-180 (2012).
Thomas, P.A. Fungal infections of the cornea. Eye 17(8): 852-862 (2003).
Thomas, D. How I won the war on toenail fungus (Feb. 2006) [online] URL: http://www.BottomLineSecrets.com.
Timby, B.K., et al. The Essentials of Nursing: Care of Adults and Children: 928 (2005).
Torano, A., et al. Complete amino acid sequence of the α2 heavy chain of a human IgA2 immunoglobulin of the A2m(2) allotype. Proceedings of the National Academy of Science 75(2): 966-969 (Feb. 1978).
Turley, S.M. Second-degree burn from iontophoresis. Consultant 48(5) (Apr. 2008) [online] [retrieved Aug. 11, 2009] URL: http://www.consultantlive.com/photoclinic/article/10162/1156010.
Van Der Weerden, N.L., et al. The plant defensing, NaD1, enters the cytoplasm of fusarium oxysporum hyphae. Journal of Biological Chemistry 283(21): 14445-14452 (2008).
Van Der Weerden, N.L., et al. Properties and mechanisms of action of naturally occurring antifungal peptides. Cellular and Molecular Life Sciences 70(19): 3545-3570 (2013).
Van Der Weerden, N.L., and Anderson, M.A. Plant defensins: common fold, multiple functions. Fungal Biology Reviews 26: 121-131 (2013).
Vibhagool, A., et al. Discontinuation of secondary phrophylaxis for cryptococcal meningitis in human immunodeficiency virus-infected patients treated with highly active antiretroviral therapy: a prospective, multicenter, randomized study. Clinical Infectious Diseases 36(10): 1329-1331 (2003).
Walters, K. A., et al. Physiochemical characterization of the human nail: I. Pressure sealed apparatus for measuring nail plate penmeabilities. Journal of Investigative Dermatology 76(2): 76-79 (Feb. 1981).
Westerberg, D.P., and Voyack, M. J. Onychomycosis: current trends in diagnosis and treatment. American Family Physician 88(11): 762-770 (Dec. 2013).
A trans-keratin drug delivery system for onychomycosis. Annual Meeting, Council for Nail Disorders (Feb. 1, 2007) URL: http://www.aad.org/meetings/previous/doc/Posters_2007%20Annual%20Meeting.pdf.
Lesions and shocks during iontophoresis. Health Devices 26(3): 123-125 (Mar. 1997) [online] [retrived on Aug. 11, 2009] URL: http://mdsr.ecri.org/summary/detail.aspx?doc_id=8170.
Altschul, S.F., et al. Gapped BLAST and PSI-BLAST: a new generation of protein database search programs. Nucleic Acids Research 25(17): 3389-3402 (1997).
Greco, W.R., et al. The search for synergy: a critical review from a response surface perspective. Pharmacological Reviews 47(2): 331-385 (1995).

\* cited by examiner

| | | | |
|---|---|---|---|
| HXL1 | T.aestivum | 100.00 | SEQ ID NO:4 |
| SbD17 | S.bicolor | 97.96 | SEQ ID NO:48 |
| ZmD9 | Z.mays | 97.96 | SEQ ID NO:49 |
| SoID1 | S.officinarum | 93.88 | SEQ ID NO:50 |
| ObD1 | O.brachyantha | 81.63 | SEQ ID NO:51 |
| | | | |
| HXL2 | T.aestivum | 100.00 | SEQ ID NO:5 |
| Ta-PDF30 | T.aestivum | 97.96 | SEQ ID NO:52 |
| TtD4 | T.turgidum | 97.96 | SEQ ID NO:53 |
| Ta-PDF25 | T.aestivum | 87.76 | SEQ ID NO:54 |
| TtD1 | T.turgidum | 85.71 | SEQ ID NO:55 |
| Tm-AMP-D1.2 | T.urartu | 85.71 | SEQ ID NO:56 |
| Ta-PDF23 | T.aestivum | 83.67 | SEQ ID NO:57 |
| TaD18 | T.aestivum | 83.67 | SEQ ID NO:58 |
| AtaD3 | A.tauschii | 82.98 | SEQ ID NO:59 |
| Tm-AMP-D1.2 | T.urartu | 82.98 | SEQ ID NO:60 |
| AtaD4 | A.tauschii | 81.63 | SEQ ID NO:61 |
| Ta-PDF13 | T.aestivum | 81.63 | SEQ ID NO:62 |
| TaD15 | T.aestivum | 81.63 | SEQ ID NO:63 |
| rmTAD1 | T.aestivum | 81.63 | SEQ ID NO:64 |
| TtD2 | T.turgidum | 81.63 | SEQ ID NO:65 |
| TtD5 | T.turgidum | 81.63 | SEQ ID NO:66 |

Figure 1(a)

| | | | |
|---|---|---|---|
| HXL4 | N.benthamiana | 100.00 | SEQ ID NO:7 |
| J1-2 | C.annuum | 95.74 | SEQ ID NO:67 |
| defensin | N.attenuata | 91.49 | SEQ ID NO:68 |
| StD15 | S.tuberosum | 91.49 | SEQ ID NO:69 |
| AtD84 | A.thaliana | 85.11 | SEQ ID NO:70 |
| PpD1 | P.persica | 85.11 | SEQ ID NO:71 |
| PpyD3 | P.pyrifolia | 85.11 | SEQ ID NO:72 |
| AhS4 | A.halleri | 82.98 | SEQ ID NO:73 |
| CanD5 | C.annuum | 82.98 | SEQ ID NO:74 |
| CsaD1 | C.sativa | 82.98 | SEQ ID NO:75 |
| Eg-PDF | E.grandis | 82.98 | SEQ ID NO:76 |
| Lm-PDF | L.michauxii | 82.98 | SEQ ID NO:77 |
| PvD3 | P.vulgaris | 82.98 | SEQ ID NO:78 |
| SlD17 | S.lycopersicum | 82.98 | SEQ ID NO:79 |
| Tm-PDF | T.majus | 82.98 | SEQ ID NO:80 |
| BnD9 | B.napus | 80.85 | SEQ ID NO:81 |
| CclD4 | C.clementina | 80.85 | SEQ ID NO:82 |
| CrD10 | C.rubella | 80.85 | SEQ ID NO:83 |
| CrD11 | C.rubella | 80.85 | SEQ ID NO:84 |
| Ct-PDF | C.tetragonoloba | 80.85 | SEQ ID NO:85 |
| Gm-PDF5 | G.max | 80.85 | SEQ ID NO:86 |
| GmD8 | G.max | 80.85 | SEQ ID NO:87 |
| LjD1 | L.japonicus | 80.85 | SEQ ID NO:88 |
| MtD23 | M.truncatula | 80.85 | SEQ ID NO:89 |
| NaD2 | N.alata | 80.85 | SEQ ID NO:90 |
| NtD4 | N.tabacum | 80.85 | SEQ ID NO:91 |
| ObD2 | O.brachyantha | 80.85 | SEQ ID NO:92 |
| PvD6 | P.vulgaris | 80.85 | SEQ ID NO:93 |
| ScD1 | S.chacoense | 80.85 | SEQ ID NO:94 |
| VuD2 | V.unguiculata | 80.85 | SEQ ID NO:95 |
| Vs-PDF | V.vinifera | 80.85 | SEQ ID NO:96 |

Figure 1(b)

| | | | |
|---|---|---|---|
| HXL8 | P.pentandra | 100.00 | SEQ ID NO:1 |
| Pp-PDF | P.pentandra | 78.00 | SEQ ID NO:97 |

| | | | |
|---|---|---|---|
| HXL9 | Z.mays | 100.00 | SEQ ID NO:9 |
| ZmD25 | Z.mays | 60.00 | SEQ ID NOL987 |

| | | | |
|---|---|---|---|
| HXL12 | A.retroflexus | 100.00 | SEQ ID NO:10 |
| SolD1 | S.oleracea | 66.67 | SEQ ID NO:99 |

| | | | |
|---|---|---|---|
| HXL13 | T.aestivum | 100.00 | SEQ ID NO:11 |
| GmD7 | G.max | 95.74 | SEQ ID NO:100 |

| | | | |
|---|---|---|---|
| HXL15 | O.sativa | 100.00 | SEQ ID NO:12 |
| DLP322 | B.distachyon | 81.63 | SEQ ID NO:101 |
| OsD17 | O.sativa | 97.96 | SEQ ID NO:102 |
| ObD1 | O.brachyantha | 93.88 | SEQ ID NO:103 |

| | | | |
|---|---|---|---|
| HXL32 | T.aestivum | 100.00 | SEQ ID NO:13 |
| Tk-AMP-D2 | A.tauschii | 97.96 | SEQ ID NO:104 |
| Ta-PDF33 | T.aestivum | 97.96 | SEQ ID NO:105 |
| TaD19 | T.aestivum | 93.88 | SEQ ID NO:106 |
| rmTAD1 | T.aestivum | 89.80 | SEQ ID NO:107 |
| Ta-PDF30 | T.aestivum | 81.63 | SEQ ID NO:108 |

Figure 1(c)

| | | | |
|---|---|---|---|
| HXL33 | P.argentatum | 100.00 | SEQ ID NO:14 |
| HaD3 | H.annuus | 87.23 | SEQ ID NO:109 |
| EpD2 | E.parvulum | 85.11 | SEQ ID NO:110 |
| JcD1 | J.curcas | 82.98 | SEQ ID NO:111 |
| PgD1 | P.ginseng | 82.98 | SEQ ID NO:112 |
| VfoD1 | V.fordii | 82.98 | SEQ ID NO:113 |
| BnD9 | B.napus | 80.85 | SEQ ID NO:114 |
| EsD5 | E.salsugineum | 80.85 | SEQ ID NO:115 |
| FvD6 | F.vesca | 80.85 | SEQ ID NO:116 |
| JcD2 | J.curcas | 80.85 | SEQ ID NO:117 |
| Pa-PDF | P.argentatum | 80.85 | SEQ ID NO:118 |
| RcD3 | R.communis | 80.85 | SEQ ID NO:119 |
| SlD20 | S.lycopersicum | 80.85 | SEQ ID NO:120 |
| StD13 | S.tuberosum | 80.85 | SEQ ID NO:121 |

| | | | |
|---|---|---|---|
| HXL34 | N.benthamiana | 100.00 | SEQ ID NO:15 |
| ScD1 | S.chacoense | 87.23 | SEQ ID NO:122 |
| SlD17 | S.lycopersicum | 85.11 | SEQ ID NO:123 |
| NaD2 | N.alata | 80.85 | SEQ ID NO:124 |
| NtD4 | N.tabacum | 80.85 | SEQ ID NO:125 |

Figure 1(d)

| | | | |
|---|---|---|---|
| NaD1 | N.alata | 100.00 | SEQ ID NO:18 |
| FST | N.tabacum | 97.87 | SEQ ID NO:126 |
| NtD3 | N.tabacum | 95.74 | SEQ ID NO:127 |
| NeThio2 | N.excelsior | 93.62 | SEQ ID NO:128 |
| SL14B1 | N.gossei | 93.62 | SEQ ID NO:129 |
| SL78B | N.amplexicaulis | 91.49 | SEQ ID NO:130 |
| NeD1 | N.excelsior | 91.49 | SEQ ID NO:131 |
| SL137 | N.goodspeedii | 91.49 | SEQ ID NO:132 |
| NsD1 | N.suaveolens | 91.49 | SEQ ID NO:16 |
| SL549 | N.burbidgeae | 89.36 | SEQ ID NO:133 |
| SL445 | N.truncata | 89.36 | SEQ ID NO:134 |
| SL99 | N.cavicola | 87.23 | SEQ ID NO:135 |
| NsD2 | N.suaveolens | 87.23 | SEQ ID NO:17 |
| SL446 | N.truncata | 87.23 | SEQ ID NO:136 |
| NpD1 | N.paniculata | 86.67 | SEQ ID NO:137 |
| SL548 | N.burbidgeae | 85.11 | SEQ ID NO:138 |
| SL97 | N.cavicola | 85.11 | SEQ ID NO:139 |
| SL16 | N.megalosiphon | 85.11 | SEQ ID NO:140 |
| SL12 | N.megalosiphon | 85.11 | SEQ ID NO:141 |
| SL543 | N.burbidgeae | 82.98 | SEQ ID NO:142 |
| SL14 | N.megalosiphon | 82.98 | SEQ ID NO:143 |
| NoD173 | N.occidentalis | 82.98 | SEQ ID NO:19 |
| SL171 | N.occidentalis | 80.85 | SEQ ID NO:144 |
| | | | |
| Dm-AMP1 | D.merckii | 100.00 | SEQ ID NO:20 |
| Vm-PDF | V.mespilifolia | 98.00 | SEQ ID NO:145 |
| VmD1 | V.mespilifolia | 96.00 | SEQ ID NO:146 |
| Ds-PDF | D.sinuata | 93.88 | SEQ ID NO:147 |
| Hs-PDF | H.annuus | 92.00 | SEQ ID NO:148 |
| Pa-PDF | P.argentatum | 92.00 | SEQ ID NO:149 |
| HaD2 | H.annuus | 88.00 | SEQ ID NO:150 |
| EprD1 | E.prostrata | 85.71 | SEQ ID NO:151 |
| PpeD5 | P.pentandra | 84.00 | SEQ ID NO:152 |

Figure 1(e)

```
              10        20        30        40        50
     ....|....|....|....|....|....|....|....|....|....|
HXL008     KVCTKPSKFFKGLCGTDGACTTACRKEGLHSGYCQLKGFLNSVCVCRKHC  SEQ ID NO:1
HXL035     KVCTKPSKFFKGLCGFDRDCTVACKKEGLASGFCQNKGFFNVVCVCRKPC  SEQ ID NO:2
HXL036     KVCTKPSKFFKGLCGADRDCTVACKKEGLATGFCQKKGFFNFVCVCRKPC  SEQ ID NO:3
consensus  KVCTKPSKFFKGLCGxDxxCTxACxKEGLxxGxCQxKGFxNxVCVCRKxC  SEQ ID NO:24
```

Figure 11

SEQUENCE LISTING

<160> NUMBER OF SEQ ID NOS: 152

<210> SEQ ID NO 1
<211> LENGTH: 50
<212> TYPE: PRT
<213> ORGANISM: artificial
<220> FEATURE:
<223> OTHER INFORMATION: HXL008 Picramnia pentandra

<400> SEQUENCE: 1

Lys Val Cys Thr Lys Pro Ser Lys Phe Phe Lys Gly Leu Cys Gly Thr
1               5                   10                  15

Asp Gly Ala Cys Thr Thr Ala Cys Arg Lys Glu Gly Leu His Ser Gly
            20                  25                  30

Tyr Cys Gln Leu Lys Gly Phe Leu Asn Ser Val Cys Val Cys Arg Lys
        35                  40                  45

His Cys
    50

<210> SEQ ID NO 2
<211> LENGTH: 50
<212> TYPE: PRT
<213> ORGANISM: artificial
<220> FEATURE:
<223> OTHER INFORMATION: HXL035 Picramnia pentandra

<400> SEQUENCE: 2

Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
            20                  25                  30

Phe Cys Gln Asn Lys Gly Phe Phe Asn Val Val Cys Val Cys Arg Lys
        35                  40                  45

Pro Cys
    50

<210> SEQ ID NO 3
<211> LENGTH: 50
<212> TYPE: PRT
<213> ORGANISM: artificial
<220> FEATURE:
<223> OTHER INFORMATION: HXL036 Picramnia pentandra

<400> SEQUENCE: 3

Lys Val Cys Thr Lys Pro Ser Lys Phe Phe Lys Gly Leu Cys Gly Ala
1               5                   10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Arg Lys
        35                  40                  45

Pro Cys
    50

<210> SEQ ID NO 4
<211> LENGTH: 49
<212> TYPE: PRT
<213> ORGANISM: artificial
<220> FEATURE:
<223> OTHER INFORMATION: HXL001 Zea mays

<400> SEQUENCE: 4

Arg His Cys Leu Ser Gln Ser His Arg Phe Lys Gly Leu Cys Met Ser

```
                1               5                  10                 15
Ser Asn Asn Cys Ala Asn Val Cys Gln Thr Glu Asn Phe Pro Gly Gly
            20                  25                 30

Glu Cys Lys Ala Glu Gly Ala Thr Arg Lys Cys Phe Cys Lys Lys Ile
            35                  40                 45

Cys
```

<210> SEQ ID NO 5
<211> LENGTH: 49
<212> TYPE: PRT
<213> ORGANISM: artificial
<220> FEATURE:
<223> OTHER INFORMATION: HXL002 Triticum aestivum

<400> SEQUENCE: 5

```
Arg Asp Cys Leu Ser Gln Ser His Lys Phe Lys Gly Ala Cys Leu Ser
1               5                  10                 15

Ser Ser Asn Cys Ala Ala Val Cys Arg Thr Glu Asn Phe Pro Asp Gly
            20                  25                 30

Glu Cys His Thr His Asn Phe Ala Arg Lys Cys Phe Cys Lys Arg Ala
            35                  40                 45

Cys
```

<210> SEQ ID NO 6
<211> LENGTH: 46
<212> TYPE: PRT
<213> ORGANISM: artificial
<220> FEATURE:
<223> OTHER INFORMATION: HXL003 Triticum aestivum

<400> SEQUENCE: 6

```
Ala Arg Asp Cys Thr Ser Gln Ser His Lys Phe Val Gly Leu Cys Leu
1               5                  10                 15

Ser Asp Arg Asn Cys Ala Ser Val Cys Leu Thr Glu Tyr Phe Thr Gly
            20                  25                 30

Gly Lys Cys Asp His Arg Arg Cys Val Cys Thr Lys Gly Cys
            35                  40                 45
```

<210> SEQ ID NO 7
<211> LENGTH: 47
<212> TYPE: PRT
<213> ORGANISM: artificial
<220> FEATURE:
<223> OTHER INFORMATION: HXL004 Nicotiana benthamiana

<400> SEQUENCE: 7

```
Arg Thr Cys Glu Ser Gln Ser His Arg Phe Lys Gly Leu Cys Phe Ser
1               5                  10                 15

Arg Ser Asn Cys Ala Ser Val Cys His Thr Glu Gly Phe Asn Gly Gly
            20                  25                 30

His Cys Arg Gly Phe Arg Arg Cys Phe Cys Thr Arg His Cys
            35                  40                 45
```

<210> SEQ ID NO 8
<211> LENGTH: 45
<212> TYPE: PRT
<213> ORGANISM: artificial
<220> FEATURE:
<223> OTHER INFORMATION: HXL005 Taraxcum kok-saghyz

<400> SEQUENCE: 8

Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45

<210> SEQ ID NO 9
<211> LENGTH: 51
<212> TYPE: PRT
<213> ORGANISM: artificial
<220> FEATURE:
<223> OTHER INFORMATION: HXL009 Zea mays

<400> SEQUENCE: 9

Thr Val Cys Met Arg His Asn Asn Phe Tyr His Gly Pro Cys Met Ser
1               5                   10                  15

Asn Lys Asp Cys Ala Asn Ser Cys Val Gln His Asn Leu Gly Val Gly
            20                  25                  30

Gly Tyr Cys Arg Gly Lys Ile Pro Phe Asn Lys Glu Cys Met Cys Thr
        35                  40                  45

Phe Glu Cys
    50

<210> SEQ ID NO 10
<211> LENGTH: 48
<212> TYPE: PRT
<213> ORGANISM: artificial
<220> FEATURE:
<223> OTHER INFORMATION: HXL012 Amaranthus retroflexus

<400> SEQUENCE: 10

Arg Met Cys Lys Ala Pro Ser Lys Leu Phe Arg Gly Met Cys Gly Ile
1               5                   10                  15

Arg Asp Ser Asn Cys Asp Ser Val Cys Arg Ala Glu Gly Met Ala Ala
            20                  25                  30

Gly Asp Cys His Gly Leu Arg Arg Cys Ile Cys Ser Arg Pro Cys
        35                  40                  45

<210> SEQ ID NO 11
<211> LENGTH: 47
<212> TYPE: PRT
<213> ORGANISM: artificial
<220> FEATURE:
<223> OTHER INFORMATION: HXL013 Glycine max

<400> SEQUENCE: 11

Lys Asp Cys Leu Thr Arg Arg His Gly Phe Gln Gly Arg Cys Leu Phe
1               5                   10                  15

Asp Arg Gln Cys Ala His Val Cys Arg Ser Asp Gly Phe Ile Gly Gly
            20                  25                  30

Gln Cys Arg Gly Pro Leu Arg Lys Cys Phe Cys Ser Arg Pro Cys
        35                  40                  45

<210> SEQ ID NO 12
<211> LENGTH: 49
<212> TYPE: PRT
<213> ORGANISM: artificial
<220> FEATURE:
<223> OTHER INFORMATION: HXL015 Oryza sativa

<400> SEQUENCE: 12

```
Arg His Cys Leu Ser Gln Ser His Arg Phe Lys Gly Met Cys Val Ser
1               5                   10                  15

Ser Asn Asn Cys Ala Asn Val Cys Arg Thr Glu Ser Phe Pro Asp Gly
            20                  25                  30

Glu Cys Lys Ser His Gly Leu Glu Arg Lys Cys Phe Cys Lys Lys Val
        35                  40                  45

Cys
```

<210> SEQ ID NO 13
<211> LENGTH: 49
<212> TYPE: PRT
<213> ORGANISM: artificial
<220> FEATURE:
<223> OTHER INFORMATION: HXL032 Triticum aestivum

<400> SEQUENCE: 13

```
Arg Thr Cys Leu Ser Gln Ser His Lys Phe Lys Gly Thr Cys Leu Ser
1               5                   10                  15

Asn Ser Asn Cys Ala Gly Val Cys Arg Thr Glu Asn Phe Pro Asp Gly
            20                  25                  30

Glu Cys Asn Ser His Arg Leu Glu Arg Lys Cys Phe Cys Lys Arg Thr
        35                  40                  45

Cys
```

<210> SEQ ID NO 14
<211> LENGTH: 47
<212> TYPE: PRT
<213> ORGANISM: artificial
<220> FEATURE:
<223> OTHER INFORMATION: HXL033 Parthenium argentatum

<400> SEQUENCE: 14

```
Arg Thr Cys Glu Ser Gln Ser His Lys Phe Lys Gly Thr Cys Leu Ser
1               5                   10                  15

Asp Thr Asn Cys Gly Asn Val Cys His Ser Glu Gly Phe Pro Gly Gly
            20                  25                  30

Lys Cys Arg Gly Leu Arg Arg Arg Cys Phe Cys Thr Lys Asn Cys
        35                  40                  45
```

<210> SEQ ID NO 15
<211> LENGTH: 47
<212> TYPE: PRT
<213> ORGANISM: artificial
<220> FEATURE:
<223> OTHER INFORMATION: HXL034 Nicotiana benthamiana

<400> SEQUENCE: 15

```
Arg Arg Cys Glu Ser Lys Ser Gln Arg Phe Lys Gly Pro Cys Val Arg
1               5                   10                  15

Val Lys Asn Cys Ala Ala Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45
```

<210> SEQ ID NO 16
<211> LENGTH: 47
<212> TYPE: PRT
<213> ORGANISM: artificial
<220> FEATURE:
<223> OTHER INFORMATION: NsD1 Nicotiana suaveolens

<400> SEQUENCE: 16

-continued

```
Lys Asp Cys Lys Arg Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 17
<211> LENGTH: 47
<212> TYPE: PRT
<213> ORGANISM: artificial
<220> FEATURE:
<223> OTHER INFORMATION: NsD2 Nicotiana suaveolens

<400> SEQUENCE: 17

```
Lys Asp Cys Lys Arg Glu Ser Asn Thr Phe Pro Gly Ile Cys Ile Thr
1               5                   10                  15

Lys Leu Pro Cys Arg Arg Ala Cys Ile Ser Glu Lys Phe Ala Asp Gly
            20                  25                  30

His Cys Ser Lys Ile Leu Arg Arg Cys Leu Cys Thr Lys Pro Cys
        35                  40                  45
```

<210> SEQ ID NO 18
<211> LENGTH: 47
<212> TYPE: PRT
<213> ORGANISM: artificial
<220> FEATURE:
<223> OTHER INFORMATION: NaD1 Nicotiana alata

<400> SEQUENCE: 18

```
Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 19
<211> LENGTH: 47
<212> TYPE: PRT
<213> ORGANISM: artificial
<220> FEATURE:
<223> OTHER INFORMATION: NoD173 Nicotiana occidentalis spp obliqua

<400> SEQUENCE: 19

```
Arg Gln Cys Lys Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
            20                  25                  30

His Cys Ser Lys Val Leu Arg Arg Cys Leu Cys Thr Lys Arg Cys
        35                  40                  45
```

<210> SEQ ID NO 20
<211> LENGTH: 50
<212> TYPE: PRT
<213> ORGANISM: artificial
<220> FEATURE:
<223> OTHER INFORMATION: DmAMP1 Dahlia merckii

<400> SEQUENCE: 20

```
Glu Leu Cys Glu Lys Ala Ser Lys Thr Trp Ser Gly Asn Cys Gly Asn
1               5                   10                  15
```

-continued

```
Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50

<210> SEQ ID NO 21
<211> LENGTH: 47
<212> TYPE: PRT
<213> ORGANISM: artificial
<220> FEATURE:
<223> OTHER INFORMATION: HXP4

<400> SEQUENCE: 21

Arg Glu Cys Lys Thr Glu Ser His Arg Phe Lys Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 22
<211> LENGTH: 47
<212> TYPE: PRT
<213> ORGANISM: artificial
<220> FEATURE:
<223> OTHER INFORMATION: HXP34

<400> SEQUENCE: 22

Arg Glu Cys Lys Thr Glu Ser Gln His His Ser Phe Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 23
<211> LENGTH: 47
<212> TYPE: PRT
<213> ORGANISM: artificial
<220> FEATURE:
<223> OTHER INFORMATION: HXP35

<400> SEQUENCE: 23

Arg Glu Cys Lys Thr Glu Ser Asp Thr Tyr Arg Gly Val Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 24
<211> LENGTH: 51
<212> TYPE: PRT
<213> ORGANISM: artificial
<220> FEATURE:
<223> OTHER INFORMATION: Consensus
<220> FEATURE:
<221> NAME/KEY: MISC_FEATURE
<222> LOCATION: (1)..(1)
<223> OTHER INFORMATION: X is optionally alanine or no residue
<220> FEATURE:
```

```
<221> NAME/KEY: MISC_FEATURE
<222> LOCATION: (2)..(51)
<223> OTHER INFORMATION: X is any amino acid

<400> SEQUENCE: 24

Xaa Lys Val Cys Thr Lys Pro Ser Lys Phe Phe Lys Gly Leu Cys Gly
1               5                   10                  15

Xaa Asp Xaa Xaa Cys Thr Xaa Ala Cys Xaa Lys Glu Gly Leu Xaa Xaa
            20                  25                  30

Gly Xaa Cys Gln Xaa Lys Gly Phe Xaa Asn Xaa Val Cys Val Cys Arg
        35                  40                  45

Lys Xaa Cys
    50

<210> SEQ ID NO 25
<211> LENGTH: 51
<212> TYPE: PRT
<213> ORGANISM: artificial
<220> FEATURE:
<223> OTHER INFORMATION: HXL008 + N-terminal alanine

<400> SEQUENCE: 25

Ala Lys Val Cys Thr Lys Pro Ser Lys Phe Phe Lys Gly Leu Cys Gly
1               5                   10                  15

Thr Asp Gly Ala Cys Thr Thr Ala Cys Arg Lys Glu Gly Leu His Ser
            20                  25                  30

Gly Tyr Cys Gln Leu Lys Gly Phe Leu Asn Ser Val Cys Val Cys Arg
        35                  40                  45

Lys His Cys
    50

<210> SEQ ID NO 26
<211> LENGTH: 51
<212> TYPE: PRT
<213> ORGANISM: artificial
<220> FEATURE:
<223> OTHER INFORMATION: HXL035  + N-terminal alanine

<400> SEQUENCE: 26

Ala Lys Val Cys Thr Lys Pro Ser Lys Phe Phe Lys Gly Leu Cys Gly
1               5                   10                  15

Phe Asp Arg Asp Cys Thr Val Ala Cys Lys Lys Glu Gly Leu Ala Ser
            20                  25                  30

Gly Phe Cys Gln Asn Lys Gly Phe Phe Asn Val Val Cys Val Cys Arg
        35                  40                  45

Lys Pro Cys
    50

<210> SEQ ID NO 27
<211> LENGTH: 51
<212> TYPE: PRT
<213> ORGANISM: artificial
<220> FEATURE:
<223> OTHER INFORMATION: HXL036  + N-terminal alanine

<400> SEQUENCE: 27

Ala Lys Val Cys Thr Lys Pro Ser Lys Phe Phe Lys Gly Leu Cys Gly
1               5                   10                  15

Ala Asp Arg Asp Cys Thr Val Ala Cys Lys Lys Glu Gly Leu Ala Thr
            20                  25                  30

Gly Phe Cys Gln Lys Lys Gly Phe Phe Asn Phe Val Cys Val Cys Arg
```

35                  40                  45

Lys Pro Cys
    50

<210> SEQ ID NO 28
<211> LENGTH: 50
<212> TYPE: PRT
<213> ORGANISM: artificial
<220> FEATURE:
<223> OTHER INFORMATION: HXL001 + N-terminal alanine

<400> SEQUENCE: 28

Ala Arg His Cys Leu Ser Gln Ser His Arg Phe Lys Gly Leu Cys Met
1               5                   10                  15

Ser Ser Asn Asn Cys Ala Asn Val Cys Gln Thr Glu Asn Phe Pro Gly
            20                  25                  30

Gly Glu Cys Lys Ala Glu Gly Ala Thr Arg Lys Cys Phe Cys Lys Lys
        35                  40                  45

Ile Cys
    50

<210> SEQ ID NO 29
<211> LENGTH: 50
<212> TYPE: PRT
<213> ORGANISM: artificial
<220> FEATURE:
<223> OTHER INFORMATION: HXL002  + N-terminal alanine

<400> SEQUENCE: 29

Ala Arg Asp Cys Leu Ser Gln Ser His Lys Phe Lys Gly Ala Cys Leu
1               5                   10                  15

Ser Ser Ser Asn Cys Ala Ala Val Cys Arg Thr Glu Asn Phe Pro Asp
            20                  25                  30

Gly Glu Cys His Thr His Asn Phe Ala Arg Lys Cys Phe Cys Lys Arg
        35                  40                  45

Ala Cys
    50

<210> SEQ ID NO 30
<211> LENGTH: 46
<212> TYPE: PRT
<213> ORGANISM: artificial
<220> FEATURE:
<223> OTHER INFORMATION: HXL003  + N-terminal alanine

<400> SEQUENCE: 30

Ala Arg Asp Cys Thr Ser Gln Ser His Lys Phe Val Gly Leu Cys Leu
1               5                   10                  15

Ser Asp Arg Asn Cys Ala Ser Val Cys Leu Thr Glu Tyr Phe Thr Gly
            20                  25                  30

Gly Lys Cys Asp His Arg Arg Cys Val Cys Thr Lys Gly Cys
        35                  40                  45

<210> SEQ ID NO 31
<211> LENGTH: 48
<212> TYPE: PRT
<213> ORGANISM: artificial
<220> FEATURE:
<223> OTHER INFORMATION: HXL004  + N-terminal alanine

<400> SEQUENCE: 31

Ala Arg Thr Cys Glu Ser Gln Ser His Arg Phe Lys Gly Leu Cys Phe

```
                1               5                  10                  15
Ser Arg Ser Asn Cys Ala Ser Val Cys His Thr Glu Gly Phe Asn Gly
                        20                  25                  30

Gly His Cys Arg Gly Phe Arg Arg Cys Phe Cys Thr Arg His Cys
            35                  40                  45
```

```
<210> SEQ ID NO 32
<211> LENGTH: 45
<212> TYPE: PRT
<213> ORGANISM: artificial
<220> FEATURE:
<223> OTHER INFORMATION: HXL005 + N-terminal alanine

<400> SEQUENCE: 32

Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
                20                  25                  30

Asp Gly Val Arg Arg Arg Cys Thr Cys Tyr Lys Lys Cys
            35                  40                  45

<210> SEQ ID NO 33
<211> LENGTH: 52
<212> TYPE: PRT
<213> ORGANISM: artificial
<220> FEATURE:
<223> OTHER INFORMATION: HXL009 + N-terminal alanine

<400> SEQUENCE: 33

Ala Thr Val Cys Met Arg His Asn Asn Phe Tyr His Gly Pro Cys Met
1               5                   10                  15

Ser Asn Lys Asp Cys Ala Asn Ser Cys Val Gln His Asn Leu Gly Val
                20                  25                  30

Gly Gly Tyr Cys Arg Gly Lys Ile Pro Phe Asn Lys Glu Cys Met Cys
            35                  40                  45

Thr Phe Glu Cys
    50

<210> SEQ ID NO 34
<211> LENGTH: 49
<212> TYPE: PRT
<213> ORGANISM: artificial
<220> FEATURE:
<223> OTHER INFORMATION: HXL012 + N-terminal alanine

<400> SEQUENCE: 34

Ala Arg Met Cys Lys Ala Pro Ser Lys Leu Phe Arg Gly Met Cys Gly
1               5                   10                  15

Ile Arg Asp Ser Asn Cys Asp Ser Val Cys Arg Ala Glu Gly Met Ala
                20                  25                  30

Ala Gly Asp Cys His Gly Leu Arg Arg Arg Cys Ile Cys Ser Arg Pro
            35                  40                  45

Cys

<210> SEQ ID NO 35
<211> LENGTH: 48
<212> TYPE: PRT
<213> ORGANISM: artificial
<220> FEATURE:
<223> OTHER INFORMATION: HXL013 + N-terminal alanine

<400> SEQUENCE: 35
```

```
Ala Lys Asp Cys Leu Thr Arg Arg His Gly Phe Gln Gly Arg Cys Leu
1               5                   10                  15

Phe Asp Arg Gln Cys Ala His Val Cys Arg Ser Asp Gly Phe Ile Gly
                20                  25                  30

Gly Gln Cys Arg Gly Pro Leu Arg Lys Cys Phe Cys Ser Arg Pro Cys
            35                  40                  45
```

<210> SEQ ID NO 36
<211> LENGTH: 50
<212> TYPE: PRT
<213> ORGANISM: artificial
<220> FEATURE:
<223> OTHER INFORMATION: HXL015 + N-terminal alanine

<400> SEQUENCE: 36

```
Ala Arg His Cys Leu Ser Gln Ser His Arg Phe Lys Gly Met Cys Val
1               5                   10                  15

Ser Ser Asn Asn Cys Ala Asn Val Cys Arg Thr Glu Ser Phe Pro Asp
                20                  25                  30

Gly Glu Cys Lys Ser His Gly Leu Glu Arg Lys Cys Phe Cys Lys Lys
            35                  40                  45

Val Cys
    50
```

<210> SEQ ID NO 37
<211> LENGTH: 50
<212> TYPE: PRT
<213> ORGANISM: artificial
<220> FEATURE:
<223> OTHER INFORMATION: HXL032 + N-terminal alanine

<400> SEQUENCE: 37

```
Ala Arg Thr Cys Leu Ser Gln Ser His Lys Phe Lys Gly Thr Cys Leu
1               5                   10                  15

Ser Asn Ser Asn Cys Ala Gly Val Cys Arg Thr Glu Asn Phe Pro Asp
                20                  25                  30

Gly Glu Cys Asn Ser His Arg Leu Glu Arg Lys Cys Phe Cys Lys Arg
            35                  40                  45

Thr Cys
    50
```

<210> SEQ ID NO 38
<211> LENGTH: 48
<212> TYPE: PRT
<213> ORGANISM: artificial
<220> FEATURE:
<223> OTHER INFORMATION: HXL033 + N-terminal alanine

<400> SEQUENCE: 38

```
Ala Arg Thr Cys Glu Ser Gln Ser His Lys Phe Lys Gly Thr Cys Leu
1               5                   10                  15

Ser Asp Thr Asn Cys Gly Asn Val Cys His Ser Glu Gly Phe Pro Gly
                20                  25                  30

Gly Lys Cys Arg Gly Leu Arg Arg Arg Cys Phe Cys Thr Lys Asn Cys
            35                  40                  45
```

<210> SEQ ID NO 39
<211> LENGTH: 48
<212> TYPE: PRT
<213> ORGANISM: artificial
<220> FEATURE:

<223> OTHER INFORMATION: HXL034 + N-terminal alanine

<400> SEQUENCE: 39

Ala Arg Arg Cys Glu Ser Lys Ser Gln Arg Phe Lys Gly Pro Cys Val
1               5                   10                  15

Arg Val Lys Asn Cys Ala Ala Val Cys Glu Thr Glu Gly Phe Ser Gly
            20                  25                  30

Gly Asp Cys Arg Gly Leu Arg Arg Cys Phe Cys Thr Arg Pro Cys
        35                  40                  45

<210> SEQ ID NO 40
<211> LENGTH: 48
<212> TYPE: PRT
<213> ORGANISM: artificial
<220> FEATURE:
<223> OTHER INFORMATION: NsD1   + N-terminal alanine

<400> SEQUENCE: 40

Ala Lys Asp Cys Lys Arg Glu Ser Asn Thr Phe Pro Gly Ile Cys Ile
1               5                   10                  15

Thr Lys Pro Pro Cys Arg Lys Ala Cys Ile Arg Glu Lys Phe Thr Asp
            20                  25                  30

Gly His Cys Ser Lys Ile Leu Arg Arg Cys Leu Cys Thr Lys Pro Cys
        35                  40                  45

<210> SEQ ID NO 41
<211> LENGTH: 48
<212> TYPE: PRT
<213> ORGANISM: artificial
<220> FEATURE:
<223> OTHER INFORMATION: NsD2  + N-terminal alanine

<400> SEQUENCE: 41

Ala Lys Asp Cys Lys Arg Glu Ser Asn Thr Phe Pro Gly Ile Cys Ile
1               5                   10                  15

Thr Lys Leu Pro Cys Arg Arg Ala Cys Ile Ser Glu Lys Phe Ala Asp
            20                  25                  30

Gly His Cys Ser Lys Ile Leu Arg Arg Cys Leu Cys Thr Lys Pro Cys
        35                  40                  45

<210> SEQ ID NO 42
<211> LENGTH: 48
<212> TYPE: PRT
<213> ORGANISM: artificial
<220> FEATURE:
<223> OTHER INFORMATION: NaD1  + N-terminal alanine

<400> SEQUENCE: 42

Ala Arg Glu Cys Lys Thr Glu Ser Asn Thr Phe Pro Gly Ile Cys Ile
1               5                   10                  15

Thr Lys Pro Pro Cys Arg Lys Ala Cys Ile Ser Glu Lys Phe Thr Asp
            20                  25                  30

Gly His Cys Ser Lys Ile Leu Arg Arg Cys Leu Cys Thr Lys Pro Cys
        35                  40                  45

<210> SEQ ID NO 43
<211> LENGTH: 48
<212> TYPE: PRT
<213> ORGANISM: artificial
<220> FEATURE:
<223> OTHER INFORMATION: NoD173   + N-terminal alanine

<400> SEQUENCE: 43

```
Ala Arg Gln Cys Lys Ala Glu Ser Asn Thr Phe Thr Gly Ile Cys Ile
 1               5                  10                  15

Ala Lys Pro Pro Cys Arg Gln Ala Cys Ile Arg Glu Lys Phe Thr Asp
                20                  25                  30

Gly His Cys Ser Lys Val Leu Arg Arg Cys Leu Cys Thr Lys Arg Cys
            35                  40                  45

<210> SEQ ID NO 44
<211> LENGTH: 51
<212> TYPE: PRT
<213> ORGANISM: artificial
<220> FEATURE:
<223> OTHER INFORMATION: DmAMP1  + N-terminal alanine

<400> SEQUENCE: 44

Ala Glu Leu Cys Glu Lys Ala Ser Lys Thr Trp Ser Gly Asn Cys Gly
 1               5                  10                  15

Asn Thr Gly His Cys Asp Asn Gln Cys Lys Ser Trp Glu Gly Ala Ala
                20                  25                  30

His Gly Ala Cys His Val Arg Asn Gly Lys His Met Cys Phe Cys Tyr
            35                  40                  45

Phe Asn Cys
        50

<210> SEQ ID NO 45
<211> LENGTH: 48
<212> TYPE: PRT
<213> ORGANISM: artificial
<220> FEATURE:
<223> OTHER INFORMATION: HXP4  + N-terminal alanine

<400> SEQUENCE: 45

Ala Arg Glu Cys Lys Thr Glu Ser His Arg Phe Lys Gly Pro Cys Ile
 1               5                  10                  15

Thr Lys Pro Pro Cys Arg Lys Ala Cys Ile Ser Glu Lys Phe Thr Asp
                20                  25                  30

Gly His Cys Ser Lys Ile Leu Arg Arg Cys Leu Cys Thr Lys Pro Cys
            35                  40                  45

<210> SEQ ID NO 46
<211> LENGTH: 48
<212> TYPE: PRT
<213> ORGANISM: artificial
<220> FEATURE:
<223> OTHER INFORMATION: HXP34  + N-terminal alanine

<400> SEQUENCE: 46

Ala Arg Glu Cys Lys Thr Glu Ser Gln His His Ser Phe Pro Cys Ile
 1               5                  10                  15

Thr Lys Pro Pro Cys Arg Lys Ala Cys Ile Ser Glu Lys Phe Thr Asp
                20                  25                  30

Gly His Cys Ser Lys Ile Leu Arg Arg Cys Leu Cys Thr Lys Pro Cys
            35                  40                  45

<210> SEQ ID NO 47
<211> LENGTH: 48
<212> TYPE: PRT
<213> ORGANISM: artificial
<220> FEATURE:
<223> OTHER INFORMATION: HXP35  + N-terminal alanine

<400> SEQUENCE: 47
```

Ala Arg Glu Cys Lys Thr Glu Ser Asp Thr Tyr Arg Gly Val Cys Ile
1               5                   10                  15

Thr Lys Pro Pro Cys Arg Lys Ala Cys Ile Ser Glu Lys Phe Thr Asp
            20                  25                  30

Gly His Cys Ser Lys Ile Leu Arg Arg Cys Leu Cys Thr Lys Pro Cys
        35                  40                  45

<210> SEQ ID NO 48
<211> LENGTH: 49
<212> TYPE: PRT
<213> ORGANISM: artificial
<220> FEATURE:
<223> OTHER INFORMATION: SbD17

<400> SEQUENCE: 48

Arg His Cys Leu Ser Gln Ser His Arg Phe Lys Gly Leu Cys Met Ser
1               5                   10                  15

Ser Thr Asn Cys Ala Asn Val Cys Gln Thr Glu Asn Phe Pro Gly Gly
            20                  25                  30

Glu Cys Lys Ala Glu Gly Ala Thr Arg Lys Cys Phe Cys Lys Lys Ile
        35                  40                  45

Cys

<210> SEQ ID NO 49
<211> LENGTH: 49
<212> TYPE: PRT
<213> ORGANISM: artificial
<220> FEATURE:
<223> OTHER INFORMATION: ZmD9

<400> SEQUENCE: 49

Arg His Cys Leu Ser Gln Ser His Arg Phe Lys Gly Leu Cys Met Ser
1               5                   10                  15

Ser Asn Asn Cys Ala Asn Val Cys Gln Thr Glu Asn Phe Pro Gly Gly
            20                  25                  30

Glu Cys Arg Ala Glu Gly Ala Thr Arg Lys Cys Phe Cys Lys Lys Ile
        35                  40                  45

Cys

<210> SEQ ID NO 50
<211> LENGTH: 49
<212> TYPE: PRT
<213> ORGANISM: artificial
<220> FEATURE:
<223> OTHER INFORMATION: SolD1

<400> SEQUENCE: 50

Arg Tyr Cys Leu Ser Gln Ser His Arg Phe Lys Gly Leu Cys Met Ser
1               5                   10                  15

Ser Ser Asn Cys Ala Asn Val Cys Gln Thr Glu Asn Phe Pro Gly Gly
            20                  25                  30

Glu Cys Lys Ala Asp Gly Ala Thr Arg Lys Cys Phe Cys Lys Lys Ile
        35                  40                  45

Cys

<210> SEQ ID NO 51
<211> LENGTH: 49
<212> TYPE: PRT
<213> ORGANISM: artificial
<220> FEATURE:

<223> OTHER INFORMATION: ObD1

<400> SEQUENCE: 51

Arg His Cys Leu Ser Gln Ser His Arg Phe Lys Gly Met Cys Val Ser
1               5                   10                  15

Ser Asn Asn Cys Ala Asn Val Cys Lys Thr Glu Asn Phe Pro Asp Gly
            20                  25                  30

Glu Cys Lys Ser His Gly Leu Glu Arg Lys Cys Phe Cys Lys Lys Leu
        35                  40                  45

Cys

<210> SEQ ID NO 52
<211> LENGTH: 49
<212> TYPE: PRT
<213> ORGANISM: artificial
<220> FEATURE:
<223> OTHER INFORMATION: Ta-PDF30

<400> SEQUENCE: 52

Arg Asp Cys Leu Ser Gln Ser His Lys Phe Lys Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys

<210> SEQ ID NO 53
<211> LENGTH: 49
<212> TYPE: PRT
<213> ORGANISM: artificial
<220> FEATURE:
<223> OTHER INFORMATION: TtD4

<400> SEQUENCE: 53

Arg Asp Cys Leu Ser Gln Ser His Lys Phe Lys Gly Ala Cys Leu Ser
1               5                   10                  15

Ser Ser Asn Cys Ala Ala Val Cys Arg Thr Glu Asn Phe Pro Asp Gly
            20                  25                  30

Glu Cys His Thr His Asn Phe Ala Arg Lys Cys Phe Cys Lys Arg Pro
        35                  40                  45

Cys

<210> SEQ ID NO 54
<211> LENGTH: 49
<212> TYPE: PRT
<213> ORGANISM: artificial
<220> FEATURE:
<223> OTHER INFORMATION: Ta-PDF25

<400> SEQUENCE: 54

Arg Asp Cys Leu Ser Gln Ser His Lys Phe Asn Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr Gln His Phe Glu Arg Lys Cys Phe Cys Lys Arg Val
        35                  40                  45

Cys

```
<210> SEQ ID NO 55
<211> LENGTH: 49
<212> TYPE: PRT
<213> ORGANISM: artificial
<220> FEATURE:
<223> OTHER INFORMATION: TtD1

<400> SEQUENCE: 55

Arg Asp Cys Val Ser Gln Ser His Asn Phe Lys Gly Ala Cys Leu Ser
1               5                   10                  15

Ser Ser Asn Cys Pro Ala Val Cys Arg Thr Glu Asn Phe Pro Asp Gly
            20                  25                  30

Glu Cys His Thr Pro His Phe Glu Arg Lys Cys Phe Cys Lys Arg Pro
        35                  40                  45

Cys

<210> SEQ ID NO 56
<211> LENGTH: 49
<212> TYPE: PRT
<213> ORGANISM: artificial
<220> FEATURE:
<223> OTHER INFORMATION: Tm-AMP-D1.2

<400> SEQUENCE: 56

Arg Asp Cys Val Ser Gln Ser His Asn Phe Lys Gly Ala Cys Leu Ser
1               5                   10                  15

Ser Ser Asn Cys Ala Ala Val Cys Arg Thr Asp Asn Phe Pro Asp Gly
            20                  25                  30

Glu Cys His Thr Pro His Phe Glu Arg Lys Cys Phe Cys Lys Arg Leu
        35                  40                  45

Cys

<210> SEQ ID NO 57
<211> LENGTH: 49
<212> TYPE: PRT
<213> ORGANISM: artificial
<220> FEATURE:
<223> OTHER INFORMATION: Ta-PDF23

<400> SEQUENCE: 57

Arg Asp Cys Leu Ser Gln Ser Phe Lys Phe Lys Gly Ala Cys Leu Ser
1               5                   10                  15

Ser Ser Asn Cys Ala Ala Val Cys Arg Thr Glu Lys Phe Pro Asp Gly
            20                  25                  30

Glu Cys His Arg Gln His Leu Glu Arg Lys Cys Phe Cys Lys Arg Pro
        35                  40                  45

Cys

<210> SEQ ID NO 58
<211> LENGTH: 49
<212> TYPE: PRT
<213> ORGANISM: artificial
<220> FEATURE:
<223> OTHER INFORMATION: TaD18

<400> SEQUENCE: 58

Arg Asn Cys Leu Ser Gln Ser His Asn Phe Lys Gly Ala Cys Leu Ser
1               5                   10                  15

Ser Ser Asn Cys Ala Ala Val Cys Arg Thr Glu Asn Phe Pro Asp Gly
            20                  25                  30

Glu Cys His Ala Pro His Tyr Glu Arg Lys Cys Phe Cys Lys Arg Pro
```

-continued

```
                35                  40                  45
Cys

<210> SEQ ID NO 59
<211> LENGTH: 50
<212> TYPE: PRT
<213> ORGANISM: artificial
<220> FEATURE:
<223> OTHER INFORMATION: AtaD3

<400> SEQUENCE: 59

Arg Asp Cys Leu Ser Lys Ser His Lys Phe Lys Gly Ala Cys Leu Ser
1               5                   10                  15

Ser Ser Asn Cys Ala Ser Ile Cys Arg Thr Glu Asn Phe Pro Gly Gly
            20                  25                  30

Glu Cys Lys Leu Asp Ser Phe Ala Arg Lys Cys Phe Cys Lys Arg Pro
        35                  40                  45

Thr His
    50

<210> SEQ ID NO 60
<211> LENGTH: 48
<212> TYPE: PRT
<213> ORGANISM: artificial
<220> FEATURE:
<223> OTHER INFORMATION: Tm-AMP-D1.2

<400> SEQUENCE: 60

Arg Asp Cys Leu Ser Lys Ser His Lys Phe Lys Gly Ala Cys Leu Ser
1               5                   10                  15

Ser Ser Asn Cys Ala Ser Ile Cys Arg Thr Glu Asn Phe Pro Gly Gly
            20                  25                  30

Glu Cys Lys Leu Asp Ser Phe Ala Arg Lys Cys Phe Cys Lys Arg Glu
        35                  40                  45

<210> SEQ ID NO 61
<211> LENGTH: 49
<212> TYPE: PRT
<213> ORGANISM: artificial
<220> FEATURE:
<223> OTHER INFORMATION: AtaD4

<400> SEQUENCE: 61

Arg Asp Cys Leu Ser Gln Ser Phe Lys Phe Lys Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Arg Gln His Leu Glu Arg Lys Cys Phe Cys Lys Lys Pro
        35                  40                  45

Cys

<210> SEQ ID NO 62
<211> LENGTH: 49
<212> TYPE: PRT
<213> ORGANISM: artificial
<220> FEATURE:
<223> OTHER INFORMATION: Ta-PDF13

<400> SEQUENCE: 62

Arg Asp Cys Leu Ser Gln Ser His Asn Phe Lys Gly Ala Cys Leu Ser
1               5                   10                  15
```

Ser Ser Asn Cys Ala Gly Val Cys His Thr Glu Ser Phe Pro Gly Gly
                20                  25                  30

Glu Cys His Thr Gln His Phe Glu Arg Lys Cys Phe Cys Lys Arg Val
            35                  40                  45

Cys

<210> SEQ ID NO 63
<211> LENGTH: 49
<212> TYPE: PRT
<213> ORGANISM: artificial
<220> FEATURE:
<223> OTHER INFORMATION: TaD15

<400> SEQUENCE: 63

Arg Asp Cys Leu Ser Lys Ser His Lys Phe Lys Gly Ala Cys Leu Ser
1               5                   10                  15

Ser Ser Asn Cys Ala Ser Ile Cys Arg Thr Glu Asn Phe Pro Gly Gly
                20                  25                  30

Glu Cys Lys Leu Asp Ser Phe Ala Arg Lys Cys Phe Cys Lys Arg Val
            35                  40                  45

Cys

<210> SEQ ID NO 64
<211> LENGTH: 49
<212> TYPE: PRT
<213> ORGANISM: artificial
<220> FEATURE:
<223> OTHER INFORMATION: mTAD1

<400> SEQUENCE: 64

Arg Thr Cys Leu Ser Gln Ser His Lys Phe Lys Gly Thr Cys Leu Ser
1               5                   10                  15

Asn Ser Asn Cys Ala Ala Val Cys Arg Thr Glu Asn Phe Pro Asp Gly
                20                  25                  30

Glu Cys Asn Thr His Leu Val Glu Arg Lys Cys Tyr Cys Lys Arg Thr
            35                  40                  45

Cys

<210> SEQ ID NO 65
<211> LENGTH: 49
<212> TYPE: PRT
<213> ORGANISM: artificial
<220> FEATURE:
<223> OTHER INFORMATION: TtD2

<400> SEQUENCE: 65

Arg Asp Cys Leu Ser Gln Ser His Lys Phe Lys Gly Ser Cys Leu Ser
1               5                   10                  15

Ser Ser Asn Cys Ala Ser Ile Cys Arg Thr Glu Asn Phe Pro Gly Gly
                20                  25                  30

Glu Cys Lys Leu Glu Ser Phe Ala Arg Lys Cys Phe Cys Lys Arg Val
            35                  40                  45

Cys

<210> SEQ ID NO 66
<211> LENGTH: 49
<212> TYPE: PRT
<213> ORGANISM: artificial
<220> FEATURE:
<223> OTHER INFORMATION: TtD5

```
<400> SEQUENCE: 66

Arg Asp Cys Leu Ser Gln Ser His Asn Phe Lys Gly Ala Cys Leu Ser
1               5                   10                  15

Ser Ser Asn Cys Ala Gly Val Cys His Thr Glu Ser Phe Pro Gly Gly
            20                  25                  30

Glu Cys His Thr Gln His Phe Glu Arg Lys Cys Phe Cys Lys Arg Pro
        35                  40                  45

Cys

<210> SEQ ID NO 67
<211> LENGTH: 47
<212> TYPE: PRT
<213> ORGANISM: artificial
<220> FEATURE:
<223> OTHER INFORMATION: J1-2

<400> SEQUENCE: 67

Arg Thr Cys Glu Ser Gln Ser His Arg Phe Lys Gly Leu Cys Phe Ser
1               5                   10                  15

Lys Ser Asn Cys Gly Ser Val Cys His Thr Glu Gly Phe Asn Gly Gly
            20                  25                  30

His Cys Arg Gly Phe Arg Arg Arg Cys Phe Cys Thr Arg His Cys
        35                  40                  45

<210> SEQ ID NO 68
<211> LENGTH: 47
<212> TYPE: PRT
<213> ORGANISM: artificial
<220> FEATURE:
<223> OTHER INFORMATION: defensin

<400> SEQUENCE: 68

Arg Thr Cys Glu Ser Gln Ser Arg Arg Phe Arg Gly Leu Cys Phe Ser
1               5                   10                  15

Lys Ser Asn Cys Gly Ser Val Cys His Thr Glu Gly Phe Asn Gly Gly
            20                  25                  30

His Cys Arg Gly Phe Arg Arg Arg Cys Phe Cys Thr Arg His Cys
        35                  40                  45

<210> SEQ ID NO 69
<211> LENGTH: 47
<212> TYPE: PRT
<213> ORGANISM: artificial
<220> FEATURE:
<223> OTHER INFORMATION: StD15

<400> SEQUENCE: 69

Arg Thr Cys Glu Ser Gln Ser Arg Arg Phe Lys Gly Leu Cys Phe Ser
1               5                   10                  15

Lys Ser Asn Cys Gly Ser Val Cys His Thr Glu Gly Phe Ser Gly Gly
            20                  25                  30

His Cys Arg Gly Phe Arg Arg Arg Cys Phe Cys Thr Arg His Cys
        35                  40                  45

<210> SEQ ID NO 70
<211> LENGTH: 47
<212> TYPE: PRT
<213> ORGANISM: artificial
<220> FEATURE:
<223> OTHER INFORMATION: AtD84

<400> SEQUENCE: 70
```

```
Arg Thr Cys Glu Ser Gln Ser His Arg Phe Lys Gly Thr Cys Val Ser
1               5                   10                  15

Ala Ser Asn Cys Ala Asn Val Cys His Asn Glu Gly Phe Val Gly Gly
                20                  25                  30

Asn Cys Arg Gly Phe Arg Arg Arg Cys Phe Cys Thr Arg His Cys
            35                  40                  45
```

<210> SEQ ID NO 71
<211> LENGTH: 47
<212> TYPE: PRT
<213> ORGANISM: artificial
<220> FEATURE:
<223> OTHER INFORMATION: PpD1

<400> SEQUENCE: 71

```
Arg Thr Cys Glu Ser Gln Ser Asn Arg Phe Lys Gly Thr Cys Val Ser
1               5                   10                  15

Thr Ser Asn Cys Ala Ser Val Cys Gln Thr Glu Gly Phe Pro Gly Gly
                20                  25                  30

His Cys Arg Gly Phe Arg Arg Arg Cys Phe Cys Thr Lys His Cys
            35                  40                  45
```

<210> SEQ ID NO 72
<211> LENGTH: 47
<212> TYPE: PRT
<213> ORGANISM: artificial
<220> FEATURE:
<223> OTHER INFORMATION: PpyD3

<400> SEQUENCE: 72

```
Arg Thr Cys Glu Ser Gln Ser Arg Lys Phe Lys Gly Ala Cys Leu Ser
1               5                   10                  15

Arg Ser Asn Cys Ala Ser Val Cys Gln Thr Glu Gly Phe Pro Gly Gly
                20                  25                  30

His Cys Arg Gly Phe Arg Arg Arg Cys Phe Cys Thr Lys His Cys
            35                  40                  45
```

<210> SEQ ID NO 73
<211> LENGTH: 47
<212> TYPE: PRT
<213> ORGANISM: artificial
<220> FEATURE:
<223> OTHER INFORMATION: AhS4

<400> SEQUENCE: 73

```
Arg Thr Cys Glu Ser Gln Ser His Arg Phe Lys Gly Thr Cys Val Ser
1               5                   10                  15

Ala Ser Asn Cys Ala Asn Val Cys His Asn Glu Gly Phe Ile Gly Gly
                20                  25                  30

Asn Cys Arg Gly Phe Arg Arg Arg Cys Phe Cys Thr Arg Asn Cys
            35                  40                  45
```

<210> SEQ ID NO 74
<211> LENGTH: 47
<212> TYPE: PRT
<213> ORGANISM: artificial
<220> FEATURE:
<223> OTHER INFORMATION: CanD5

<400> SEQUENCE: 74

```
Arg Thr Cys Glu Ser Gln Ser His Arg Phe Lys Gly Val Cys Ala Ser
1               5                   10                  15
```

Glu Thr Asn Cys Ala Ser Val Cys Gln Thr Glu Gly Phe Ser Gly Gly
            20                  25                  30

Asp Cys Arg Gly Phe Arg Arg Arg Cys Phe Cys Thr Arg Pro Cys
        35                  40                  45

<210> SEQ ID NO 75
<211> LENGTH: 47
<212> TYPE: PRT
<213> ORGANISM: artificial
<220> FEATURE:
<223> OTHER INFORMATION: CsaD1

<400> SEQUENCE: 75

Arg Thr Cys Glu Ser Gln Ser His Arg Phe Lys Gly Pro Cys Val Arg
1               5                   10                  15

Lys Ser Asn Cys Ala Ser Val Cys Gln Thr Glu Gly Phe His Gly Gly
            20                  25                  30

Gln Cys Arg Gly Phe Arg Arg Arg Cys Phe Cys Thr Lys His Cys
        35                  40                  45

<210> SEQ ID NO 76
<211> LENGTH: 47
<212> TYPE: PRT
<213> ORGANISM: artificial
<220> FEATURE:
<223> OTHER INFORMATION: Eg-PDF

<400> SEQUENCE: 76

Arg Thr Cys Glu Ser Gln Ser Gln Arg Phe Lys Gly Ala Cys Val Ser
1               5                   10                  15

Lys Thr Asn Cys Ala Ser Val Cys Gln Thr Glu Gly Phe His Gly Gly
            20                  25                  30

His Cys Arg Gly Phe Arg Arg Arg Cys Phe Cys Thr Lys His Cys
        35                  40                  45

<210> SEQ ID NO 77
<211> LENGTH: 47
<212> TYPE: PRT
<213> ORGANISM: artificial
<220> FEATURE:
<223> OTHER INFORMATION: Lm-PDF

<400> SEQUENCE: 77

Arg Thr Cys Glu Ser Gln Ser His Arg Phe Lys Gly Ile Cys Val Arg
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys His Cys
        35                  40                  45

<210> SEQ ID NO 78
<211> LENGTH: 47
<212> TYPE: PRT
<213> ORGANISM: artificial
<220> FEATURE:
<223> OTHER INFORMATION: PvD3

<400> SEQUENCE: 78

Arg Thr Cys Glu Ser Gln Ser His Arg Phe Lys Gly Pro Cys Val Ser
1               5                   10                  15

Asp Thr Asn Cys Ala Ser Val Cys Arg Thr Glu Arg Phe Ser Gly Gly
            20                  25                  30

His Cys Arg Gly Phe Arg Arg Arg Cys Phe Cys Thr Lys His Cys
        35                  40                  45

<210> SEQ ID NO 79
<211> LENGTH: 47
<212> TYPE: PRT
<213> ORGANISM: artificial
<220> FEATURE:
<223> OTHER INFORMATION: SID17

<400> SEQUENCE: 79

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Phe Arg Arg Arg Cys Phe Cys Thr Arg Pro Cys
        35                  40                  45

<210> SEQ ID NO 80
<211> LENGTH: 47
<212> TYPE: PRT
<213> ORGANISM: artificial
<220> FEATURE:
<223> OTHER INFORMATION: Tm-PDF

<400> SEQUENCE: 80

Arg Thr Cys Glu Ser Gln Ser His Arg Phe Lys Gly Pro Cys Val Ser
1               5                   10                  15

Lys Thr Asn Cys Ala Ser Val Cys Lys Thr Glu Gly Phe Tyr Gly Gly
            20                  25                  30

His Cys Arg Gly Phe Arg His Arg Cys Phe Cys Thr Lys His Cys
        35                  40                  45

<210> SEQ ID NO 81
<211> LENGTH: 47
<212> TYPE: PRT
<213> ORGANISM: artificial
<220> FEATURE:
<223> OTHER INFORMATION: BnD9

<400> SEQUENCE: 81

Arg Thr Cys Glu Ser Gln Ser His Arg Phe Lys Gly Pro Cys Val Ser
1               5                   10                  15

Asp Asn Asn Cys Ala Asn Val Cys His Asn Glu Gly Phe Gly Gly Gly
            20                  25                  30

Lys Cys Arg Gly Leu Arg Arg Arg Cys Phe Cys Thr Arg His Cys
        35                  40                  45

<210> SEQ ID NO 82
<211> LENGTH: 47
<212> TYPE: PRT
<213> ORGANISM: artificial
<220> FEATURE:
<223> OTHER INFORMATION: Cc1D4

<400> SEQUENCE: 82

Arg Ile Cys Glu Ser Gln Ser His Arg Phe Lys Gly Pro Cys Val Ser
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys Arg Cys
        35                  40                  45

<210> SEQ ID NO 83
<211> LENGTH: 47
<212> TYPE: PRT
<213> ORGANISM: artificial
<220> FEATURE:
<223> OTHER INFORMATION: CrD10

<400> SEQUENCE: 83

Arg Thr Cys Glu Ser Lys Ser His Arg Phe Lys Gly Thr Cys Leu Ser
1               5                   10                  15

Glu Ser Asn Cys Lys Asn Val Cys His Asn Glu Gly Phe Gln Gly Gly
            20                  25                  30

Asn Cys Arg Gly Phe Arg Arg Arg Cys Phe Cys Thr Arg His Cys
        35                  40                  45

<210> SEQ ID NO 84
<211> LENGTH: 47
<212> TYPE: PRT
<213> ORGANISM: artificial
<220> FEATURE:
<223> OTHER INFORMATION: CrD11

<400> SEQUENCE: 84

Arg Thr Cys Glu Ser Lys Ser His Arg Phe Lys Gly Lys Cys Phe Ser
1               5                   10                  15

Glu Thr Asn Cys Lys Asn Val Cys His Asn Glu Gly Phe Thr Gly Gly
            20                  25                  30

Asn Cys Arg Gly Phe Arg Arg Arg Cys Phe Cys Thr Arg His Cys
        35                  40                  45

<210> SEQ ID NO 85
<211> LENGTH: 47
<212> TYPE: PRT
<213> ORGANISM: artificial
<220> FEATURE:
<223> OTHER INFORMATION: Ct-PDF

<400> SEQUENCE: 85

Arg Ser Cys Glu Ser Gln Ser His Arg Phe Lys Gly Pro Cys Val Ser
1               5                   10                  15

Asp Thr Asn Cys Ala Ser Val Cys Tyr Thr Glu Arg Phe Ser Gly Gly
            20                  25                  30

His Cys Arg Gly Phe Arg Arg Arg Cys Phe Cys Thr Lys His Cys
        35                  40                  45

<210> SEQ ID NO 86
<211> LENGTH: 47
<212> TYPE: PRT
<213> ORGANISM: artificial
<220> FEATURE:
<223> OTHER INFORMATION: Gm-PDF5

<400> SEQUENCE: 86

Arg His Cys Glu Ser Lys Ser His Arg Phe Lys Gly Met Cys Leu Ser
1               5                   10                  15

Lys His Asn Cys Ala Ser Val Cys His Leu Glu Gly Phe Thr Gly Gly
            20                  25                  30

Lys Cys Arg Gly Phe Arg Arg Arg Cys Phe Cys Thr Arg His Cys
        35                  40                  45

<210> SEQ ID NO 87

<210> SEQ ID NO 87
<211> LENGTH: 47
<212> TYPE: PRT
<213> ORGANISM: artificial
<220> FEATURE:
<223> OTHER INFORMATION: GmD8

<400> SEQUENCE: 87

Arg Thr Cys Glu Ser Gln Ser His Arg Phe Lys Gly Pro Cys Leu Ser
1               5                   10                  15

Asp Thr Asn Cys Gly Ser Val Cys Arg Thr Glu Arg Phe Thr Gly Gly
            20                  25                  30

His Cys Arg Gly Phe Arg Arg Arg Cys Phe Cys Thr Lys His Cys
        35                  40                  45

<210> SEQ ID NO 88
<211> LENGTH: 47
<212> TYPE: PRT
<213> ORGANISM: artificial
<220> FEATURE:
<223> OTHER INFORMATION: LjD1

<400> SEQUENCE: 88

Arg Asp Cys Glu Ser Gln Ser His Arg Phe Lys Gly Pro Cys Val Ser
1               5                   10                  15

Asp Thr Asn Cys Ala Ser Val Cys His Gly Glu Lys Phe Ser Gly Gly
            20                  25                  30

His Cys Arg Gly Phe Arg Arg Arg Cys Phe Cys Thr Lys His Cys
        35                  40                  45

<210> SEQ ID NO 89
<211> LENGTH: 47
<212> TYPE: PRT
<213> ORGANISM: artificial
<220> FEATURE:
<223> OTHER INFORMATION: MtD23

<400> SEQUENCE: 89

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

His Cys Arg Gly Phe Arg Arg Arg Cys Phe Cys Thr Thr His Cys
        35                  40                  45

<210> SEQ ID NO 90
<211> LENGTH: 47
<212> TYPE: PRT
<213> ORGANISM: artificial
<220> FEATURE:
<223> OTHER INFORMATION: NaD2

<400> SEQUENCE: 90

Arg Thr Cys Glu Ser Gln Ser His Arg Phe Lys Gly Pro Cys Ala Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Phe Cys Thr Arg Pro Cys
        35                  40                  45

<210> SEQ ID NO 91
<211> LENGTH: 47
<212> TYPE: PRT
<213> ORGANISM: artificial

-continued

```
<220> FEATURE:
<223> OTHER INFORMATION: NtD4

<400> SEQUENCE: 91

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Cys Phe Cys Thr Arg Pro Cys
        35                  40                  45

<210> SEQ ID NO 92
<211> LENGTH: 47
<212> TYPE: PRT
<213> ORGANISM: artificial
<220> FEATURE:
<223> OTHER INFORMATION: ObD2

<400> SEQUENCE: 92

Arg Thr Cys Glu Ser Gln Ser His Arg Phe Asn Gly Val Cys Val Arg
1               5                   10                  15

Ser Ser Asn Cys Ala Ser Val Cys Ser Thr Glu Gly Phe Thr Gly Gly
            20                  25                  30

His Cys Arg Gly Phe Arg Arg Arg Cys Phe Cys Thr Lys Pro Cys
        35                  40                  45

<210> SEQ ID NO 93
<211> LENGTH: 47
<212> TYPE: PRT
<213> ORGANISM: artificial
<220> FEATURE:
<223> OTHER INFORMATION: PvD6

<400> SEQUENCE: 93

Arg His Cys Glu Ser Lys Ser His Arg Phe Lys Gly Met Cys Leu Ser
1               5                   10                  15

Asp Arg Asn Cys Ala Ser Val Cys His Leu Glu Gly Phe Thr Gly Gly
            20                  25                  30

Asn Cys Arg Gly Phe Arg Arg Arg Cys Phe Cys Thr Arg His Cys
        35                  40                  45

<210> SEQ ID NO 94
<211> LENGTH: 47
<212> TYPE: PRT
<213> ORGANISM: artificial
<220> FEATURE:
<223> OTHER INFORMATION: ScD1

<400> SEQUENCE: 94

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45

<210> SEQ ID NO 95
<211> LENGTH: 47
<212> TYPE: PRT
<213> ORGANISM: artificial
<220> FEATURE:
<223> OTHER INFORMATION: VuD2
```

<400> SEQUENCE: 95

Arg Thr Cys Glu Ser Gln Ser His Arg Phe Lys Gly Pro Cys Val Ser
1               5                   10                  15

Asp Thr Asn Cys Ala Ser Val Cys Arg Thr Glu Arg Phe Ser Gly Gly
            20                  25                  30

His Cys Arg Gly Phe Arg Arg Arg Cys Leu Cys Thr Lys His Cys
        35                  40                  45

<210> SEQ ID NO 96
<211> LENGTH: 47
<212> TYPE: PRT
<213> ORGANISM: artificial
<220> FEATURE:
<223> OTHER INFORMATION: Vs-PDF

<400> SEQUENCE: 96

Arg Thr Cys Glu Ser Gln Ser His Arg Phe Lys Gly Thr Cys Val Arg
1               5                   10                  15

Gln Ser Asn Cys Ala Ala Val Cys Gln Thr Glu Gly Phe His Gly Gly
            20                  25                  30

Asn Cys Arg Gly Phe Arg Arg Arg Cys Phe Cys Thr Lys His Cys
        35                  40                  45

<210> SEQ ID NO 97
<211> LENGTH: 50
<212> TYPE: PRT
<213> ORGANISM: artificial
<220> FEATURE:
<223> OTHER INFORMATION: Pp-PDF

<400> SEQUENCE: 97

Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
            20                  25                  30

Phe Cys Gln Asn Lys Gly Phe Phe Asn Val Val Cys Val Cys Arg Lys
        35                  40                  45

Pro Cys
    50

<210> SEQ ID NO 98
<211> LENGTH: 51
<212> TYPE: PRT
<213> ORGANISM: artificial
<220> FEATURE:
<223> OTHER INFORMATION: ZmD25

<400> SEQUENCE: 98

Glu Ile Cys Ala Arg Pro Asn Pro His Tyr Pro Gly Ala Cys Arg Ser
1               5                   10                  15

Asn Lys Asp Cys Ala Gly Ser Cys Ile Gln Gln Asn Leu Gly Thr Ser
            20                  25                  30

Gly Tyr Cys Lys Gly Ser Val Pro Leu Phe Lys Ser Cys Tyr Cys Thr
        35                  40                  45

Phe Glu Cys
    50

<210> SEQ ID NO 99
<211> LENGTH: 47
<212> TYPE: PRT
<213> ORGANISM: artificial

<220> FEATURE:
<223> OTHER INFORMATION: SolD1

<400> SEQUENCE: 99

Arg Lys Cys Lys Thr Pro Ser Lys Thr Phe Lys Gly Ile Cys Thr Arg
1               5                   10                  15

Asp Ser Asn Cys Asp Thr Ser Cys Arg Tyr Glu Gly Tyr Pro Ala Gly
            20                  25                  30

Asp Cys Lys Gly Ile Arg Arg Arg Cys Met Cys Ser Lys Pro Cys
        35                  40                  45

<210> SEQ ID NO 100
<211> LENGTH: 47
<212> TYPE: PRT
<213> ORGANISM: artificial
<220> FEATURE:
<223> OTHER INFORMATION: GmD7

<400> SEQUENCE: 100

Lys Asp Cys Leu Thr Arg Arg His Gly Phe Gln Gly Arg Cys Leu Phe
1               5                   10                  15

Asp Arg Gln Cys Val His Val Cys Arg Ser Asp Gly Phe Ile Gly Gly
            20                  25                  30

Gln Cys Arg Gly Pro Leu Arg Lys Cys Val Cys Ser Arg Pro Cys
        35                  40                  45

<210> SEQ ID NO 101
<211> LENGTH: 49
<212> TYPE: PRT
<213> ORGANISM: artificial
<220> FEATURE:
<223> OTHER INFORMATION: DLP322

<400> SEQUENCE: 101

Arg His Cys Leu Ser Gln Ser His Arg Phe Lys Gly Met Cys Val Ser
1               5                   10                  15

Ser Asn Asn Cys Ala Asn Val Cys Arg Thr Glu Ser Phe Pro Asp Gly
            20                  25                  30

Glu Cys Lys Ser His Gly Leu Glu Arg Lys Cys Phe Cys Lys Lys Pro
        35                  40                  45

Cys

<210> SEQ ID NO 102
<211> LENGTH: 49
<212> TYPE: PRT
<213> ORGANISM: artificial
<220> FEATURE:
<223> OTHER INFORMATION: OsD17

<400> SEQUENCE: 102

Arg His Cys Leu Ser Gln Ser His Arg Phe Lys Gly Met Cys Val Ser
1               5                   10                  15

Ser Asn Asn Cys Ala Asn Val Cys Lys Thr Glu Asn Phe Pro Asp Gly
            20                  25                  30

Glu Cys Lys Ser His Gly Leu Glu Arg Lys Cys Phe Cys Lys Lys Leu
        35                  40                  45

Cys

<210> SEQ ID NO 103
<211> LENGTH: 49
<212> TYPE: PRT

```
<213> ORGANISM: artificial
<220> FEATURE:
<223> OTHER INFORMATION: ObD1

<400> SEQUENCE: 103

Arg His Cys Leu Ser Gln Ser His Lys Phe Lys Gly Thr Cys Val Arg
1               5                   10                  15

Ser Gly Asn Cys Ala Asn Val Cys Lys Thr Glu Asn Phe Pro Asp Gly
            20                  25                  30

Glu Cys Lys Thr Gln Gly Leu Glu Arg Lys Cys Phe Cys Lys Arg Val
        35                  40                  45

Cys

<210> SEQ ID NO 104
<211> LENGTH: 49
<212> TYPE: PRT
<213> ORGANISM: artificial
<220> FEATURE:
<223> OTHER INFORMATION: Tk-AMP-D2

<400> SEQUENCE: 104

Arg Thr Cys Leu Ser Gln Ser His Lys Phe Lys Gly Thr Cys Leu Ser
1               5                   10                  15

Asn Ser Asn Cys Ala Gly Val Cys Arg Thr Glu Asn Phe Pro Asp Gly
            20                  25                  30

Glu Cys Asn Ser His Arg Leu Glu Arg Lys Cys Tyr Cys Lys Arg Thr
        35                  40                  45

Cys

<210> SEQ ID NO 105
<211> LENGTH: 49
<212> TYPE: PRT
<213> ORGANISM: artificial
<220> FEATURE:
<223> OTHER INFORMATION: Ta-PDF33

<400> SEQUENCE: 105

Arg Thr Cys Leu Ser Gln Ser His Lys Phe Lys Gly Thr Cys Leu Ser
1               5                   10                  15

Asp Ser Asn Cys Ala Gly Val Cys Arg Thr Glu Asn Phe Pro Asp Gly
            20                  25                  30

Glu Cys Asn Ser His Arg Leu Glu Arg Lys Cys Phe Cys Lys Arg Thr
        35                  40                  45

Cys

<210> SEQ ID NO 106
<211> LENGTH: 49
<212> TYPE: PRT
<213> ORGANISM: artificial
<220> FEATURE:
<223> OTHER INFORMATION: TaD19

<400> SEQUENCE: 106

Arg Thr Cys Leu Ser Gln Ser His Lys Phe Lys Gly Thr Cys Ile Ser
1               5                   10                  15

Asp Ser Asn Cys Ala Gly Val Cys Arg Thr Glu Asn Phe Pro Asp Gly
            20                  25                  30

Glu Cys Asn Ser His Arg Leu Glu Arg Lys Cys His Cys Lys Arg Thr
        35                  40                  45

Cys
```

```
<210> SEQ ID NO 107
<211> LENGTH: 49
<212> TYPE: PRT
<213> ORGANISM: artificial
<220> FEATURE:
<223> OTHER INFORMATION: mTAD1

<400> SEQUENCE: 107
```

Arg Thr Cys Leu Ser Gln Ser His Lys Phe Lys Gly Thr Cys Leu Ser
1               5                   10                  15

Asn Ser Asn Cys Ala Ala Val Cys Arg Thr Glu Asn Phe Pro Asp Gly
            20                  25                  30

Glu Cys Asn Thr His Leu Val Glu Arg Lys Cys Tyr Cys Lys Arg Thr
        35                  40                  45

Cys

```
<210> SEQ ID NO 108
<211> LENGTH: 49
<212> TYPE: PRT
<213> ORGANISM: artificial
<220> FEATURE:
<223> OTHER INFORMATION: Ta-PDF30

<400> SEQUENCE: 108
```

Arg Asp Cys Leu Ser Gln Ser His Lys Phe Lys Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys

```
<210> SEQ ID NO 109
<211> LENGTH: 47
<212> TYPE: PRT
<213> ORGANISM: artificial
<220> FEATURE:
<223> OTHER INFORMATION: HaD3

<400> SEQUENCE: 109
```

Arg Thr Cys Glu Ser Gln Ser His Lys Phe Lys Gly Thr Cys Leu Ser
1               5                   10                  15

Asp Thr Asn Cys Ala Asn Val Cys His Ser Glu Arg Phe Ser Gly Gly
            20                  25                  30

Lys Cys Arg Gly Phe Arg Arg Arg Cys Phe Cys Thr Thr His Cys
        35                  40                  45

```
<210> SEQ ID NO 110
<211> LENGTH: 47
<212> TYPE: PRT
<213> ORGANISM: artificial
<220> FEATURE:
<223> OTHER INFORMATION: EpD2

<400> SEQUENCE: 110
```

Arg Thr Cys Glu Ser Gln Ser His Arg Phe Lys Gly Lys Cys Leu Ser
1               5                   10                  15

Asp Gly Asn Cys Gly Asn Val Cys His Asn Glu Gly Phe Gly Gly Gly
            20                  25                  30

Lys Cys Arg Gly Phe Arg Arg Arg Cys Phe Cys Thr Arg Asn Cys

<210> SEQ ID NO 111
<211> LENGTH: 47
<212> TYPE: PRT
<213> ORGANISM: artificial
<220> FEATURE:
<223> OTHER INFORMATION: JcD1

<400> SEQUENCE: 111

Arg Thr Cys Glu Ser Gln Ser His Lys Phe Lys Gly Thr Cys Leu Ser
1               5                   10                  15

Glu Thr Asn Cys Ala Asn Val Cys Lys Thr Glu Gly Phe Thr Gly Gly
            20                  25                  30

Asp Cys Arg Gly Leu Arg Arg Arg Cys Phe Cys Thr Arg His Cys
        35                  40                  45

<210> SEQ ID NO 112
<211> LENGTH: 47
<212> TYPE: PRT
<213> ORGANISM: artificial
<220> FEATURE:
<223> OTHER INFORMATION: PgD1

<400> SEQUENCE: 112

Arg Thr Cys Glu Ser Gln Ser His Lys Phe Lys Gly Thr Cys Ala Ser
1               5                   10                  15

Gly Thr Asn Cys Ala Asn Val Cys Lys Thr Glu Gly Phe Pro Gly Gly
            20                  25                  30

Lys Cys Arg Gly Phe Arg Arg Arg Cys Phe Cys Thr Thr His Cys
        35                  40                  45

<210> SEQ ID NO 113
<211> LENGTH: 47
<212> TYPE: PRT
<213> ORGANISM: artificial
<220> FEATURE:
<223> OTHER INFORMATION: VfoD1

<400> SEQUENCE: 113

Arg Thr Cys Glu Ser Gln Ser His Lys Phe Lys Gly Thr Cys Leu Ser
1               5                   10                  15

Glu Thr Asn Cys Ala Ser Val Cys Lys Thr Glu Gly Phe Thr Gly Gly
            20                  25                  30

Asp Cys Arg Gly Leu Arg Arg Arg Cys Phe Cys Thr Arg Asn Cys
        35                  40                  45

<210> SEQ ID NO 114
<211> LENGTH: 47
<212> TYPE: PRT
<213> ORGANISM: artificial
<220> FEATURE:
<223> OTHER INFORMATION: BnD9

<400> SEQUENCE: 114

Arg Thr Cys Glu Ser Gln Ser His Arg Phe Lys Gly Pro Cys Val Ser
1               5                   10                  15

Asp Asn Asn Cys Ala Asn Val Cys His Asn Glu Gly Phe Gly Gly Gly
            20                  25                  30

Lys Cys Arg Gly Leu Arg Arg Arg Cys Phe Cys Thr Arg His Cys
        35                  40                  45

```
<210> SEQ ID NO 115
<211> LENGTH: 47
<212> TYPE: PRT
<213> ORGANISM: artificial
<220> FEATURE:
<223> OTHER INFORMATION: EsD5

<400> SEQUENCE: 115

Arg Thr Cys Glu Ser Lys Ser His Arg Phe Lys Gly Ala Cys Leu Ser
1               5                   10                  15

Glu Thr Asn Cys Lys Asn Val Cys His Asn Glu Gly Phe Arg Gly Gly
            20                  25                  30

Asn Cys Arg Gly Leu Arg Arg Arg Cys Phe Cys Thr Arg Asn Cys
        35                  40                  45

<210> SEQ ID NO 116
<211> LENGTH: 47
<212> TYPE: PRT
<213> ORGANISM: artificial
<220> FEATURE:
<223> OTHER INFORMATION: FvD6

<400> SEQUENCE: 116

Arg Thr Cys Glu Ser Leu Ser His Lys Phe Lys Gly Thr Cys Leu Ser
1               5                   10                  15

Glu Thr Asn Cys Ala Ser Val Cys Lys Thr Glu Gly Phe Ser Gly Gly
            20                  25                  30

Asp Cys Arg Gly Leu Arg Arg Arg Cys Phe Cys Thr Lys His Cys
        35                  40                  45

<210> SEQ ID NO 117
<211> LENGTH: 47
<212> TYPE: PRT
<213> ORGANISM: artificial
<220> FEATURE:
<223> OTHER INFORMATION: JcD2

<400> SEQUENCE: 117

Arg Thr Cys Glu Ser Gln Thr His Lys Phe Lys Gly Thr Cys Leu Ser
1               5                   10                  15

Glu Thr Asn Cys Ala Asn Val Cys Lys Thr Glu Gly Phe Thr Gly Gly
            20                  25                  30

Asp Cys Arg Gly Leu Arg Arg Arg Cys Phe Cys Thr Arg His Cys
        35                  40                  45

<210> SEQ ID NO 118
<211> LENGTH: 47
<212> TYPE: PRT
<213> ORGANISM: artificial
<220> FEATURE:
<223> OTHER INFORMATION: Pa-PDF

<400> SEQUENCE: 118

Arg Thr Cys Leu Ser Gln Ser Arg Lys Phe Lys Gly Ala Cys Leu Ser
1               5                   10                  15

Asp Thr Asn Cys Gly Asn Val Cys Lys Ser Glu Gly Phe Pro Arg Gly
            20                  25                  30

Asp Cys Arg Gly Phe Arg Arg Arg Cys Phe Cys Val Lys His Cys
        35                  40                  45

<210> SEQ ID NO 119
<211> LENGTH: 47
<212> TYPE: PRT
```

<213> ORGANISM: artificial
<220> FEATURE:
<223> OTHER INFORMATION: RcD3

<400> SEQUENCE: 119

```
Arg Thr Cys Glu Ser Gln Ser His Lys Phe Lys Gly Thr Cys Leu Ser
1               5                   10                  15
Thr Thr Asn Cys Ala Asn Ile Cys Lys Thr Glu Gly Phe His Gly Gly
            20                  25                  30
Arg Cys Arg Gly Phe Arg Arg Arg Cys Phe Cys Thr Lys His Cys
        35                  40                  45
```

<210> SEQ ID NO 120
<211> LENGTH: 47
<212> TYPE: PRT
<213> ORGANISM: artificial
<220> FEATURE:
<223> OTHER INFORMATION: SID20

<400> SEQUENCE: 120

```
Arg Thr Cys Glu Ser Gln Ser His His Phe Lys Gly Asn Cys Leu Ser
1               5                   10                  15
Asp Thr Asn Cys Gly Ser Val Cys Arg Thr Glu Gly Phe Thr Gly Gly
            20                  25                  30
Asn Cys Arg Gly Phe Arg Arg Arg Cys Phe Cys Thr Arg Asn Cys
        35                  40                  45
```

<210> SEQ ID NO 121
<211> LENGTH: 47
<212> TYPE: PRT
<213> ORGANISM: artificial
<220> FEATURE:
<223> OTHER INFORMATION: StD13

<400> SEQUENCE: 121

```
Arg Thr Cys Glu Ser Lys Ser His Phe Lys Gly Lys Cys Leu Ser
1               5                   10                  15
Asp Thr Asn Cys Gly Ser Val Cys His Thr Glu Gly Phe Thr Gly Gly
            20                  25                  30
Asn Cys Arg Gly Leu Arg Gln Arg Cys Phe Cys Thr Arg Asn Cys
        35                  40                  45
```

<210> SEQ ID NO 122
<211> LENGTH: 47
<212> TYPE: PRT
<213> ORGANISM: artificial
<220> FEATURE:
<223> OTHER INFORMATION: ScD1

<400> SEQUENCE: 122

```
Arg Thr Cys Glu Ser Gln Ser His Arg Phe Lys Gly Pro Cys Val Ser
1               5                   10                  15
Glu Lys Asn Cys Ala Ser Val Cys Glu Thr Glu Gly Phe Ser Gly Gly
            20                  25                  30
Asp Cys Arg Gly Leu Arg Arg Arg Cys Phe Cys Thr Arg Pro Cys
        35                  40                  45
```

<210> SEQ ID NO 123
<211> LENGTH: 47
<212> TYPE: PRT
<213> ORGANISM: artificial
<220> FEATURE:
<223> OTHER INFORMATION: SID17

<400> SEQUENCE: 123

```
Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Phe Arg Arg Cys Phe Cys Thr Arg Pro Cys
        35                  40                  45
```

<210> SEQ ID NO 124
<211> LENGTH: 47
<212> TYPE: PRT
<213> ORGANISM: artificial
<220> FEATURE:
<223> OTHER INFORMATION: NaD2

<400> SEQUENCE: 124

```
Arg Thr Cys Glu Ser Gln Ser His Arg Phe Lys Gly Pro Cys Ala Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Cys Phe Cys Thr Arg Pro Cys
        35                  40                  45
```

<210> SEQ ID NO 125
<211> LENGTH: 47
<212> TYPE: PRT
<213> ORGANISM: artificial
<220> FEATURE:
<223> OTHER INFORMATION: NtD4

<400> SEQUENCE: 125

```
Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Cys Phe Cys Thr Arg Pro Cys
        35                  40                  45
```

<210> SEQ ID NO 126
<211> LENGTH: 47
<212> TYPE: PRT
<213> ORGANISM: artificial
<220> FEATURE:
<223> OTHER INFORMATION: FST

<400> SEQUENCE: 126

```
Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Leu Leu Arg Arg Cys Leu Cys Thr Lys Pro Cys
        35                  40                  45
```

<210> SEQ ID NO 127
<211> LENGTH: 47
<212> TYPE: PRT
<213> ORGANISM: artificial
<220> FEATURE:
<223> OTHER INFORMATION: NtD3

<400> SEQUENCE: 127

-continued

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Lys Phe Thr Asp Gly
            20                  25                  30

His Cys Ser Lys Leu Leu Arg Arg Cys Leu Cys Ala Lys Pro Cys
        35                  40                  45

<210> SEQ ID NO 128
<211> LENGTH: 47
<212> TYPE: PRT
<213> ORGANISM: artificial
<220> FEATURE:
<223> OTHER INFORMATION: NeThio2

<400> SEQUENCE: 128

Lys Asp Cys Lys Thr Glu Ser Asn Thr Phe Pro Gly Ile Cys Ile Thr
1               5                   10                  15

Lys Pro Pro Cys Arg Lys Ala Cys Ile Lys Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 129
<211> LENGTH: 47
<212> TYPE: PRT
<213> ORGANISM: artificial
<220> FEATURE:
<223> OTHER INFORMATION: SL14B1

<400> SEQUENCE: 129

Lys Asp Cys Lys Thr Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 130
<211> LENGTH: 47
<212> TYPE: PRT
<213> ORGANISM: artificial
<220> FEATURE:
<223> OTHER INFORMATION: SL78B

<400> SEQUENCE: 130

Lys Asp Cys Lys Thr Glu Ser Asn Thr Phe Pro Gly Ile Cys Val Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 131
<211> LENGTH: 47
<212> TYPE: PRT
<213> ORGANISM: artificial
<220> FEATURE:
<223> OTHER INFORMATION: NeD1

<400> SEQUENCE: 131

Lys Asp Cys Lys Arg Glu Ser Asn Thr Phe Pro Gly Ile Cys Ile Thr
1               5                   10                  15

Lys Pro Pro Cys Arg Lys Ala Cys Ile Lys Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 132
<211> LENGTH: 47
<212> TYPE: PRT
<213> ORGANISM: artificial
<220> FEATURE:
<223> OTHER INFORMATION: SL137

<400> SEQUENCE: 132

Lys Asp Cys Lys Thr Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Lys Cys Leu Cys Thr Lys Pro Cys
        35                  40                  45

<210> SEQ ID NO 133
<211> LENGTH: 47
<212> TYPE: PRT
<213> ORGANISM: artificial
<220> FEATURE:
<223> OTHER INFORMATION: SL549

<400> SEQUENCE: 133

Lys Asp Cys Lys Arg Glu Ser Asn Thr Phe Pro Gly Ile Cys Leu Thr
1               5                   10                  15

Lys Pro Pro Cys Arg Lys Ala Cys Ile Lys Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 134
<211> LENGTH: 47
<212> TYPE: PRT
<213> ORGANISM: artificial
<220> FEATURE:
<223> OTHER INFORMATION: SL445

<400> SEQUENCE: 134

Lys Asp Cys Arg Arg Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 135
<211> LENGTH: 47
<212> TYPE: PRT
<213> ORGANISM: artificial
<220> FEATURE:
<223> OTHER INFORMATION: SL99

<400> SEQUENCE: 135

Arg Glu Cys Lys Ala Glu Ser Asn Thr Phe Thr Gly Ile Cys Ile Ala
1               5                   10                  15

Lys Pro Pro Cys Arg Lys Val Cys Ile Arg Glu Lys Phe Thr Asp Gly
            20                  25                  30

His Cys Ser Lys Val Leu Arg Arg Cys Leu Cys Thr Lys Pro Cys
            35                  40                  45

<210> SEQ ID NO 136
<211> LENGTH: 47
<212> TYPE: PRT
<213> ORGANISM: artificial
<220> FEATURE:
<223> OTHER INFORMATION: SL446

<400> SEQUENCE: 136

Lys Asp Cys Lys Arg Glu Ser Asn Thr Phe Pro Gly Ile Cys Ile Thr
1               5                   10                  15

Lys Pro Pro Cys Arg Lys Ala Cys Ile Arg Glu Lys Phe Ala Asp Asp
            20                  25                  30

His Cys Ser Lys Ile Leu Arg Arg Cys Leu Cys Thr Lys Pro Cys
            35                  40                  45

<210> SEQ ID NO 137
<211> LENGTH: 47
<212> TYPE: PRT
<213> ORGANISM: artificial
<220> FEATURE:
<223> OTHER INFORMATION: NpD1

<400> SEQUENCE: 137

Ser Thr Cys Lys Ala Glu Ser Asn Thr Phe Pro Gly Leu Cys Ile Thr
1               5                   10                  15

Lys Pro Pro Cys Arg Lys Ala Cys Leu Ser Glu Lys Phe Thr Asp Gly
            20                  25                  30

Lys Cys Ser Lys Ile Leu Arg Arg Cys Ile Cys Tyr Lys Pro Cys
            35                  40                  45

<210> SEQ ID NO 138
<211> LENGTH: 47
<212> TYPE: PRT
<213> ORGANISM: artificial
<220> FEATURE:
<223> OTHER INFORMATION: SL548

<400> SEQUENCE: 138

Lys Asp Cys Lys Arg Glu Ser Asn Thr Phe Pro Gly Ile Cys Val Thr
1               5                   10                  15

Lys Leu Pro Cys Arg Gln Ala Cys Ile Arg Glu Lys Phe Thr Asp Gly
            20                  25                  30

His Cys Ser Lys Ile Leu Arg Arg Cys Leu Cys Thr Lys Pro Cys
            35                  40                  45

<210> SEQ ID NO 139
<211> LENGTH: 47
<212> TYPE: PRT
<213> ORGANISM: artificial
<220> FEATURE:
<223> OTHER INFORMATION: SL97

<400> SEQUENCE: 139

Arg Glu Cys Lys Ala Glu Ser Asn Thr Phe Thr Gly Met Cys Ile Ala
1               5                   10                  15

Lys Pro Pro Cys Arg Lys Val Cys Ile Arg Glu Lys Phe Thr Asp Gly
            20                  25                  30

His Cys Ser Lys Val Leu Arg Arg Cys Leu Cys Thr Lys Pro Cys
            35                  40                  45

```
<210> SEQ ID NO 140
<211> LENGTH: 47
<212> TYPE: PRT
<213> ORGANISM: artificial
<220> FEATURE:
<223> OTHER INFORMATION: SL16

<400> SEQUENCE: 140

Arg Gln Cys Lys Ala Glu Ser Asn Thr Phe Thr Gly Ile Cys Ile Ala
1               5                   10                  15

Lys Pro Pro Cys Arg Lys Ala Cys Ile Arg Glu Lys Phe Thr Asp Gly
            20                  25                  30

His Cys Ser Lys Val Leu Arg Lys Cys Leu Cys Thr Lys Pro Cys
        35                  40                  45

<210> SEQ ID NO 141
<211> LENGTH: 47
<212> TYPE: PRT
<213> ORGANISM: artificial
<220> FEATURE:
<223> OTHER INFORMATION: SL12

<400> SEQUENCE: 141

Arg Gln Cys Lys Ala Glu Ser Asn Thr Phe Thr Gly Ile Cys Ile Ala
1               5                   10                  15

Lys Pro Pro Cys Arg Lys Ala Cys Ile Arg Glu Lys Phe Thr Asp Gly
            20                  25                  30

His Cys Ser Lys Val Leu Arg Arg Cys Leu Cys Thr Lys Lys Cys
        35                  40                  45

<210> SEQ ID NO 142
<211> LENGTH: 47
<212> TYPE: PRT
<213> ORGANISM: artificial
<220> FEATURE:
<223> OTHER INFORMATION: SL543

<400> SEQUENCE: 142

Lys Asp Cys Lys Arg Glu Ser Asn Thr Phe Pro Gly Ile Cys Val Thr
1               5                   10                  15

Lys Leu Pro Cys Arg Gln Ala Cys Ile Arg Glu Lys Phe Thr Asp Gly
            20                  25                  30

His Cys Ser Lys Ile Leu Arg Lys Cys Leu Cys Thr Lys Pro Cys
        35                  40                  45

<210> SEQ ID NO 143
<211> LENGTH: 47
<212> TYPE: PRT
<213> ORGANISM: artificial
<220> FEATURE:
<223> OTHER INFORMATION: SL14

<400> SEQUENCE: 143

Arg Gln Cys Lys Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
            20                  25                  30

His Cys Ser Lys Val Leu Arg Arg Cys Leu Cys Thr Lys Arg Cys
        35                  40                  45

<210> SEQ ID NO 144
<211> LENGTH: 47
```

```
<212> TYPE: PRT
<213> ORGANISM: artificial
<220> FEATURE:
<223> OTHER INFORMATION: SL171

<400> SEQUENCE: 144

Arg Gln Cys Arg Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
            20                  25                  30

His Cys Ser Lys Val Leu Arg Arg Cys Leu Cys Thr Lys Arg Cys
        35                  40                  45

<210> SEQ ID NO 145
<211> LENGTH: 50
<212> TYPE: PRT
<213> ORGANISM: artificial
<220> FEATURE:
<223> OTHER INFORMATION: Vm-PDF

<400> SEQUENCE: 145

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Gly Gly Lys His Met Cys Phe Cys Tyr Phe
        35                  40                  45

Asn Cys
    50

<210> SEQ ID NO 146
<211> LENGTH: 50
<212> TYPE: PRT
<213> ORGANISM: artificial
<220> FEATURE:
<223> OTHER INFORMATION: VmD1

<400> SEQUENCE: 146

Glu Leu Cys Glu Arg Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Gly Gly Lys His Met Cys Phe Cys Tyr Phe
        35                  40                  45

Asn Cys
    50

<210> SEQ ID NO 147
<211> LENGTH: 50
<212> TYPE: PRT
<213> ORGANISM: artificial
<220> FEATURE:
<223> OTHER INFORMATION: Ds-PDF

<400> SEQUENCE: 147

Ala Leu Cys Glu Lys Ala Ser Lys Thr Trp Ser Gly Asn Cys Gly Asn
1               5                   10                  15

Thr Gly His Cys Asp Asp Gln Cys Lys Ser Trp Glu Thr Ala Ala His
            20                  25                  30

Gly Ala Cys His Val Arg Gly Gly Lys His Met Cys Phe Cys Tyr Phe
        35                  40                  45
```

-continued

Asn Cys
    50

<210> SEQ ID NO 148
<211> LENGTH: 50
<212> TYPE: PRT
<213> ORGANISM: artificial
<220> FEATURE:
<223> OTHER INFORMATION: Hs-PDF

<400> SEQUENCE: 148

Glu Leu Cys Glu Lys Ala Ser Lys Thr Trp Ser Gly Lys Cys Gly Asn
1               5                   10                  15

Thr Arg His Cys Asp Asp Gln Cys Lys Ser Trp Glu Gly Ala Ala His
            20                  25                  30

Gly Ala Cys His Val Arg Gly Gly Lys His Met Cys Phe Cys Tyr Phe
        35                  40                  45

Asn Cys
    50

<210> SEQ ID NO 149
<211> LENGTH: 50
<212> TYPE: PRT
<213> ORGANISM: artificial
<220> FEATURE:
<223> OTHER INFORMATION: Pa-PDF

<400> SEQUENCE: 149

Glu Leu Cys Glu Lys Ala Ser Lys Thr Trp Ser Gly Asn Cys Gly Asn
1               5                   10                  15

Thr Arg His Cys Asp Asp Gln Cys Lys Ser Trp Glu Gly Ala Ala His
            20                  25                  30

Gly Ala Cys His Val Arg Gly Gly Lys His Met Cys Phe Cys Tyr Phe
        35                  40                  45

Gln Cys
    50

<210> SEQ ID NO 150
<211> LENGTH: 50
<212> TYPE: PRT
<213> ORGANISM: artificial
<220> FEATURE:
<223> OTHER INFORMATION: HaD2

<400> SEQUENCE: 150

Glu Leu Cys Glu Lys Ala Ser Gln Thr Trp Ser Gly Thr Cys Gly Lys
1               5                   10                  15

Thr Lys His Cys Asp Asp Gln Cys Lys Ser Trp Glu Gly Ala Ala His
            20                  25                  30

Gly Ala Cys His Val Arg Asp Gly Lys His Met Cys Phe Cys Tyr Phe
        35                  40                  45

Asn Cys
    50

<210> SEQ ID NO 151
<211> LENGTH: 51
<212> TYPE: PRT
<213> ORGANISM: artificial
<220> FEATURE:
<223> OTHER INFORMATION: EprD1

<400> SEQUENCE: 151

```
Glu Leu Cys Glu Lys Ala Ser Gln Thr Trp Ser Gly Thr Cys Arg Ile
1               5                   10                  15

Thr Ser His Cys Asp Asn Gln Cys Lys Ser Trp Glu Gly Ala Ala His
            20                  25                  30

Gly Ala Cys His Val Arg Gly Gly Lys His Met Cys Phe Cys Tyr Phe
            35                  40                  45

Ser His Cys
    50

<210> SEQ ID NO 152
<211> LENGTH: 50
<212> TYPE: PRT
<213> ORGANISM: artificial
<220> FEATURE:
<223> OTHER INFORMATION: PpeD5

<400> SEQUENCE: 152

Arg Leu Cys Glu Arg Ala Ser Leu Thr Trp Ser Gly Asn Cys Gly Asn
1               5                   10                  15

Thr Ala His Cys Asp Asn Gln Cys Arg Ser Trp Glu His Ala Gln His
            20                  25                  30

Gly Ala Cys His Val Arg Gly Gly Lys His Met Cys Phe Cys Tyr Phe
            35                  40                  45

Asn Cys
    50
```

METHOD OF TREATMENT

FILING DATA

This application is associated with and claims priority from U.S. Provisional Patent Application No. 62/066,808, filed on 21 Oct. 2014, entitled "A method of treatment", the entire contents of which, are incorporated herein by reference.

REFERENCE TO SEQUENCE LISTING SUBMITTED VIA EFS-WEB

This application includes an electronically submitted sequence listing in .txt format. The .txt files contains a sequence listing "35233519 ST25.txt" created on Dec. 22, 2016 of 6K bytes in size. The sequence listings contained in this .txt file is part of the specification and is hereby incorporated by reference herein in its entirety.

STATEMENT REGARDING SEQUENCE LISTINGS

The instant application contains a Sequence Listing which has been submitted in ASCII format ("the computer readable form") via EFS-Web and is hereby incorporated by reference in its entirety. Said ASCII copy, created on May 27, 2014, is named DAVIP001US01_SEQLIST_5-27-2015.txt and is 3,000,000 bytes in size. The sequence listing information recorded in the computer readable form is identical to the written paper sequence listing."

BACKGROUND

Field

The present disclosure relates to the control of fungal infection of horn-like envelopes covering dorsal and terminal phalanges in humans and animals and related cerebral protrusions in animals as well as keratin comprising material on surfaces of humans and animals. Agents and natural and synthetic formulations and extracts useful for the control of fungal infection of these envelopes and related protrusions and keratin comprising material are also encompassed by the subject disclosure. In an embodiment, the present disclosure teaches the treatment of fungal infection of nails and in particular onychomycosis in humans.

Description of Related Art

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Fungal infection including infestation can lead to significant health issues in humans and animals.

Although chemical fungicides have been successful in human and veterinary medicine, there is a range of environmental and regulatory concerns with the continued use of chemical agents to control fungal infection. The increasing use of these agents is also providing selective pressure for emergence of resistance in fungal species. There is clearly a need to develop alternative mechanisms of controlling infection in humans and animals by fungal pathogens.

A particularly troublesome condition is onychomycosis, also known as dermatophytic onychomycosis and tinea ungium (Rapini et al. (2007) *Dermatology*: 2-volume set, St. Louis: Mosby). This is a fungal infection of the nail and other horn-like envelopes covering dorsal and terminal phalanges in humans and animals. In particular, it is an infection of the toenail or fingernail involving any component of the nail unit including the matrix, bed or plate. The disease in humans is not uncommon but can be difficult to treat since the infecting fungus is embedded within and underneath the nail. While not life threatening, onychomycosis can cause pain, discomfort, disfigurement and produce both physical and psychological damage. The effects of onychomycosis are widespread and have a significant impact of the quality of life.

The major pathogens that cause onychomycosis are the dermatophytes *Tricophyton rubrum* and *Trichophyton mentagrophytes*, with *T. rubrum* accounting for 90% of cases (Sotiriou et al. (2010) *Acta Derm-Venereol* 9(2):216-217).

The treatment of onychomycosis depends on the clinical subtype, the number of affected nails and the severity of nail involvement. While oral drugs have been most effective, there are a number of factors that prevent their use. Side effects, including hepatotoxicity associated with systemic exposure to most oral antifungal medications, make oral medications unappealing. Furthermore, the elderly are a large demographic that suffer from onychomycosis and unwanted drug-drug interactions due to frequent use of concomitant medications preclude the use of oral medications. This highlights the importance for the development of topical therapies to treat onychomycosis. Most treatments involve either topical or oral antifungal formulations (Westerberg et al. (2013) *American Family Physician* 88(11):762-770). Oral medicaments include terbinafine, itraconazole and fluconazole (Westerberg et al. (2013) supra). These treatments only cure infections in 14-38% of cases and come with a high risk of liver damage. Topical medicaments include ciclopirox, clotrimazole, amorolfine, efinaconazole, tavaborole and butenafine. These treatments have cure rates of between 5 and 17% and must be applied every day for at least 48-weeks. These low cure rates are a result of very poor permeation of the active ingredients through nails as well as fungistatic modes of action which only inhibit fungal growth rather than killing the fungal cells, allowing a reservoir of fungus to persist and re-infect the nail. In addition, the long treatment regimens result in non-compliance by many patients. None of these treatments is totally effective and the condition can persist for many years.

For a topical onychomycosis treatment to reach the site of infection the antifungal agent must be able to permeate the nail. Studies of permeation of the human nail plate and of keratin membranes from bovine hooves by several model antimycotic drugs showed that nail permeability decreases as molecular weight increases (Mertin and Lippold (1997) *J Pharm Pharmacol* 49:866-872; Kobayashi et al (2004) *Eur J Pharm Sci* 21:471-477). Each of the model drugs tested had a molecular weight of less than 1000. These studies suggest that a molecule with a MW>5000 would not be able to permeate the nail.

Another problematic condition is fungal infection of hair and other keratin comprising material including the interface between the hair and hair follicle. This condition is sometimes known as tinea capitis or scalp ringworm. Treatment can be in the form of oral medicaments including griseofulvin, terbinafine and itraconazole. Topical treatments include shampoos containing antifungal agents such as ketoconazole, cyclopirox, piroctone and zinc pyrithione. Fungal infections of the scalp and skin can also cause irritation and flaking of the skin leading to conditions such as seborrheic dermatitis and dandruff. Shampoos containing antifungal agents can be used to treat dandruff caused by fungal infection.

Plant defensins are small (45-54 amino acids), basic proteins with four to five disulfide bonds (Janssen et al. (2003) *Biochemistry* 42(27):8214-8222). They share a common disulfide bonding pattern and a common structural fold, in which a triple-stranded, antiparallel β-sheet is tethered to an α-helix by three disulfide bonds, forming a cysteine-stabilized αβ motif. A fourth disulfide bond also joins the N- and C-termini leading to an extremely stable structure. Plant defensins can have many biological functions, including anti-bacterial activity, protein synthesis inhibition, α-amylase and protease inhibition, roles inflower development and pollen sensing and antifungal activity (Colilla et al. (1990) *FEBS Lett* 270(1-2):191-194; Bloch and Richardson (1991) *FEBS Lett* 279(1):101-104; van der Weerden et al (2013) *Fungal Biol Rev* 26:121-131).

The structure of defensins consists of seven 'loops', defined as the regions between cysteine residues. Loop 1 encompasses the first β-strand (1A) as well as most of the flexible region that connects this β-strand to the α-helix (1B) between the first two invariant cysteine residues. Loops 2, 3 and the beginning of 4 (4A) make up the α-helix, while the remaining loops (4B-7) make up β-strands 2 and 3 and the flexible region that connects them (β-hairpin region) [van der Weerden et al. (2013) *Cell Mol Life Sci* 70 (19): 3545-3570]. Loop 5 of plant defensins is known to be essential for antifungal activity and an important determinant for the mechanism of action of these proteins (Sagaram et al., (2011) *PLoS One* 6.4: e18550).

Plant defensins generally share eight completely conserved cysteine residues. These residues are commonly referred to as "invariant cysteine residues", as their presence, location and connectivity are conserved amongst defensins. Based on sequence similarity, plant defensins can be categorized into different groups. Within each group, sequence homology is relatively high whereas inter-group amino acid similarity is low (van der Weerden et al. (2013) *Fungal Biol Rev* 26:121-131). Plant defensins belonging to different groups have generally different biological activities or different mechanisms of action for the same biological activity. For example, plant defensins belonging to the group of the radish peptide RsAFP2 inhibit fungal growth by binding to sphingolipids in the cell wall (Thevissen et al. (2012) *Mol Microbiol* 84(1):166-180). In contrast, plant defensins belonging to the group of the *Nicotiana* defensin NaD1 inhibit fungal growth by entering the fungal cell and inducing production of reactive oxygen species (ROS) leading to cell lysis (Hayes et al. (2013) *Antimicrob Agents Ch* 57(8)3667-3675).

There are two major classes of plant defensins. Class I defensins consist of an endoplasmic reticulum (ER) signal sequence followed by a mature defensin domain. Class II defensins are produced as larger precursors with C-terminal pro-domains or pro-peptides (CTPPs) of about 33 amino acids. Most of the Class II defensins identified to date have been found in Solanaceous plant species.

There is a need to develop protocols to more effectively manage fungal infection in humans and animals and in particular, onychomycosis in humans, for which until the advent of the present invention, no safe and effective treatments were available. Whilst some defensins have antifungal properties, their activities across different fungal pathogens vary significantly and a majority of demonstrated activity has been toward plant fungal pathogens. In addition, their size (MW>5000 Da) would appear to limit their permeability into the nails.

SUMMARY

Amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure is predicated in part on the surprising determination that, despite their size, some defensins are able to effectively penetrate nails and treat fungal infection. In addition, despite evolving to target plant fungal pathogens, some plant defensins have potent activity against the fungal pathogens that cause onychomycosis such as *Trichophyton rubrum* with no off-target activity on mammalian cells. More surprisingly, some plant defensins have a fungicidal mode of action enabling them to kill fungal cells on contact. The present disclosure teaches, therefore, a method for inhibiting infection by a fungal pathogen in or on a horn-like envelope covering dorsal and terminal phalanges or a related cerebral protrusion in a subject or keratin comprising material on the subject, the method comprising contacting the envelope or protrusion or keratin comprising material with an effective amount of a plant defensin or a functional natural or synthetic derivative or variant thereof, the plant defensin, derivative or variant having the consensus amino acid sequence as set forth in SEQ ID NO:24. In an embodiment, the defensin is selected from the group consisting of HXL008 (SEQ ID NO:1), HXL035 (SEQ ID NO:2) and HXL036 (SEQ ID NO:3). Other defensins contemplated herein are selected from the group consisting of HXL001 (SEQ ID NO:4), HXL002 (SEQ ID NO:5), HXL003 (SEQ ID NO:6), HXL004 (SEQ ID NO:7), HXL005 (SEQ ID NO:8), HXL009 (SEQ ID NO:9), HXL012 (SEQ ID NO:10), HXL013 (SEQ ID NO:11), HXL015 (SEQ ID NO:12), HXL032 (SEQ ID NO:13), HXL033 (SEQ ID NO:14), HXL034 (SEQ ID NO:15), NsD1 (SEQ ID NO:16), NsD2 (SEQ ID NO:17), NaD1 (SEQ ID NO:18), NoD173 (SEQ ID NO:19) DmAMP1 (SEQ ID NO:20), HXP4 (SEQ ID NO:21); HXP34 (SEQ ID NO:22), HXP35 (SEQ ID NO:23), and any of the above with an added N-terminal alanine residue (SEQ ID NO:25 through 47, respectively), and a plant defensin having at least about 80% amino acid sequence similarity to any one of SEQ ID NO:1 through 47 after optimal alignment. The defensin contacts generally by topical application the horn-like envelope or keratin comprising material for a time and under conditions sufficient to eradicate or otherwise control fungal growth. The envelope includes finger and toe nails as well as claws, hooves and horns. In an embodiment, the present disclosure enables a method for the treatment of onychomycosis or a related condition in a subject, the method comprising administering to the subject an effective amount of a plant defensin or a functional natural or synthetic derivative or variant thereof, the plant defensin or variant having the consensus amino acid sequence as set forth in SEQ ID NO:24. In an embodiment, the defensin is selected from the group consisting of SEQ ID NO:1 through 3 or any one of SEQ ID NO:4 through 47 or a defensin having at least about 80% similarity to any one of SEQ ID NO:1 through 47. In a particular embodiment, the defensin is any one of HXL008 (SEQ ID NO:1), HXL035 (SEQ ID NO:2) or HXL036 (SEQ ID NO:3) or a functional natural or synthetic variant thereof including the defensin comprising N-terminal alanine residue (SEQ ID NO:25 though 27 respectively)

In another embodiment, the keratin comprising material is hair or fur. In this embodiment, the present disclosure enables a method for the treatment of fungal infection of hair or fur in a subject, the method comprising administering to the subject an effective amount of a plant defensin or a functional natural or synthetic derivative or variant thereof, the plant defensin or variant selected having the consensus amino acid sequence as set forth in SEQ ID NO:24. In an embodiment, the defensin is selected from the group consisting of SEQ ID NO:1 through 3 or any one of SEQ ID NO:4 through 47 or a defensin having at least about 80% similarity to any one of SEQ ID NO:1 through 47. In a particular embodiment the defensin is selected from SEQ ID NO:1, SEQ ID NO:2 or SEQ ID NO:3 or a functional natural or synthetic variant thereof including the defensin comprising N-terminal alanine residue (SEQ ID 25 though 27 respectively). In another embodiment, the keratin comprising material is skin. In this embodiment, the present disclosure enables a method for the treatment of fungal infection of skin in a subject, the method comprising administering to the subject an effective amount of a plant defensin or a functional natural or synthetic derivative or variant thereof, the plant defensin or variant selected having the consensus amino acid sequence as set forth in SEQ ID NO:24. In an embodiment, the defensin is selected from the group consisting of SEQ ID NO:1 through 3 or any one of SEQ ID NO:4 through 47 or a defensin having at least about 80% similarity to any one of SEQ ID NO:1 through 47. In a particular embodiment the defensin is defined by SEQ ID NO:1, SEQ ID NO:2 or SEQ ID NO:3 or a functional natural or synthetic derivative or variant thereof including the defensin comprising N-terminal alanine residue (SEQ ID 25, though 27 respectively).

The defensins contemplated for use in the treatment protocol are listed in Table 2 as well as defensins having at least 80% similarity to any one of the defensins listed in Table 2 after optimal alignment. For the sake of brevity, reference to "SEQ ID NO:1 through 47" hereinafter includes defensins having at least 80% similarity to any one of SEQ ID NO:1 through 47. In an embodiment, the defensin is a permeabilizing defensin or a functional natural or synthetic derivative or variant thereof. Examples of synthetic variants include where a Loop1B from a Class I defensin replaces the Loop1B from the Solanaceous Class II defensin. These are HXP4, HXP34, and HXP35. Other variants or derivatives include a defensin listed in Table 2 or having at least 80% similarity to a defensin listed in Table 2 wherein the defensin comprises an alanine residue at its N-terminus (i.e., SEQ ID NO:25 through 47). The addition of an alanine at the N-terminus of a defensin allows the peptide to be produced recombinantly in the *Pichia pastoris* expression system without the need for the STE13 protease site. The STE13 site normally allows for efficient processing of the α-mating factor secretion signal by KEX2. However, under high expression loads the STE13 protease cleavage can be inefficient leading to Glu-Ala repeats remaining on the N-terminus of the peptide. The additional negative charge conferred by these repeats can be detrimental to the activity of plant defensins. The STE13 protease site can be replaced with an alanine to prevent incomplete processing (Cabral et al., (2003) *Protein Expres Purif* 31(1):115-122). The presence of an N-terminal alanine can also decrease the ability of the defensin to lyse red blood cells (WO2011/16074).

In an embodiment, a defensin listed in Table 2 (SEQ ID NO:1 through 47) is modified to enhance the stability of the peptide. In a further embodiment, this is achieved by replacing amino acids that are susceptible to deamidation such as asparagine and glutamine, or amino acids that are susceptible to isomerization such as aspartic acid, with amino acids that are not susceptible to modifications. In a particular embodiment, the defensins HXL008, HXL035 or HXL036 are modified at positions 18, 36 or 42.

In an embodiment, a defensin listed in Table 2 (SEQ ID NO:1 through 47) is modified to increase the positive charge of the peptide. Positive charge is known to be important for the activity of antimicrobial peptides, including plant defensins (Sagaram et al., (2011) *PLoS One* 6.4: e18550). In an embodiment the increase in positive charge is achieved by replacement of a negatively charged residue such as glutamatic acid or aspartic acid with a neutral amino acid. In an embodiment, the neutral amino acid is an alanine or a glycine. In another embodiment, the increase in positive charge is achieved by replacing a neutral amino acid with a positively charged residue such as lysine or arginine.

Conservative amino acid changes are also contemplated herein.

In an embodiment, the treatment includes a defensin in combination with a non-defensin peptide, a proteinase inhibitor, another defensin or a proteinaceous or non-proteinaceous (i.e., chemical) fungicide.

The fungal pathogen is one which contributes to onychomycosis or related condition in finger or toe nails, claws, hooves or horns in a subject.

Reference to a "nail" includes any horn-like envelope covering dorsal and terminal phalanges in humans and animals and related cerebral protrusions (i.e., horns) in animals. An "onychomycosis-related condition" is an infection in surrounding cuticle of the nail of a human, non-human primate or animal or an infection in or on a claw, hoof or horn-like protrusion in an animal. An example of a related condition is *tinea*.

Fungal pathogens include dermatophytes, yeasts and non-dermatophytic molds. Dermatophytes encompasses *Trichophyton* species, including *Trichophyton rubrum, Trichophyton mentagrophytes, Trichophyton interdigitale, Trichophyton violaceum, Trichophyton tonsurans* and *Trichophyton soudanense, Microsporum fulvum, Epidermophyton floccosum* and *Microsporum gypseum*. Yeasts encompass *Candida* species including *Candida albicans* and *Candida glabrata*.

In an embodiment, the defensin is topically applied to the infected region and penetrates the nail or horn-like structure to accumulate at the site of infection. It is surprisingly determined that some defensins such as but not limited to HXL008 (SEQ ID NO:1), HXL035 (SEQ ID NO:2) and HXL036 (SEQ ID NO:3), have a high degree of penetrability through nails and are potent fungicidal inhibitors of dermatophyte pathogens, and non-dermatophyte molds thus making them very effective in the treatment of conditions such as onychomycosis. In an embodiment the defensins have no off-target effects on mammalian or bacterial cells. Activity against mammalian cells will increase the likelihood of dermal irritation and other side effects. Activity against bacterial cells can disrupt the natural, beneficial microflora in the area. It is well known that the native microflora play an important role in preventing fungal infections (Reid et al., (2011) *Nature Reviews Microbiology* 9: 27-38).

Further taught herein is a formulation or extract including a plant extract or yeast extract (e.g. an extract of *Pichia* genetically modified to produce a defensin) comprising a plant defensin selected from SEQ ID NO:1 through 47. The formulation or extract may further comprise another active agent or a combination of formulations or extracts wherein at least one formulation or extract comprises a defensin as defined herein which are admixed prior to use or used sequentially in either order. The plant defensins or extracts comprising same as defined herein may be used such as in the form of herbal formulations and natural body or nail washes and shampoos including drenches. The defensin is generally formulated to permit penetration into the target site (e.g. nail or skin or hair or fur strand).

Enabled herein is a use of a plant defensin as defined by SEQ ID NO:1 through 47 in the manufacture of a medicament for the treatment or prophylaxis of fungal infection of a horn-like envelope covering dorsal and terminal phalanges or related cerebral protrusions in a subject. Also taught herein is a plant defensin as defined by SEQ ID NO:1 through 47 for use in the treatment or prophylaxis of fungal infection of a horn-like envelope covering dorsal and terminal phalanges or related cerebral protrusions in a subject. Enabled herein is a use of a plant defensin as defined by SEQ ID NO:1 through 47 in the manufacture of a medicament for the treatment or prophylaxis of fungal infection of keratin comprising material on a subject. Also taught herein is a plant defensin as defined by SEQ ID NOs:1 through 47. In a particular embodiment, the defensin is defined by the consensus sequence SEQ ID NO:24 or a functional natural or synthetic variant thereof. Examples include defensins defined by SEQ ID NO:1, SEQ ID NO:2 and SEQ ID NO:3 as well as the defensin comprising N-terminal alanine residue (SEQ ID 25, through 27 respectively).

In an embodiment, the fungal infection leads to onychomycosis or a related condition.

Generally, the subject treated is a human with onychomycosis or a related condition of finger nails or toe nails. However, the present invention also relates to treating animal finger and toe nails, claws and, where applicable, horns, such as in non-human primates, farm animals and horned animals.

Further contemplated herein is an isolated microorganism engineered to express a defensin as defined herein for use in the manufacture of compositions comprising the microorganisms. An example of a microorganism is *Pichia*. Such compositions are useful in the treatment of humans and animals. Alternatively, the defensin is provided as a cell extract including a plant extract or microbial extract.

A kit for treating a fungal infection in compartmental form comprising a plant defensin or a functional natural or synthetic derivative or variant thereof, the plant defensin or variant selected from the list consisting of SEQ ID NO:1 through 47, is also taught herein. In an optional embodiment, another compartment comprises a second active agent and optionally separably in a further compartment or together in an existing compartment, a pharmaceutically or veterinarily acceptable diluent, carrier or excipient. In an embodiment, the defensin is defined by the consensus amino acid sequence set forth in SEQ ID NO:24. Examples include HXL008 (SEQ ID NO:1), HXL035 (SEQ ID NO:2) and HXL036 (SEQ ID NO:3).

In an embodiment, a defensin contemplated for use herein may or may not comprise an N-terminal alanine residue. This is particularly the case with some recombinant defensins which comprise the N-terminal alanine residue. Encompassed by the definition of a "defensin" herein is any of SEQ ID NO:1 though 23 with an N-terminal alanine, i.e. SEQ ID NO:25 through 47. The consensus amino acid sequence, SEQ ID NO:24, has an optional-terminal alanine residue.

TABLE 1

Summary of sequence identifiers

| SEQUENCE ID NO: | DESCRIPTION |
|---|---|
| 1 | Amino acid sequence of HXL008 protein |
| 2 | Amino acid sequence of HXL035 protein |
| 3 | Amino acid sequence of HXL036 protein |
| 4 | Amino acid sequence of HXL001 protein |
| 5 | Amino acid sequence of HXL002 protein |
| 6 | Amino acid sequence of HXL003 protein |
| 7 | Amino acid sequence of HXL004 protein |
| 8 | Amino acid sequence of HXL005 protein |
| 9 | Amino acid sequence of HXL009 protein |
| 10 | Amino acid sequence of HXL012 protein |
| 11 | Amino acid sequence of HXL013 protein |
| 12 | Amino acid sequence of HXL015 protein |
| 13 | Amino acid sequence of HXL032 protein |
| 14 | Amino acid sequence of HXL033 protein |
| 15 | Amino acid sequence of HXL034 protein |
| 16 | Amino acid sequence of NsD1 protein |
| 17 | Amino acid sequence of NsD2 protein |
| 18 | Amino acid sequence of NaD1 protein |
| 19 | Amino acid sequence of NoD173 protein |
| 20 | Amino acid sequence of DmAMP1 protein |
| 21 | Amino acid sequence of HXP4 protein |
| 22 | Amino acid sequence of HXP34 protein |
| 23 | Amino acid sequence of HXP35 protein |
| 24 | Consensus sequence |
| 25 | Amino acid sequence of HXL008 protein + N-terminal alanine |
| 26 | Amino acid sequence of HXL035 protein + N-terminal alanine |
| 27 | Amino acid sequence of HXL036 protein + N-terminal alanine |
| 28 | Amino acid sequence of HXL001 protein + N-terminal alanine |
| 29 | Amino acid sequence of HXL002 protein + N-terminal alanine |
| 30 | Amino acid sequence of HXL003 protein + N-terminal alanine |
| 31 | Amino acid sequence of HXL004 protein + N-terminal alanine |
| 32 | Amino acid sequence of HXL005 protein + N-terminal alanine |
| 33 | Amino acid sequence of HXL009 protein + N-terminal alanine |
| 34 | Amino acid sequence of HXL012 protein + N-terminal alanine |
| 35 | Amino acid sequence of HXL013 protein + N-terminal alanine |
| 36 | Amino acid sequence of HXL015 protein + N-terminal alanine |
| 37 | Amino acid sequence of HXL032 protein + N-terminal alanine |
| 38 | Amino acid sequence of HXL033 protein + N-terminal alanine |
| 39 | Amino acid sequence of HXL034 protein + N-terminal alanine |
| 40 | Amino acid sequence of NsD1 protein + N-terminal alanine |
| 41 | Amino acid sequence of NsD2 protein + N-terminal alanine |
| 42 | Amino acid sequence of NaD1 protein + N-terminal alanine |
| 43 | Amino acid sequence of NoD173 protein + N-terminal alanine |
| 44 | Amino acid sequence of DmAMP1 protein + N-terminal alanine |
| 45 | Amino acid sequence of HXP4 protein + N-terminal alanine |
| 46 | Amino acid sequence of HXP34 protein + N-terminal alanine |
| 47 | Amino acid sequence of HXP35 protein + N-terminal alanine |

Amino acid sequences for HXL proteins are recited in U.S. Pat. No. 6,911,577 and related patent family members.

TABLE 2

Examples of plant defensins

| Peptide | Source | Type (Class I, Class II or variant) | Reference |
|---|---|---|---|
| HXL008 | Picramnia pentandra | Class I | SEQ ID NO: 1 |
| HXL035 | Picramnia pentandra | Class I | SEQ ID NO: 2 |
| HXL036 | Picramnia pentandra | Class I | SEQ ID NO: 3 |
| HXL001 | Zea mays | Class I | SEQ ID NO: 4 |
| HXL002 | Triticum aestivum | Class I | SEQ ID NO: 5 |
| HXL003 | Triticum aestivum | Class I | SEQ ID NO: 6 |
| HXL004 | Nicotiana benthamiana | Class I | SEQ ID NO: 6 |
| HXL005 | Taraxcum koksaghyz | Class I | SEQ ID NO: 7 |
| HXL009 | Zea mays | Class I | SEQ ID NO: 8 |
| HXL012 | Amaranthus retroflexus | Class I | SEQ ID NO: 10 |
| HXL013 | Glycine max | Class I | SEQ ID NO: 11 |
| HXL015 | Oryza sativa | Class I | SEQ ID NO: 12 |
| HXL032 | Triticum aestivum | Class I | SEQ ID NO: 13 |
| HXL033 | Parthenium argentatum | Class I | SEQ ID NO: 14 |
| HXL034 | Nicotiana benthamiana | Class I | SEQ ID NO: 15 |
| NsD1 | Nicotiana suaveolens | Class II | SEQ ID NO: 16 |
| NsD2 | Nicotiana suaveolens | Class II | SEQ ID NO: 17 |
| NaD1 | Nicotiana alata | Class II | SEQ ID NO: 18 |
| NoD173 | Nicotiana occidentalis spp obliqua | Class II | SEQ ID NO: 19 |
| DmAMP1 | Dahlia merckii | Class I | SEQ ID NO: 20 |
| HXP4 | Artificial | Variant | SEQ ID NO: 21 |
| HXP34 | Artificial | Variant | SEQ ID NO: 22 |
| HXP35 | Artificial | Variant | SEQ ID NO: 23 |
| Consensus | | | SEQ ID NO: 24 |
| HXL008 + Ala | Artificial | Variant | SEQ ID NO: 25 |
| HXL035 + Ala | Artificial | Variant | SEQ ID NO: 26 |
| HXL036 + Ala | Artificial | Variant | SEQ ID NO: 27 |
| HXL001 + Ala | Artificial | Variant | SEQ ID NO: 28 |
| HXL002 + Ala | Artificial | Variant | SEQ ID NO: 29 |
| HXL003 + Ala | Artificial | Variant | SEQ ID NO: 30 |
| HXL004 + Ala | Artificial | Variant | SEQ ID NO: 31 |
| HXL005 + Ala | Artificial | Variant | SEQ ID NO: 32 |
| HXL009 + Ala | Artificial | Variant | SEQ ID NO: 33 |
| HXL012 + Ala | Artificial | Variant | SEQ ID NO: 34 |
| HXL013 + Ala | Artificial | Variant | SEQ ID NO: 35 |
| HXL015 + Ala | Artificial | Variant | SEQ ID NO: 36 |
| HXL032 + Ala | Artificial | Variant | SEQ ID NO: 37 |
| HXL033 + Ala | Artificial | Variant | SEQ ID NO: 38 |
| HXL034 + Ala | Artificial | Variant | SEQ ID NO: 39 |
| NsD1 + Ala | Artificial | Variant | SEQ ID NO: 40 |
| NsD2 + Ala | Artificial | Variant | SEQ ID NO: 41 |
| NaD1 + Ala | Artificial | Variant | SEQ ID NO: 42 |
| NoD173 + Ala | Artificial | Variant | SEQ ID NO: 43 |
| DmAMP1 + Ala | Artificial | Variant | SEQ ID NO: 44 |
| HXP4 + Ala | Artificial | Variant | SEQ ID NO: 45 |
| HXP34 + Ala | Artificial | Variant | SEQ ID NO: 46 |
| HXP35 + Ala | Artificial | Variant | SEQ ID NO: 47 |

BRIEF DESCRIPTION OF THE FIGURES

FIG. 1(A) is a representation of alignments of amino acids of the various defensins encompassed therein.

FIG. 1(B) is a representation of alignments of amino acids of the various defensins encompassed therein.

FIG. 1(C) is a representation of alignments of amino acids of the various defensins encompassed therein.

FIG. 1(D) is a representation of alignments of amino acids of the various defensins encompassed therein.

FIG. 1(E) is a representation of alignments of amino acids of the various defensins encompassed therein.

FIG. 11 is a representation of an amino acid alignment of HXL008, HXL035 and HXL036 and a consensus sequence generated by the alignment. Identical amino acids are highlighted in black, onserved amino acids are highlighted in grey.

DETAILED DESCRIPTION

Figure 2A:
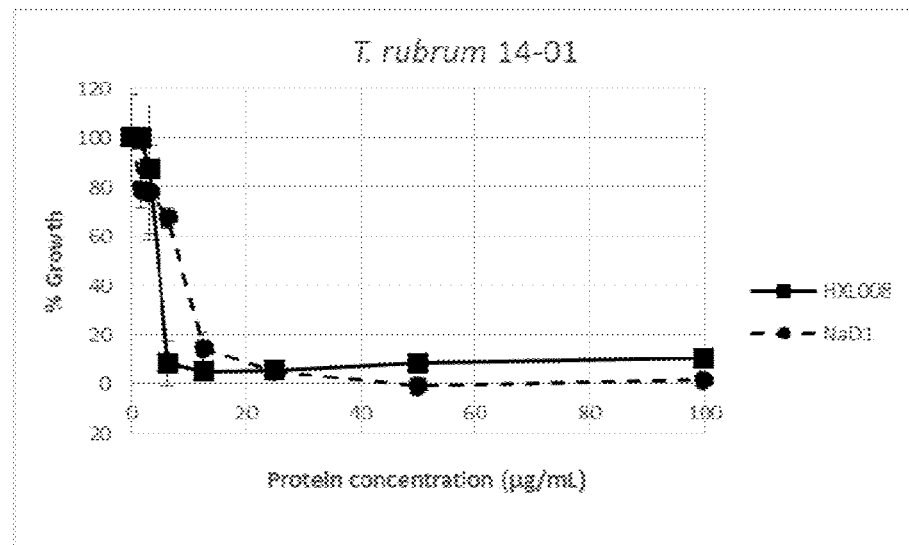
FIG. 2(A) is a graphical representation showing the effect of the plant defensins NaD1 (dashed line) and HXL008 (solid line) on the growth of clinical isolate 14-01 of Trichophyton rubrum in vitro. Fungal growth was measured by the increase in optical density at 595 nm (A595) achieved 72 hours after inoculation of the growth medium and is plotted as a percentage of growth relative to a no-protein control (vertical axis) versus protein concentration (μg/mL, horizontal axis).
Figure 2B:
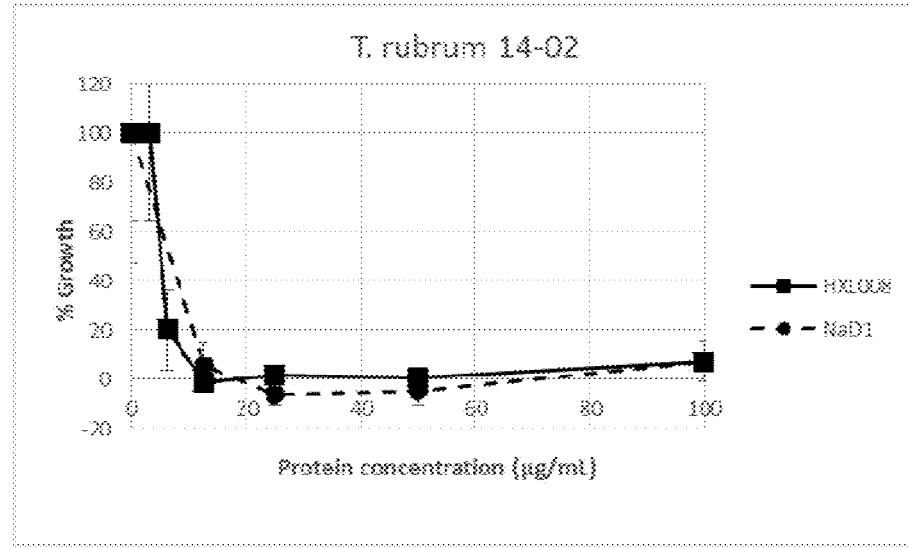
FIG. 2(B) is a graphical representation showing the effect of the plant defensins NaD1 (dashed line) and HXL008 (solid line) on the growth of clinical isolate 14-02 of Trichophyton rubrum in vitro. Fungal growth was measured by the increase in optical density at 595 nm (A595) achieved 72 hours after inoculation of the growth medium and is plotted as a percentage of growth relative to a no-protein control (vertical axis) versus protein concentration (μg/mL, horizontal axis).
Figure 2C:
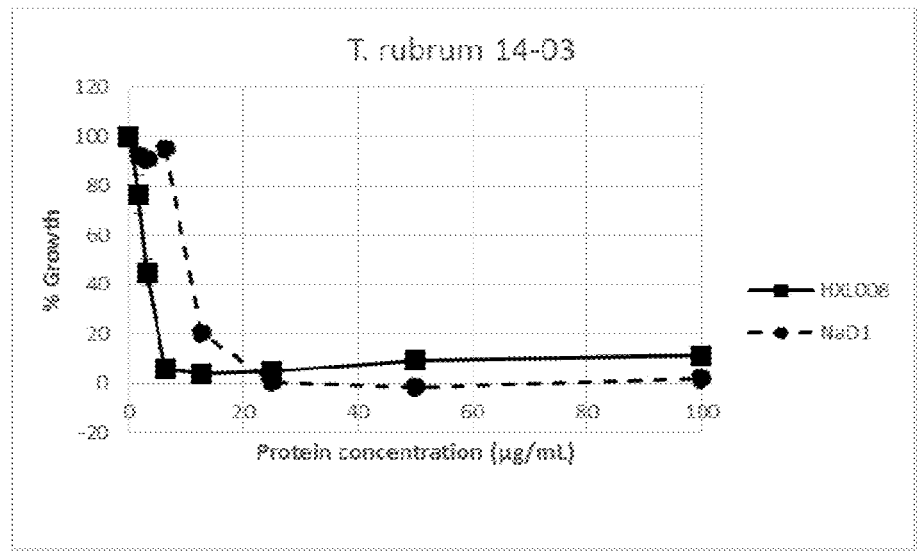
FIG. 2(C) is a graphical representation showing the effect of the plant defensins NaD1 (dashed line) and HXL008 (solid line) on the growth of clinical isolate 14-03 of Trichophyton rubrum in vitro. Fungal growth was measured by the increase in optical density at 595 nm (A595) achieved 72 hours after inoculation of the growth medium and is plotted as a percentage of growth relative to a no-protein control (vertical axis) versus protein concentration (μg/mL, horizontal axis).
Figure 2D:
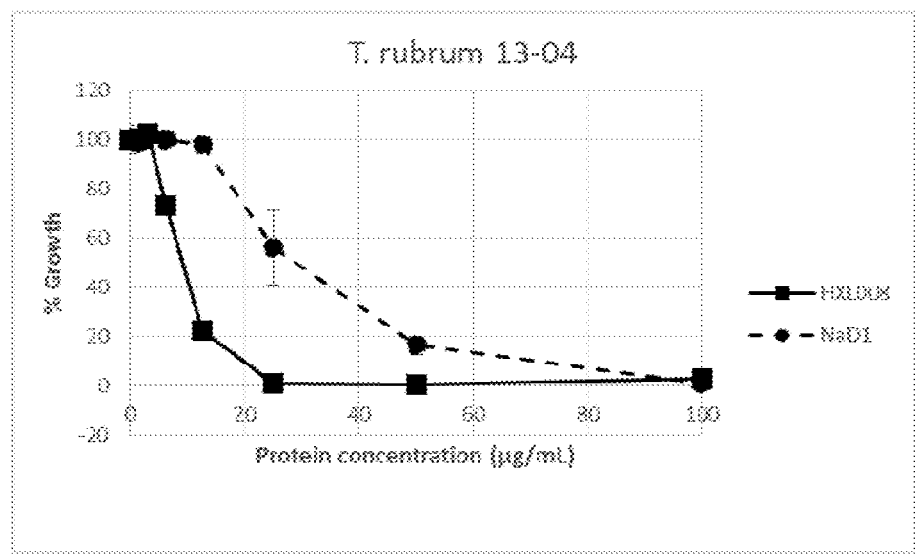
FIG. 2(D) is a graphical representation showing the effect of the plant defensins NaD1 (dashed line) and HXL008 (solid line) on the growth of clinical isolate 13-04 of Trichophyton rubrum in vitro. Fungal growth was measured by the increase in optical density at 595 nm (A595) achieved 72 hours after inoculation of the growth medium and is plotted as a percentage of growth relative to a no-protein control (vertical axis) versus protein concentration (μg/mL, horizontal axis).
Figure 3A:
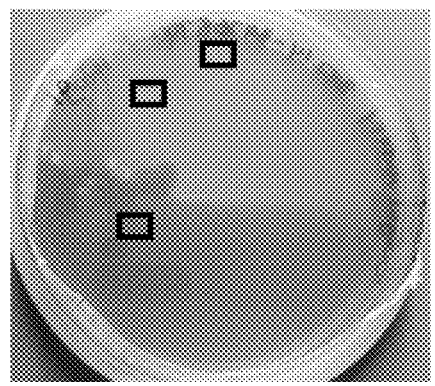
FIG. 3(A) is a photographic representation of surviving colonies of T. rubrum clinical isolate 14-01 grown on agar plates after treatment with 100 μM HXL008 for 72 h.
Figure 3B:
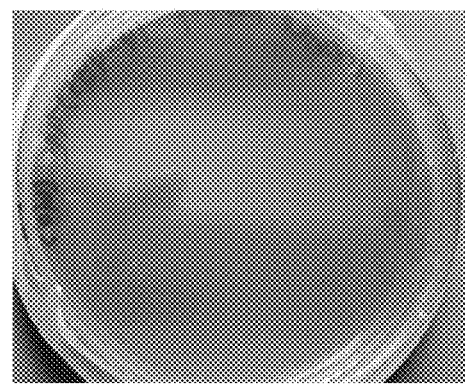
FIG. 3(B) is a photographic representation of surviving colonies of T. rubrum clinical isolate 14-02 grown on agar plates after treatment with 100 μM HXL008 for 72 h.
Figure 3C:
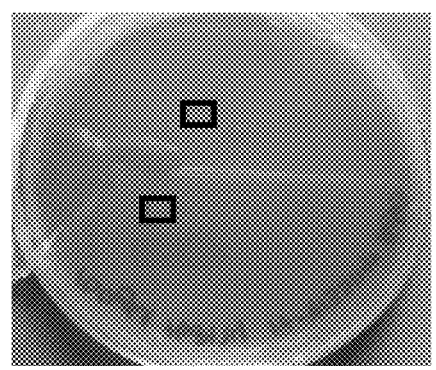
FIG. 3(C) is a photographic representation of surviving colonies of T. rubrum clinical isolate 14-03 grown on agar plates after treatment with 100 μM HXL008 for 72 h.
Figure 3D:
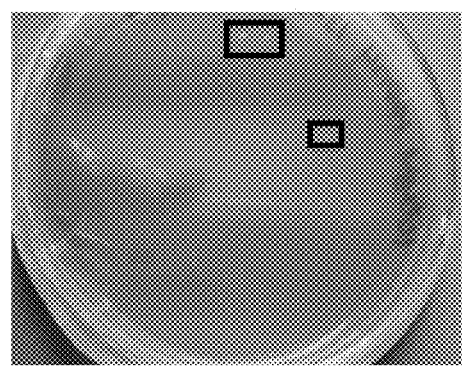
FIG. 3(D) is a photographic representation of surviving colonies of T. rubrum clinical isolate 13-04 grown on agar plates after treatment with 100 μM HXL008 for 72 h.
Figure 3E:
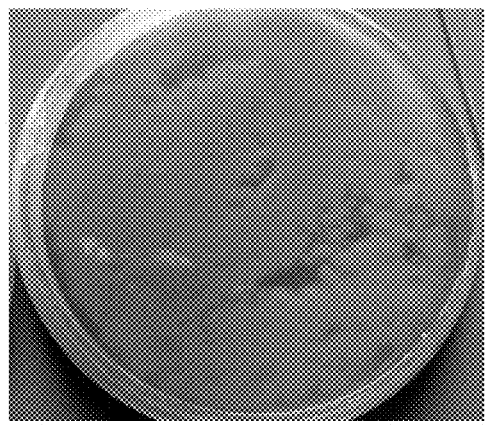
FIG. 3(E) are photographic representations of T. Rubrum, which was not treated with any HXL008 (left panels) after 24 hours and 14 days respectively, T. Rubrum, which was treated with 10 μg/mL HXL008 (center panels) after 24 hours, 14 days and 25 days, respectively, T. Rubrum, (right panels) which was treated with 50 μg/mL HXL008 (center panels) after 24 hours, 14 days and 25 days, respectively.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a defensin" includes a single defensin, as well as two or more defensins; reference to "an agent" includes single agent, as well as two or more agents; reference to "the disclosure" includes a single and multiple aspects taught by the disclosure; and so forth. Aspects taught and enabled herein are encompassed by the term "invention". All such aspects are enabled within the width of the present invention. All variants and derivatives or the various aspects are encompassed by the term "form" of the invention.

Reference to a "defensin" means one of the following plant defensins which retains antifungal activity:

(i) a defensin having the consensus amino acid sequence as set forth in SEQ ID NO:24;

(ii) a defensin selected from the group consisting of HXL008 (SEQ ID NO:1), HXL035 (SEQ ID NO:2) and HXL036 (SEQ ID NO:3);

(iii) a defensin selected from the group consisting of HXL001 (SEQ ID NO:4), HXL002 (SEQ ID NO:5), HXP35 (SEQ ID NO:3), HXL003 (SEQ ID NO:6), HXL004 (SEQ ID NO:7), HXL005 (SEQ ID NO:8), HXL009 (SEQ ID NO:9), HXL012 (SEQ ID NO:10), HXL013 (SEQ ID NO:11), HXL015 (SEQ ID NO:12), HXL032 (SEQ ID NO:13), HXL033 (SEQ ID NO:14), HXL034 (SEQ ID NO:15), NsD1 (SEQ ID NO:16), NsD2 (SEQ ID NO:17), NaD1 (SEQ ID NO:18), NoD173 (SEQ ID NO:19), DmAMP1 (SEQ ID NO:20), HXP4 (SEQ ID NO:21), HXP34 (SEQ ID NO:22) and HXP35 (SEQ ID NO:23);

(iv) a functional naturally occurring or synthetic derivative or variant of any one of SEQ ID NO:1 through 47;

(v) a defensin having at least 80% similarity to any one of SEQ ID NO:1 through 47 after optimal alignment;

(vi) any one of SEQ ID NO:1 through 47 comprising a N-terminal alanine residue (i.e. SEQ ID NO:25 through 47); and/or (vii) a defensin having at least 80% similarity to any one of SEQ ID NO:1 through 3 or after optimal alignment. For convenience, these defensins are encompassed within the consensus amino acid sequence set forth in SEQ ID NO:24.

In an embodiment, the defensin is defined by SEQ ID NO:1, SEQ ID NO:2 or SEQ ID NO:3 or a functional natural or synthetic derivative or variant thereof including a polypeptide having antifungal activity with an amino acid sequence of at least 80% similarity to any one of SEQ ID NO:1, SEQ ID NO:2 or SEQ ID NO:3 after optimal alignment.

When a second defensin is used in combination with a first defensin, the second defensin may be any defensin.

A protocol is described herein which is used to facilitate management of fungal infection including infestation at particular anatomical sites in human and animal subjects. The protocol comprises the use of a plant defensin or a functional natural or synthetic derivative or variant thereof to inhibit or otherwise control the growth of a fungal pathogen on or in horn-like envelopes covering dorsal or terminal phalanges in humans and animals and related cerebral protrusions in horned animals. In an embodiment, the envelope is a finger or toe nail, claw or hoof and the cerebral protrusion is a horn. In an embodiment, the fungal infection leads to onychomycosis. In an embodiment, the defensin has potent fungicidal activity against *Trichophyton rubrum* and no activity or medically acceptable minimal activity against mammalian or bacterial cells. In an embodiment, the defensin has good penetrability of the nail such as a defensin with the consensus amino acid sequence set forth in SEQ ID NO:24. Examples include HXL008 (SEQ ID NO:1), HXL035 (SEQ ID NO:2) and HXL036 (SEQ ID NO:3) or these defensins with a N-terminal alanine residue (SEQ ID NO:25, SEQ ID NO:26 and SEQ ID NO:27, respectively) In an optional embodiment, the defensin is used in synergistic combination with another antifungal agent. The latter agent includes a non-defensin peptide, a proteinase inhibitor, another defensin and a proteinaceous or non-proteinaceous (chemical) agent with antifungal properties. The protocol also extends to treating fungal infection of keratin comprising material such as skin, hair and fur as well as hair and fur follicles.

Enabled herein is a method for inhibiting infection by a fungal pathogen on or in a horn-like envelope covering dorsal or terminal phalanges or related cerebral protrusions on a subject, the method comprising contacting the envelope with an effective amount of a plant defensin or a functional natural or synthetic derivative or variant thereof. In an embodiment, the envelope is a nail, claw or hoof. Hence, taught herein is a method for inhibiting growth of a fungal pathogen on or in a finger nail or toe nail or on an animal claw or hoof, the method comprising contacting the nail or claw or hoof with an effective amount of a plant defensin or a functional natural or synthetic variant or derivative thereof. Generally, the contact is for a time and under conditions sufficient to inhibit growth of the fungal pathogen.

Taught herein is a method for inhibiting infection by a fungal pathogen on or in keratin comprising material on a subject, the method comprising contacting the material with an effective amount of a plant defensin or a functional natural or synthetic derivative or variant thereof. In an embodiment, keratin comprising material is hair or fur. Hence, taught herein is a method for inhibiting growth of a fungal pathogen on or in hair or fur or hair or fur follicle, the method comprising contacting the hair or fur or hair or fur follicle with an effective amount of a plant defensin or a functional natural or synthetic variant or derivative thereof. Generally, the contact is for a time and under conditions sufficient to inhibit growth of the fungal pathogen.

In an embodiment, keratin comprising material is skin. Hence, taught herein is a method for inhibiting growth of a fungal pathogen on or in skin, the method comprising contracting the skin with an effective amount of a plant defensin or a functional natural or synthetic variant or derivative thereof. Generally, the contact is for a time and under conditions sufficient to inhibit growth of the fungal pathogen.

"Fungal inhibition" includes both fungicidic and fungistatic activity, as measured by reduction of fungal growth (or loss of viability) compared to a control. Fungal growth can be measured by many different methods known in the art depending on the fungus. A commonly used method of measuring growth of a filamentous fungus, for example, entails germinating spores in a suitable growth medium, incubating for a time sufficient to achieve measurable growth, and measuring increased optical density in the culture after a specified incubation time. The optical density rises with increased growth. Typically, fungal growth is necessary for pathogenesis. Therefore, inhibition of pathogen growth provides a suitable indicator for protection from fungal disease, i.e. the greater the inhibition, the more effective the protection. Furthermore, the effectiveness of the fungicidal or fungistatic activity can be determined by visual inspection of a nail, claw, hoof or horn or of the hair or fur or hair or fur follicle.

There is no clear definition for successful treatment of onychomycosis. Mycological cure is often defined as a negative result on both the KOH and culture tests (Elewski et al. (2012) Fungal diseases In: Bolognia, Jorizzo, Schaffer eds, *Dermatology* 3$^{rd}$ ed. Philadelphia, Pa.; Elsevier Saunders; chapter 77).

The treatment protocol includes prophylaxis (i.e., prevention) of at risk subjects from infection. A subject "at risk" may be a subject in a tropical climate. Hence, "preventing infection" in the present context, means that the human or animal host is treated with the defensin so as to avoid fungal infection or disease symptoms associated therewith or exhibit reduced or minimized or less frequent fungal infection or disease symptoms associate therewith, that are the natural outcome of the host-fungal interactions when compared to the host not exposed to the defensin. That is to say, fungal pathogen infection is prevented or reduced from causing disease and/or the associated disease symptoms (i.e. onychomycosis). Infection and/or symptoms are reduced by at least about 10%, 20%, 30%, 40%, 50, 60%, 70% or 80% or greater as compared to a host not so treated with the protocol taught herein. The percentage reduction can be determined by any convenient means appropriate to the host and fungal pathogen.

Hence, the action of the defensin is to inhibit fungal pathogen growth, replication, infection and/or maintenance, amongst other inhibitory activities and/or induce amelioration of symptoms of fungal infection or infestation.

In an embodiment, the fungal infection results in or is associated with onychomycosis or a related condition.

Hence, enabled herein is a method for the treatment or prophylaxis of onychomycosis or a related condition in a subject, the method comprising contacting an infected site on the subject with a plant defensin or a functional natural or synthetic derivative or variant thereof for a time and under conditions sufficient to ameliorate the symptoms of onychomycosis.

Reference to "onychomycosis" includes distal subungual onychomycosis, white superficial onychomycosis, proximal subungual onychomycosis and *Candida* onychomycosis. Reference to a "condition related to onychomycosis" includes *tinea* and infection of cuticle tissue surrounding the nail, claw, hoof or horn.

In an embodiment, the fungal infection is tinea capitis, dandruff or seborrheic dermatitis.

Hence, enabled herein is a method for the treatment or prophylaxis of *tinea* capitis, dandruff, seborrheic dermatitis or related condition in a subject, the method comprising contacting the material on the subject with a plant defensin or a functional natural or synthetic derivative or variant thereof for a time and under conditions sufficient to ameliorate the symptoms of fungal infection.

In an embodiment, the fungal infection is of keratin comprising material.

Hence, enabled herein is a method for the treatment or prophylaxis of fungal infection of keratin comprising material in a subject, the method comprising contacting the material on the subject with a plant defensin or a functional natural or synthetic derivative or variant thereof for a time and under conditions sufficient to ameliorate the symptoms of fungal infection.

In relation to the latter embodiment, the keratin comprising material includes skin, hair or fur or is a hair or fur follicle.

Hence, taught herein is a method for the treatment or prophylaxis of fungal infection of hair or fur or a hair or fur follicle on a human, the method comprising contacting the hair or fur or hair or fur follicle on the subject with a plant defensin or a functional natural or synthetic derivative or variant thereof for a time and under conditions sufficient to ameliorate the symptoms of fungal infection.

By "contacting" includes exposure of the fungal pathogen to the defensin following topical administration or application to the human or animal subject. Contact may be with a purified plant defensin or formulation comprising same, or a plant extract which comprises the defensin naturally or which has been engineered to produce the defensin. A formulation includes herbal formulations and extracts such as nail polish and nail wash. Extracts may be derived from plants or a microorganism such as a yeast (e.g., *Pichia*). Hence, the defensin is applied topically to a surface area on the human or animal subject. Reference to "contacting" includes the step of administering to a subject or an infected site on a subject.

In an embodiment, the defensin is formulated in a topical formulation, nail, claw, hoof or horn formulation or body or hair washing solution. A microbial or cell extract comprising the defensin may also be applied. An example is a *Pichia*-derived extract. Topical formulations include an aqueous solution, liquid formulation, solution, drench, tonic, a wash, a spray, paint, a powder, a dispersant, an atomized formulation, cream, ointment, lipstick, gel, sludge, paste, patch, impregnated bandage and the like. Plant extracts comprising the defensin are also contemplated herein including a plant extract comprising the defensin. Generally, the defensin is formulated so as to permit penetration into the target site (e.g., nail, claw, hoof, horn or hair or fur particle). In an embodiment, the defensin is selected based on its penetrability.

Enabled herein is a formulation comprising a plant defensin or a functional natural or synthetic derivative or variant thereof for use in inhibiting infection by a fungal pathogen in or on a horn-like envelope covering a dorsal or terminal phalange or related cerebral protrusion on a human or animal subject.

Further enabled herein is a formulation comprising a plant defensin or a functional natural or synthetic derivative or variant thereof for use in inhibiting infection by a fungal pathogen on a nail, claw, hoof or horn on a human or animal subject.

Further enabled herein is a formulation comprising a plant defensin or a functional natural or synthetic derivative or variant thereof for use in inhibiting infection by a fungal pathogen associated with onychomycosis in a human subject.

Enabled herein is a formulation comprising a plant defensin or a functional natural or synthetic derivative or variant thereof for use in inhibiting infection by a fungal pathogen of keratin comprising material on a human or animal subject.

Further enabled herein is a formulation comprising a plant defensin or a functional natural or synthetic derivative or variant thereof for use in inhibiting infection by a fungal pathogen of hair or fur or a hair or fur follicle on a human or animal subject.

Enabled herein is a formulation comprising a plant defensin or a functional natural or synthetic derivative or variant thereof for use in inhibiting infection by a fungal pathogen associated with tinea capitis, dandruff or seborrheic dermatitis on a human or animal subject.

In an embodiment, taught herein is a therapeutic kit comprising a compartment or in compartmental form wherein a compartment comprises a plant defensin or a functional natural or synthetic derivative or variant thereof. Second or further compartments may comprise other agents or excipients including other antifungal agents. The contents of each compartment may be admixed prior to use or used sequentially in any order. Other antifungal agents include non-defensin peptides, a proteinase inhibitor, another defensin or a proteinaceous or chemical (non-proteinaceous) antifungal agent. Examples of other antifungal agents which may be used in combination with the plant defensin include griseofulvin, terbinafine, amorolfine, ciclopirox, efinaconazole, tavaborole and a triazole.

Reference to a "plant defensin" means those defined herein with reference to Table 2. A defensin from Table 2 may also be selected based on its penetrability of a nail, claw, hoof or horn. A defensin from Table 2 may also be selected based on its potent fungicidal activity against *T. rubrum* and lack of activity or medically acceptable minimal activity against on mammalian and bacterial cells. As defined herein, a defensin includes a defensin having at least about 80% similarity to SEQ ID NO:24 including any one of SEQ ID NO:1, SEQ ID NO:2 or SEQ ID NO:3 or any one of SEQ ID NO:4 through 47. The 80% similarity is determined after optimal alignment and, where necessary, after appropriate spaces are used to optimize the alignment. By "at least 80%" or "at least about 80%" includes 80, 81, 82, 83, 84, 85, 86, 87, 88, 89, 90, 91, 92, 93, 94, 95, 96, 97, 98, 99 and 100%. A useful defensin in the practice of this invention is a defensin which penetrates readily into the nail. Particular examples include HXL008 (SEQ ID NO:1), HXL035 (SEQ ID NO:2) and HXL036 (SEQ ID NO:3) and variants thereof with an N-terminal alanine residue ((SEQ ID NO:25. (SEQ ID NO:26 and (SEQ ID NO:27 respectively).

Hence, taught herein is a method for inhibiting infection of a fungal pathogen on a horn-like envelope covering a dorsal or terminal phalange or related cerebral protrusion or keratin comprising material or follicle for the keratin comprising material on a subject, the method comprising contacting the envelope or protrusion or keratin comprising material with an effective amount of plant defensin selected from SEQ ID NO:1 through 47 or a functional natural or synthetic derivative or variant thereof or a defensin having at least 80% similarity to any one of SEQ ID NO:1 through 47 after optimal alignment or a defensin selected from SEQ ID NO:25 through 47 with an N-terminal alanine residue for a time and under conditions sufficient to ameliorate symptoms of the infection.

Also enabled herein is a method for inhibiting infection of a fungal pathogen on a horn-like envelope covering a dorsal or terminal phalange or related cerebral protrusion or keratin comprising material or follicle for the keratin comprising material on a subject, the method comprising contacting the envelope or protrusion or keratin comprising material with an effective amount of a defensin having the consensus amino acid sequence set forth in SEQ ID NO:24 or a functional natural or synthetic derivative or variant thereof or a defensin having at least 80% similarity to SEQ ID NO:24, optionally with an N-erminal alanine residue for time and under conditions sufficient to amelirorate symptoms of infection.

Further taught herein is the use of HXL008 (SEQ ID NO:1), HXL035 (SEQ ID NO:2) or HXL036 (SEQ ID NO:3) to treat onychomycosis. Also taught is the use of a defensin defined by SEQ ID NO:25, SEQ ID NO:26 or (SEQ ID NO:27 to treat onychomycosis.

The term "similarity" as used herein includes exact identity between compared sequences at the amino acid level. Where there is non-identity at the amino acid level, "similarity" includes amino acids that are nevertheless related to each other at the structural, functional, biochemical and/or conformational levels. In an embodiment, amino acid sequence comparisons are made at the level of identity rather than similarity.

Terms used to describe sequence relationships between two or more polypeptides include "reference sequence", "comparison window", "sequence similarity", "sequence identity", "percentage sequence similarity", "percentage sequence identity", "substantially similar" and "substantial identity". A "reference sequence" is at least 12 but frequently 15 to 18 and often at least 25 or above, such as 30 amino acid residues in length. Because two polypeptides may each comprise (1) a sequence (i.e., only a portion of the complete amino acid sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, Clustal W2 and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25(17):3389-3402. A detailed discussion of sequence analysis can be found in Unit 19.3 of Ausubel et al. (1994-1998) *In: Current Protocols in Molecular Biology*, John Wiley & Sons Inc. Other alignment software includes BWA (Li and Durbin (2010) *Bioinformatics* 26: 589-595) and Bowtie (Langmead et al (2009) *Genome Biol* 10:R25 and BLAT (Kent (2002) *Genome Res* 12:656-664).

The terms "sequence similarity" and "sequence identity" as used herein refer to the extent that sequences are identical or functionally or structurally similar on an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by any suitable method or computer algorithm using standard defaults as used in the reference manual accompanying the software. Similar comments apply in relation to sequence similarity.

Some defensins used herein may be referred to herein as a "naturally occurring" defensin, a "modified" defensin, a "variant" defensin, a "mutated" defensin a "synthetic derivative or variant" or a "chimeric" defensin, depending on its source. For the practice of the present invention, such defensins retain antifungal activity.

In an embodiment, the defensin is a Class II Solanaceous defensin. In an embodiment, the defensin is modified at the loop region between the first β-strand (β-strand 1) and the α-helix at the N-terminal end portion of the defensin. In an embodiment, the loop region comprises the 6 amino acids N-terminal of the second invariant cysteine residue or its equivalent. This region is defined as "Loop1B". A Class II Solanaceous defensin is distinguished from other defensins by a relatively conserved C-terminal end portion of the mature domain.

Included herein is the use of an artificially created defensin comprising a modified Class II Solanaceous defensin backbone wherein the loop region between β-strand 1 and the α-helix on the N-terminal end portion is modified by a single or multiple amino acid substitution, addition and/or deletion to generate a variant defensin which has anti-pathogen activity. In an embodiment, the loop region is Loop1B defined by the 6 amino acid residues N-terminal to the second invariant cysteine residue. Its equivalent region in any defensin is contemplated herein. In an embodiment, the artificially created defensin comprises a modified Class II defensin. The present protocol does not extend to the use of NaD1 comprising its natural amino acid sequence.

Examples of suitable defensins include those listed in Table 1. These comprise synthetic defensin variants such as HXP4 (SEQ ID NO:21), HXP34 (SEQ ID NO:22) and HXP35 (SEQ ID NO:23). Also encompassed herein are the latter three defensins with an N-terminal alanine residue (i.e. SEQ ID NO:45 through 47, respectively). A useful defensin is HXL008 (SEQ ID NO: 1), HXL035 (SEQ ID NO:2) and HXL036 (SEQ ID NO:3) or a functional natural or synthetic derivative or variant thereof includes SEQ ID NO:25, SEQ ID NO:26 and SEQ ID NO:27.

Taught herein is a method for inhibiting infection by a fungal pathogen, on or in a nail, claw, hoof or horn, the method comprising contacting the nail, claw, hoof or horn with an effective amount of a plant defensin selected from the list presented in Table 1 herein or a derivative or variant thereof. Generally, the defensin is applied for a time and under conditions sufficient to ameliorate the symptoms of the infection. In an embodiment, the symptoms are associated with onychomycosis or a related condition.

Taught herein is a method for inhibiting infection by a fungal pathogen, on or in a nail, claw, hoof or horn, the method comprising contacting the nail, claw, hoof or horn with an effective amount of a plant defensin selected from the list presented in Table 2 herein or a derivative or variant thereof. The defensin may be applied at a concentration of between 0.1% and 10% w/v, at a frequency of once a day, twice a day, once every two days, once a week, once every two weeks or once a month, for a period of four weeks, two weeks, one week, three weeks, one month, two months, three months or up to 12 months. In an embodiment, the symptoms are associated with onychomycosis or a related condition.

Taught herein is a method for inhibiting infection by a fungal pathogen, on or in skin, hair or fur, the method comprising contacting the skin, hair or fur or hair or fur follicle with an effective amount of a plant defensin selected from the list presented in Table 1 herein or a derivative or variant thereof. The defensin is applied for a time and under conditions sufficient to ameliorate the symptoms of the infection. In an embodiment, the symptoms are associated with fungal infection.

Taught herein is a method for inhibiting infection by a fungal pathogen, on or in skin, hair or fur, the method comprising contacting the skin, hair or fur or hair or fur follicle with an effective amount of a plant defensin selected from the list presented in Table 1 herein or a derivative or variant thereof. The defensin may be applied at a concentration of between 0.1% and 10% w/v, at a frequency of once a day, twice a day, once every two days, once a week, once every two weeks or once a month, for a period of one week, two weeks, three weeks, one month, two months, three months or up to 12 months. In an embodiment, the symptoms are associated with fungal infection.

In an optional embodiment, the defensin or its derivative or variant is used in combination with another agent such as an antifungal agent. It is proposed that the defensin and the peptide act in synergy. Examples of other agents include a non-defensin antimicrobial peptide, a proteinase inhibitor another defensin or a proteinaceous or non-proteinaceous chemical fungicide.

Chemical antifungal agents for use in combination with a subject defensin include terbinafine, intraconazole, fluconazole, ciclopirox, clotrimazole, amorolfine butenafine, tavaborole, efinaconazole, AN2718 and NP213.

Reference to synergy means that the inhibitory effect of a given defensin or other agent alone is greater when both are used together compared to either used alone. Greco et al. (1995) *Pharmacol Rev.* 47:331-385 define a category of synergy on the basis that the use of two agents in combination has greater activity relative to the additive effects when each is assayed alone. Hence, the definition adopted herein includes all such situations provided that the combined effect of the two agents acting together is greater than the sum of the individual agents acting alone. Furthermore, a combination of agents is deemed synergistic, as the term is intended herein, if there exists a set of conditions, including but not limited to concentrations, where the combined effect of the agents acting together is greater than the sum of the individual components acting alone. Richer (1987) *Pestic Sci* 19:309-315 describes a mathematical approach to establish proof of synergy. This approach uses Limpet's formula for comparing an observed level of inhibition (Io) in the combined presence of two inhibitor agents, X and Y, with an expected additive effect (Ee) resulting from each X or Y acting separately at the same respective concentrations as used to measure their combined effect. Additive percent inhibition, Ee, is calculated as $X+Y-XY/100$ where X and Y are expressed as percent inhibition. Synergism exits where $Io>Ee$.

Synergy may be expressed as a synergy scale. In an embodiment, a value of up to 14 represents no significant synergy such as 0, 1, 2, 3, 4, 5, 6, 7, 8, 9, 10, 11, 12, 13 or 14; a value of from 15 up to 29 represents low synergy such as 15, 16, 17, 18, 19, 20, 21, 22, 23, 24, 25, 26, 27, 28 or 29; a value of from 30 to 60 represents medium synergy such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; a value greater than 60 represents a high degree of synergy. By "greater than 60" includes from 61 to 100 including 61, 70, 80, 90 and 100 and any value in between.

The present method is useful in the treatment or prophylaxis of a subject having an infection or infestation by a fungal pathogen of a horn-like envelope covering a dorsal or terminal phalange or related cerebral protrusion or of keratin comprising material such as skin, hair or fur. The term "subject" includes a human of any age or an animal such as a farm animal (e.g., sheep, pig, horse, cow, donkey, camel, llama, alpaca) or poultry bird (e.g., chicken, duck, turkey, pheasant, peacock)), companion animal (e.g., dog or cat), laboratory test animal (e.g., mouse, rat, rabbit, guinea pig or hamster) or captive wild animal (e.g., wild goat). A "human" or "animal" includes a part thereof such as toe nails, finger nails, claws, hooves, horns, skin, hair or fur.

Reference to a "fungus" includes dermatophytes, yeasts and non-dermatophytic molds (non-dermatophytes). Dermatophytes include *Trichophyton* species including *Trichophyton rubrum*, *Trichophyton interdigitale*, *Trichophyton violaceum*, *Trichophyton tonsurans*, *Trichophyton soudanense* and *Trichophyton mentagrophytes*, *Microsporum fulvum*, *Epidermophyton floccosum* and *Microsporum gypseum*. Yeasts encompass *Candida* species including *Candida albicans* and *Candida glabrata*, The fungus may cause tinea such as Tinea pedis, dandruff or a dermatitis.

Another aspect taught herein is a composition comprising a plant defensin or a functional natural or synthetic derivative or variant thereof with one or more pharmaceutically or veterinary acceptable carriers, diluents or excipients for use in treating or preventing onychomycosis or a related condition. In an optional embodiment, the plant defensin is used in combination with a defensin and another antifungal agent. In an embodiment, the composition is in the form of a spray, mist, micro- or nano-particles, an aqueous solution, drench, a wash, a tonic, a dispersant, an atomized formulation, lipstick, sludge, powder, cream, ointment, gel, patch, impregnated bandage, liquid, formulation, paint or other suitable distribution medium including topical forms of the composition. The defensin may be specifically formulated to facilitate penetration of a nail, claw, hoof or horn or hair or fur particle.

Useful applications include solutions, paints, creams, powders, drops, ointments, shampoos and drenches for fungal infection of nails, claws, hooves or horns or of hair or fur.

Compositions which comprise the defensin and optionally another antifungal agent described herein, generally include a carrier, excipient, diluent, preservative, stabilizer and/or a solid or liquid additive. Plant extracts comprising the defensin may also be used. A formulation includes a body wash or shampoo or drench.

The composition may take a wide variety of forms depending on the intended method of administration. Generally, but not exclusively, topical compositions are used for human or animal subjects. In preparing the compositions, usual media may be employed such as, for example, water, organic acids such as citric acid or acetic acid, glycols such as ethylene glycol, propylene glycol, 1,3-butylene glycol and polyethylene glycol, oils, alcohols such as ethanol, methanol or isopropanol, preservatives and/or coloring agents. The compositions may take the form of a liquid preparation such as, for example, suspensions, elixirs and solutions. Carriers such as starches, sugars, microcrystalline cellulose, diluents, granulating agents, lubricants, binders, disintegrating agents and the like may also be used. The composition may also be in the form of a paint, powder, dispersant, ointment, cream or wash.

The composition may include one or more acceptable excipients such as ethylenediaminetetraacetic acid, cyclomethicone, hydroxypropyl cellulose, carboxymethyl cellulose, hydroxypropyl chitosan, polyvinylpyrrolidone, ethyl acetate, diisopropyl adipate, isopropyl myristate and myristyl lactate.

The defensin is administered directly to the infected site, generally for a time and under conditions sufficient to ameliorate the symptoms of infection. This includes amelioration of the symptoms of onychomycosis or a related condition.

In an embodiment, the defensin is administered directly to the infected site, at a concentration of between 0.1% and 10% w/v, at a frequency of once a day, twice a day, once every two days, once a week, once every two weeks or once a month, for a period of one week, two weeks, three weeks, one month, two months, three months or up to 12 months.

When administered by aerosol or spray, the compositions are prepared according to techniques well-known in the art of pharmaceutical formulation and may be prepared as solutions in saline, employing benzyl alcohol or other suitable preservatives, absorption promoters to enhance bioavailability, fluorocarbons and/or other solubilizing or dispersing agents known in the art.

The effective dosage of the defensin may vary depending on whether used alone or in a particular combination, the mode of administration, the fungal pathogen being treated and the severity of the fungal pathogen infestation. Thus, the dosage regimen utilizing the defensin is selected in accordance with a variety of factors including type, species, age, weight, sex and medical disposition of the subject; the severity of the condition to being treated; the mode of administration; and the particular defensin thereof employed. A physician, clinician or veterinarian of ordinary skill can readily determine and prescribe the effective amount of the defensin required to prevent, counter or arrest the progress of fungal pathogen infestation. Slow release formulations are also contemplated herein. In an embodiment, the composition comprises a penetrant to facilitate entry of the defensin into the site of infection In an embodiment, the composition contains a molecule that increases permeation across the nail. Molecules that increase nail permeation include inorganic salts, mercaptan, glycine, cysteine, urea, peroxide, acids such as phosphoric acid or thioglycolic acid, alkalis such as sodium or potassium hydroxide, reducing agents (thiols, sulfites), dimethyl sulfoxide, poly glycols, glycerine, $C_{2-5}$ alcohol, $C_{2-8}$ polyol, $C_{6-24}$ fatty acid triglyceride, $C_{6-24}$ fatty alcohol, $C_{6-24}$ alkyl sulphate, $C_{6-24}$ fatty acid; non-ionic surfactant or mixtures thereof (Murthy et al. (2009) *J Pharm Sci* 98(11):4264-4271; Nair et al. (2009) *J Pharm Pharmacol* 61(4):413-417; Malhotra and Zatz (2002) *J Pharm Sci* 91(2):312-323; Khengar et al. (2007) *Pharm Res* 24(12):2207-2212; Murdan (2008) *Expert Opin Drug Deliv* 5(11):1267-1282; Reeves U.S. Pat. No. 6,391,879; Willers et al. European Patent No. 2664327).

Another aspect provides a protocol or method for treating or preventing an animal including a mammalian such as a human subject infected or infested with a fungal pathogen, the protocol or method comprising applying to the subject an anti-fungal pathogen effective amount of a composition comprising the plant defensin at a site which is a horn-like envelope covering a dorsal or terminal phalange or related cerebral protrusion or is keratin comprising material.

Yet another aspect provides a protocol or method for treating or preventing onychomycosis or fungal infection of the skin hair or fur, the protocol or method comprising applying to a nail, claw, hoof, horn or hair or fur particle or hair or fur follicle an anti-fungal pathogen effective amount of a composition comprising the plant defensin and optionally another antifungal agent. The latter includes a non-defensin antimicrobial peptide, a proteinase inhibitor, another defensin and a proteinaceous or non-proteinaceous chemical antifungal agent.

The term "applying" includes contacting and exposing as well as administering to a site. In an embodiment, the application includes the act of penetrating the nail, claw, hoof or horn or the act of penetrating a hair or fur particle or hair or fur follicle.

The defensin is useful for combating a fungal disease or infection of horn-like envelopes and related cerebral protrusions such as nails, claws, hooves and horns or of keratin comprising material such as skin, hair or fur. In an embodiment, the subject specification teaches a protocol for the treatment or prophylaxis of onychomycosis or a related condition. In an embodiment, the subject specification teaches a protocol for the treatment or prophylaxis of tinea capitis, dandruff and seborrheic dermatitis or a related condition. The protocol has human and veterinary applications.

The present defensin may be manufactured based on its amino acid sequence using standard stepwise addition of one or more amino acid residues using, for example, a peptide or protein synthesizer. Alternatively, the defensin is made by recombinant means. A recombinant defensin may include an additional alanine residue at its N-terminus. Hence, defensins contemplated herein may contain the N-terminus alanine residue.

Another aspect taught herein is a method for producing the plant defensin recombinantly. In an embodiment, the plant defensin is produced using a microbial expression system. In a further embodiment, the expression system is a yeast-based expression system such as *Pichia pastoris*. In a preferred embodiment, the plant defensin is expressed as a fusion protein with a secretion signal that targets the protein outside the cell. The secretion signal is then removed enzymatically to release mature plant defensin into the expression medium. The plant defensin is then purified by ion-exchange chromatography. In a preferred embodiment, the plant defensin is purified by cation-exchange chromatography using a resin such as SP-Sepharose. The plant defensin is then further purified by size-exclusion chromatography using a medium suitable for small proteins such as Superdex 30.

In addition, the defensin may be subject to chemical modification to render the defensin a chemical analog. Such defensin analog, may exhibit greater stability or longer half life at the point of contact with the tissue.

Analogs contemplated herein include but are not limited to modification to side chains, incorporating of unnatural amino acids and/or their derivatives during peptide, polypeptide or protein synthesis and the use of crosslinkers and other methods which impose conformational constraints on the defensin molecule. This term also does not exclude modifications of the defensin, for example, glycosylations, acetylations, phosphorylations and the like. Included within the definition are, for example, defensins containing one or more analogs of an amino acid (including, for example, unnatural amino acids) or defensins with substituted linkages. Such analogs may have enhanced stability and/or penetrability.

Examples of side chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH4.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A bifunctional crosslinkers such as the bifunctional imido esters having (CH2)n spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of Cα and N α-methylamino acids, introduction of double bonds between Cα and Cβ atoms of amino acids and the formation of cyclic peptides or analogs by introducing covalent bonds such as forming an amide bond between the N and C termini, between two side chains or between a side chain and the N or C terminus.

Mimetics are another useful group of defensin analog. The term is intended to refer to a substance which has some chemical similarity to the defensin and mimics its anifungal activity. A peptide mimetic may be a peptide-containing molecule that mimics elements of protein secondary structure (Johnson et al., Peptide Turn Mimetics in Biotechnology and Pharmacy, Pezzuto et al., Eds., Chapman and Hall, New York, 1993). The underlying rationale behind the use of peptide mimetics is that the peptide backbone of proteins exists chiefly to orient amino acid side chains in such a way as to facilitate activity actions.

Still another aspect provides a method for reducing or controlling fungal infection or infestation on a human nail, the method comprising topically applying a plant defensin or a functional natural or synthetic derivation or variant thereof and optionally another antifungal agent to a potentially infected region on the human. In an embodiment, the medicament is in the form of a solution, powder, spray, atomizer, nanoparticle, gel, paste, impregnated bandage, paint, aerosol, drench or other liquid. The anti-fungal formulation may also be a slow release composition.

Still another aspect provides a method for reducing or controlling fungal infection or infestation on human hair, the method comprising topically applying a plant defensin or a functional natural or synthetic derivation or variant thereof and optionally another antifungal agent to a potentially infected region on the human. In an embodiment, the medicament is in the form of a solution, powder, spray, atomizer, nanoparticle, gel, paste, impregnated bandage, paint, aerosol, drench or other liquid. The anti-fungal formulation may also be a slow release composition.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The present disclosure illustratively described herein suitably may be practiced in the absence of any element or elements, limitation or limitations which is not specifically disclosed herein.

When a Markush group or other grouping is used herein, all individual members of the group and all combinations and sub-combinations possible of the group are intended to be individually included in the disclosure.

When a range is recited herein, it is intended that all sub-ranges within the stated range, and all integer values within the stated range, are intended, as if each sub-range and integer value was recited.

EXAMPLES

Aspects disclosed and enabled herein are now described in the following non-limiting Examples.

Methods

Purification of Defensins from *Pichia pastoris*

A single pPINK-defensin *P. pastoris* PichiaPink (Trademark) strain 1 colony is used to inoculate 25 mL of BMG medium (described in the Invitrogen *Pichia* Expression Manual) in a 250 mL flask and that is incubated over for 2-3 days in a 30° C. shaking incubator (140 rpm). The culture is used to inoculate 200 mL of BMG in a 1 L baffled flask which is placed in a 30° C. shaking incubator (140 rpm) overnight. The cells are harvested by centrifugation (1,500× g, 10 min, 4° C.) and resuspended into 1 L of BMM medium in a 5 L baffled flask and incubated in a 28° C. shaking incubator for 3 days (2 days for NaD1). The cultures are induced at t=24 and 48 h. The expression medium is separated from cells by centrifugation (6000 rpm, 20 min, 4° C.). The medium is adjusted to pH 3.0 before it is applied to an SP Sepharose column (1 cm×1 cm, Amersham Biosciences) pre-equilibrated with 100 mM potassium phosphate buffer, pH 6.0. The column is then washed with 100 mL of 100 mM potassium phosphate buffer, pH 6.0 (wash×2 for HXL004). Bound protein is eluted in 10×10 mL of 100 mM potassium phosphate buffer containing 500 mM NaCl. A dot blot is performed to identify factions with the highest concentration of eluted protein and those fractions are concentrated down to 1 mL using a centrifugal column and washed 5× using sterile milli Q ultrapure water. The protein concentration of *Pichia*-expressed defensin is determined using the bicinchoninic acid (BCA) protein assay (Pierce Chemical Co.) with bovine serum albumin (BSA) as the protein standard.

The defensins contemplated for use herein are listed in Tables 1 and 2 and include defensins having at least 80% similarity to any one of the listed defensins after optimal alignment.

FIGS. 1(a) through (e) provide an alignment showing the similarity of amino acid sequences between (see Table 1 for definitions). FIG. 11 provides an alignment of amino acid sequences for HXL008 (SEQ ID NO:1), HXL035 (SEQ ID NO:2) and HXL036 (SEQ ID NO:3). This alignment is used to generate consensus amino acid sequence set forth in SEQ ID NO:24. Any of these sequences may contain an optional N-terminal alanine residue.

Example 1

Inhibition of the Growth of *Trichophyton Rubrum* and *Microsporum Fulvum* in the Presence of a Plant Defensin Plant defensins include a Solanaceous Class II defensin (NaD1) and Class I defensins (HXL001, HXL002, HXL004, HXL005, HXL008, HXL009, HXL012, HXL013, HXL015, NaD2). See Tables 1 and 2 for the sequence identifiers.

The inhibitory effects of the plant defensins on the growth of *Trichophyton rubrum, T. interdigitale, Microsporum fulvum* and *C. albicans* (obtained from the National Mycology Reference Centre, South Australia Pathology at the Women's and Children's Hospital, Adelaide, Australia) are measured essentially as described by Broekaert et al. (1990) *FEMS Microbiol Lett* 69:55-59.

Spores of *T. rubrum, T. interdigitale* and *M. flavum* are isolated from sporulating fungus growing on ½ strength Sabouraud dextrose agar (SDA). Spores were removed from the plates by the addition of ½ strength potato dextrose broth (PDB). *C. albicans* cells are grown in Yeast Peptone Broth (YPD) for 16 h. Spore and cell concentrations are measured using a hemocytometer.

Antifungal assays are conducted in 96 well microtitre plates essentially as herein described. Wells are loaded with 20 μL of filter sterilized (0.22 μm syringe filter, Millipore) defensin (10× stock for each final concentration) or water and 80 μL of 5×10$^4$ spores/mL (*T. rubrum, T. interdigitale, M. fulvum*) or 5,000 cells/mL (*C. albicans*) in ½ strength PDB. The plates are incubated at 30° C. Fungal growth is assayed by measuring optical density at 595 nm (A595) using a microtitre plate reader (SpectraMax Pro M2; Molecular Devices. Growth is allowed to proceed until the optical density (OD) of the fungus in the absence of any test defensin reached an OD of 0.2. Each test is performed in duplicate.

After incubation for 72 h, the media from wells containing clinical isolates of *T. rubrum* incubated with 100 g/mL HXL008 was plated onto fresh Sabouraud dextrose agar. Plates were incubated at 30° C. for 5 days to allow colonies to develop before being photographed.

The results of the inhibition assays are shown in Table 3. HXL005, HXL008 and HXL035 are the most effective plant defensins across the range of fungal pathogens. HXL001 and HXL009 did not display any activity at the concentrations tested. HXL002 and NaD2 are very poor inhibitors of *M. fulvum* and *C. albicans*. HXL004, HXL012, HXL013 and HXL015 display intermediate activity across the range of pathogens.

The results of inhibition of clinical isolates of *T. rubrum* by HXL008 (solid line) and NaD1 (dashed line) are shown in FIGS. 2(a) to 2(d). Both peptides inhibited fungal growth at low concentrations with IC50s of below 20 μg/mL against four clinical isolates. However, in all cases HXL008 inhibited growth at a lower concentration than NaD1.

The results of cell survival assays for clinical isolates of *T. rubrum* are shown in FIGS. 3(a) to 3(e). Plates that had been inoculated with cells that had not been incubated with a plant defensin were almost completely covered in growth. In contrast, plates that were inoculated with cells had been incubated in the presence of HXL008 for 72 h only had 1-3 colonies indicating that almost all the cells were dead.

TABLE 3

| Defensin | IC$_{50}$ against *T. rubrum* (μg/mL) | IC$_{50}$ against *M. fulvum* (μg/mL) | IC$_{50}$ against *T. interdigitale* (μg/mL) | IC$_{50}$ against *C. albicans* (μg/mL) |
|---|---|---|---|---|
| HXL001 | >100 | >100 | | 35 |
| HXL002 | | 50 | | 35 |
| HXL003 | | >100 | | >100 |
| HXL004 | 27.5 | 12 | 19 | 20 |
| HXL005 | 3 | 5 | 3.5 | 22 |
| HXL008 | 3 | 7 | 3.5 | 20 |
| HXL009 | | >100 | | >100 |
| HXL012 | 2 | 18 | 2 | 42 |
| HXL013 | 22 | 5.5 | | 20 |
| HXL015 | 10 | 12.5 | 3.5 | |
| HXL035 | 2 | 2 | 1 | 18 |
| NaD2 | | 38 | | 43 |
| NaD1 | 8 | 5.3 | 10 | 20 |

Example 2

Inhibition of the Growth of *Trichophyton Rubrum* over 28 Days in the Presence of HXL008

The inhibitory effect of HXL008 on the growth of *Trichophyton rubrum* (obtained from the National Mycology Reference Centre, South Australia Pathology at the Women's and Children's Hospital, Adelaide, Australia) was monitored over 28 days.

Spores of *T. rubrum*, are isolated from sporulating fungus growing on ½ strength Sabouraud dextrose agar. Spores are removed from the plates by the addition of ½ strength potato dextrose broth (PDB). Spore and cell concentrations are measured using a hemocytometer.

Spores were diluted to a concentration of 5×10$^4$ spores/mL in ½ PBD (2 mL) containing 0, 10 or 50 μg/mL HXL008. Cultures are incubated at 30 C without shaking. After 24 h, 100 μL of each culture is extracted and plated onto ½ SDA plates. An additional 100 uL of ½ PDB is then added containing either 0, 20 or 100 μg of HXL008. SDA plates are then incubated at 30 C for 5 days. This process is repeated every 24 h for 28 days. After 15 days, the culture containing no HXL008 becomes too thick to pipette and is no longer used in the assay.

Figure 4A:
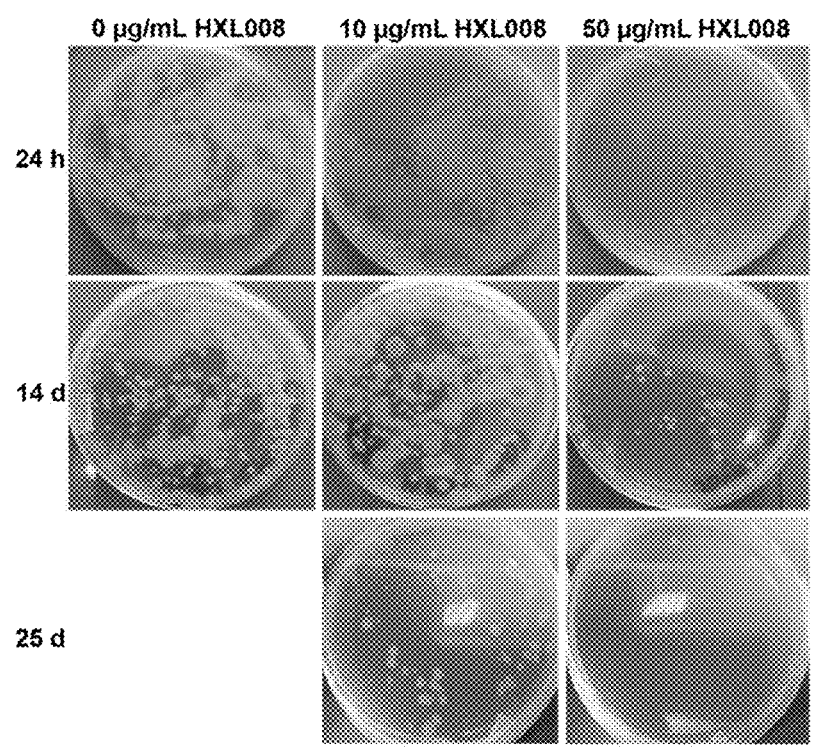
FIG. 4A is a photograp Plates are from cultures treated for 24 h (top panels), 14 d (middle panels) or 25 d (lower panels).
Figure 4B:
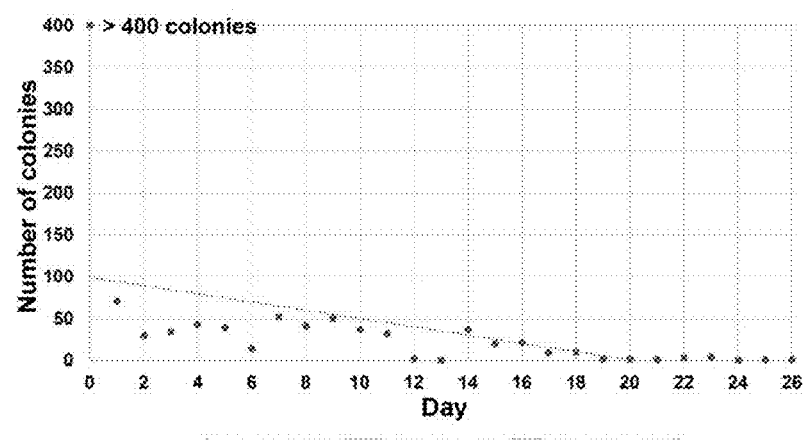
FIG. 4B is a graphical representation of the number of colonies surviving in 100 μL of culture after daily treatment with HXL008 (50 μg/mL/day).
Figure 4C:
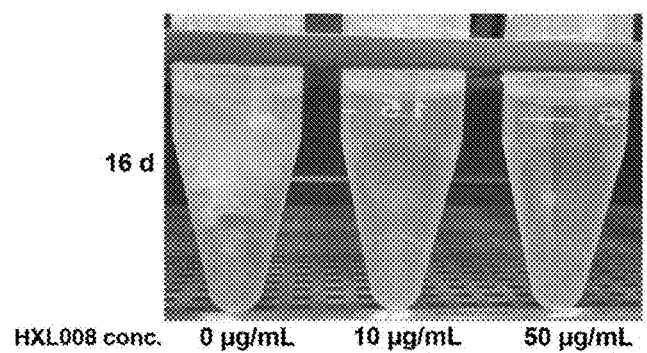
FIG. 4C is a photograph of the cultures in the absence (left panel) or presence of 10 μg/mL (middle panel) or 50 μg/mL (right panel) of HXL008.

The results of the inhibition assay are presented in FIG. 4. Cultures treated with either 10 μg/mL or 50 μg/mL did not display any visible growth of *T. rubrum* over the duration of the assay. Within 24 h, HXL008 at 50 μg/mL had killed more than 80% of *T. rubrum* cells, as visible when plated onto ½ SDA in the absence of HXL008. Over the next 19 days the number of surviving colonies continued to decrease. After 20 days of treatment, plates had either 0 or only 1 colony indicating that more than 99.5% of the cells were dead.

Example 3

Penetration of Plant Defensins through Human Nails

Penetration of NaD1 through human nails was measured according to the method of Hui et al. (2002) *J Pharm Sci*

91(1):189-195. Human toenails were obtained from ScienceCare (USA) and washed with phosphate buffered saline (details, PBS) before being placed on a kimwipe that had been soaked in PBS for 3 h to rehydrate the nail. The nail was then placed in a plastic nail adapter with a dosing area of 0.5×0.5 cm (Permagear, USA) and a cotton bud wetted with 75 microliters of PBS was placed in the receptor chamber in contact with the underside of the nail.

Protein (10-30 µL of 5-10 mg/mL solution) was applied to the top of the nail every 24 h for 4 days. The cotton bud in contact with the underside of the nail was removed after 24 h and every 24 h following. Protein that had passed through the nail was recovered from the cotton bud by washing twice with 500 µL of 0.1% v/v trifluoroacetic acid. Recovered protein was quantified using RP-HPLC.

Figure 5:
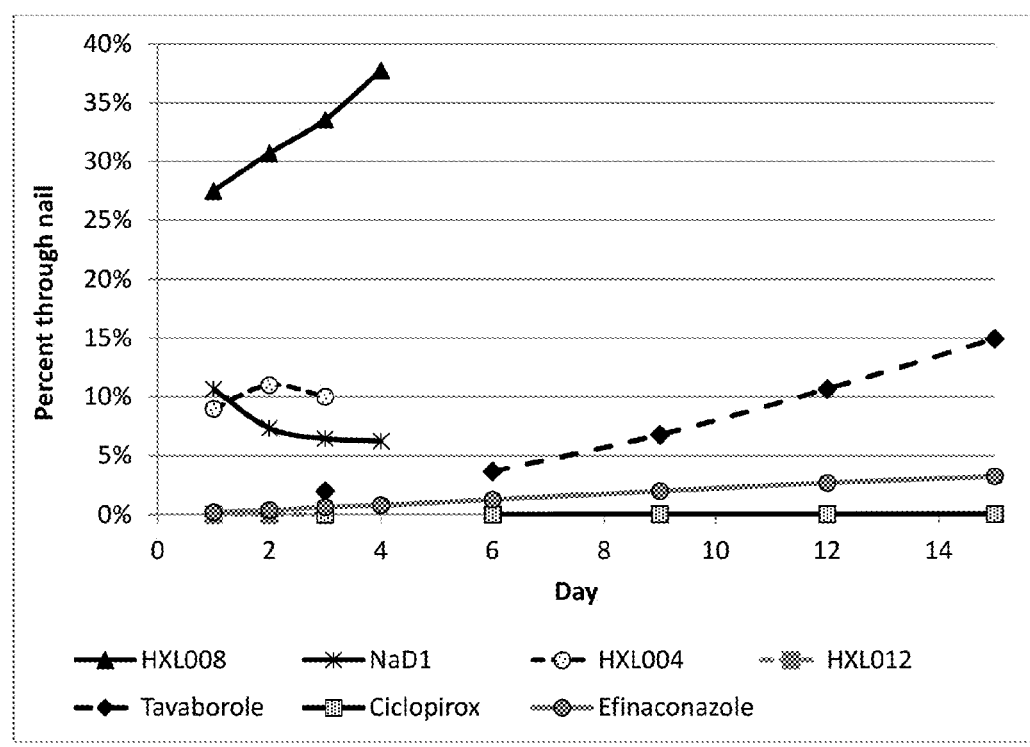
FIG. 5 is a representation of the penetration of nails by HXL008 (black triangles, solid black line), NaD1 (black stars, solid black line), HXL004, (dotted circles, dashed black line), HXL012 (grey square, dashed grey line), tavaborole (black diamond, black dashed line), ciclopirox (dotted square, solid black line) and efniaconazole (grey circles, solid grey line) using a nail adapter system with a wetted-cotton bud acting as the receptor solution underneath the nail.
Figure 6:
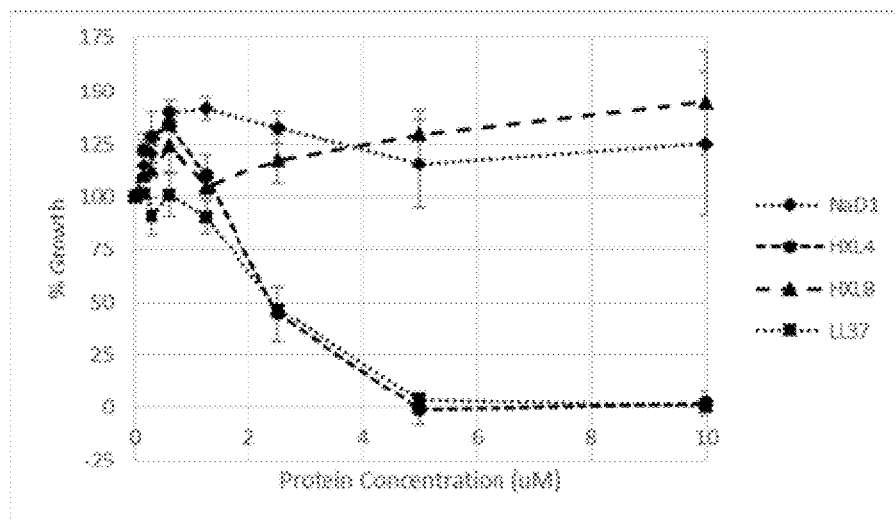
FIG. 6 is a representation of the growth of *Escherichia coli* in the presence of varying concentrations of the plant defensins NaD1(♦ dotted line), HXL004 (● dashed line) and HXL008 (▲ dashed line). The human antimicrobial peptide LL37 (■ dotted line) was used as a control.

The results of the nail penetration assays are represented in Table 4 and FIG. 5. When applied daily to the surface of nails, the plant defensins HXL008, NaD1 and HXL004 were able to penetrate nails faster and more effectively than the active ingredients of current topical onychomycosis therapies (tavaborole, efinaconazole and ciclopirox). More HXL008 was detected coming through the nail than NaD1 or HXL004. The plant defensin HXL012 did not penetrate the nail.

zero data points. Plates were incubated at 37° C. for 18 hours before reading again at $OD_{595}$ to assess the amount of *E. coli* growth.

Figure 7:
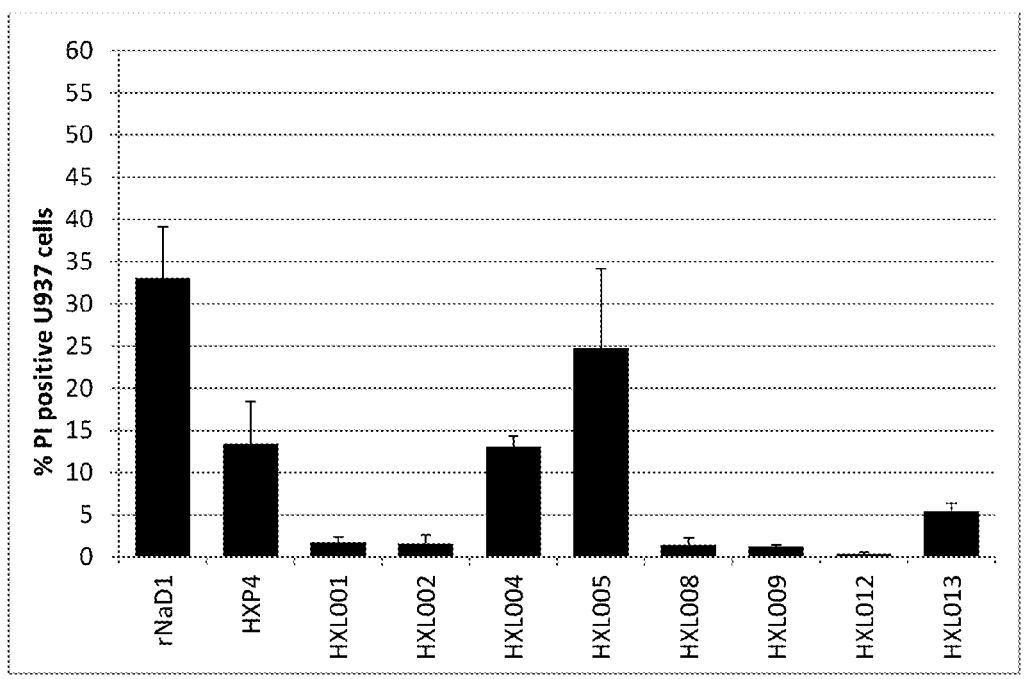
FIG. 7 is a representation of the permeabilization of human U937 cells by rNaD1, HXP4, HXL001, HXL002, HXL004, HXL005, HXL008, HXL009, HXL012 and HXL013 (10 μM). Permeabilization was measured by monitoring uptake of the fluorescent dye propidium iodide (PI).

The results of inhibition of *E. coli* is shown in FIG. 7. HXL004 inhibited the growth of *E. coli* in a concentration dependent manner, similar to the LL37 control. NaD1 and HXL008 did not inhibit growth of *E. coli* at the concentrations tested.

Example 5

Survival of Mammalian Cells in the Presence of Plant Defensins

Human monocytic lymphoma (U937) cells are cultured in RPMI-1640 medium. All culture media are supplemented with 5-10% v/v fetal calf serum, 100 U/ml of penicillin, and 100 µg/ml of streptomycin. Cell lines are cultured at 37° C. in a humidified atmosphere containing 5% v/v $CO_2$. Adherent cell lines are detached from the flask by adding a mixture containing 0.25% v/v trypsin and 0.5 µM EDTA.

A flow cytometry-based propidium iodide (PI) uptake assay is performed to analyze the ability of plant defensins to permeabilize U937 cells (essentially as described in Poon

TABLE 4

| | Cumulative amount through nail (µg) | | | | | | | |
|---|---|---|---|---|---|---|---|---|
| Day | 1 | 2 | 3 | 4 | 6 | 9 | 12 | 15 |
| HXL008 (30 uL of 1% solution, 0.2 cm² daily application) | 83 28% | 184 31% | 302 34% | 453 38% | | | | |
| NaD1 (30 uL of 1% solution, 0.2 cm² daily application) | 32 11% | 44 7% | 58 6% | 75 6% | | | | |
| HXL004 (20 uL of 0.5% solution, 0.2 cm² daily application) | 9 9% | 22 11% | 30 10% | | | | | |
| HXL012 (20 uL of 0.5% solution, 0.2 cm² daily application) | 0 0% | 0 0% | 0 0% | | | | | |
| Tavaborole (10 uL of 10% solution, 0.8 cm² daily application) | | | 60 2.0% | | 220 3.7% | 610 6.8% | 1280 10.7% | 2240 14.9% |
| Ciclopirox (10 uL of 10% solution, 0.8 cm² daily application) | | | 1 0.03% | | 2 0.03% | 4 0.04% | 6 0.05% | 9 0.06% |
| Efinaconazole (2 uL of 10% solution, 0.03 cm² single application) | 0.4 0.2% | 0.7 0.4% | 1.3 0.7% | 1.6 0.8% | 2.6 1.3% | 4.0 2.0% | 5.4 2.7% | 6.5 3.3% |

Example 4

Inhibition of the Growth of *Escherichia Coli* in the Presence of Plant Defensins A single *E. coli* colony was used to inoculate 5 ml of Luria-Bertani media and grown overnight at 37° C. The following day, the optical density of the culture was measured and the *E. coli* diluted to an optical density at 600 nm ($OD_{600}$) of 0.01 in Mueller-Hinton Broth. Diluted *E. coli* were added to 96-well plates with defensins at concentrations of 10 µM, 5 µM, 2.5 µM, 1.25 µM, 0.625 µM, 0.3125 µM or 0.1625 µM. Plates were read at $OD_{595}$ to obtain time et al, 2014). Briefly, cells are suspended to $1 \times 10^6$ cells/ml in 0.1% v/v BSA/RPMI-1640 and incubated with plant defensins (10 µM) at 37° C. for 30 min. Samples are added to PBS containing a final concentration of 1 µg/ml PI and placed on ice. Samples are then analyzed immediately using the BD FACSCanto II Flow Cytometer and BD FACSDiva software v6.1.1. The resultant flow cytometry data is analyzed using FlowJo software v8.8.6. Cells are gated appropriately based on forward scatter and side scatter and cell permeabilization is defined by PI-positive staining.

The results of the PI-uptake assay are shown in FIG. 7. The plant defensins NaD1 and HXL005 are toxic to mammalian cells under the conditions tested. NaD1 permeabilized 33% of cells while HXL005 permeabilized almost 25%. The plant defensins HXP4, HXL004 and HXL013 were less toxic to mammalian cells permeabilising just 13% (HXP4 and HXL004) or 5% (HXL013) of cells. In contrast, HXL001, HXL002, HXL008, HXL009 and HXL012 were not significantly toxic to mammalian cells under the conditions tested, permeabilizing less than 2% of cells.

Example 6

Human Red Blood Cell Lysis in the Presence of Plant Defensins

Human red blood cells (RBCs) were collected from whole blood and washed with 1×PBS and pelleted at 1000×g for 10 min. RBCs were diluted 1 in 10 for treatment with plant defensins (100 µM) and incubated over-night under a humidified atmosphere of 5% v/v $CO_2$/95% v/v air. After 24 h incubation, the cells were centrifuged for 10 min at 2000 rpm, with the supernatant diluted to 1 in 100 with 1×PBS.

Released haemoglobin indicative of RBC lysis was then determined by measuring absorbance at 412 nm. Results have been normalised to RBCs treated with water (designated 100% lysis).

Figure 8:
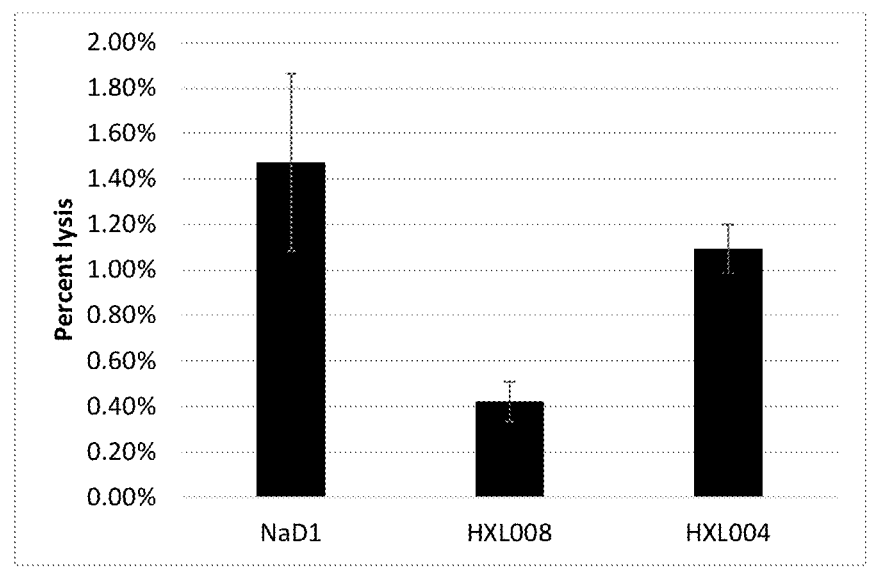
FIG. 8 is a representation of the lysis of red blood cells induced by HXL008, HXL004 and NaD1 measured relative to a water control.

The results of the red blood cell lysis assay is shown in FIG. 8. At 100 µM, the plant defensins NaD1 and HXL004 lysed 1.47 and 1.09 percent of RBCs respectively while HXL008 lysed just 0.42 percent. Error bars represent standard deviation.

Example 7

Effect of Formulation Components on Penetration of HXL008 through Human Nails

HXL008 was dissolved to a concentration of 10 mg/mL in either water, 50 mM citrate buffer pH 4.0 or 50 mM citrate buffer pH 4.0 containing 20% v/v ethanol and 0.5 mM EDTA. Penetration of HXL008 in each formulation through human nails was measured according to the method of Hui et al. (2002) Supra. Human toenails were obtained from ScienceCare (USA) and washed with phosphate buffered saline (PBS) before being placed on a kimwipe that had been soaked in PBS for 3 h to rehydrate the nail. The nail was then placed in a plastic nail adapter with a dosing area of 0.5×0.5 cm (Permagear, USA) and a cotton bud wetted with 75 microliters of PBS was placed in the receptor chamber in contact with the underside of the nail.

Protein in formulation (10 µL of 10 mg/mL solution) was applied to the top of the nail every 24 h for 2 or 3 days. The cotton bud in contact with the underside of the nail was removed after 24 h and every 24 h following. Protein that had passed through the nail was recovered from the cotton bud by washing twice with 500 µL of 0.1% v/v trifluoroacetic acid. Recovered protein was quantified using RP-HPLC.

Figure 9:
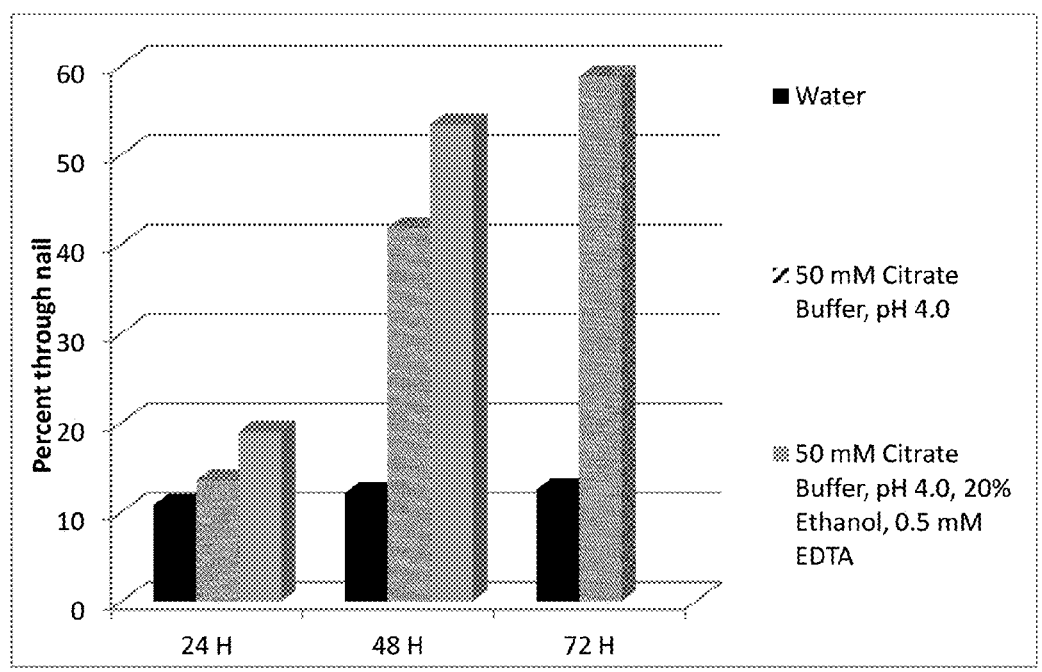
FIG. 9 is a representation of nail penetration over time by HXL008 in different formulations, water (black bars) 50 mM citrate buffer pH 4.0 (striped bars) and 50 mM citrate buffer pH 4.0, 20% v/v ethanol, 0.5 mM EDTA (grey bars)

The results of the penetration assays are represented in Table 6 and FIG. 9. When applied daily to the surface of nails, penetration of HXL008 through the nail was enhanced in the presence of 50 mM citrate buffer pH4.0, with or without ethanol and EDTA.

TABLE 6

Penetration of HXL008 in three different formulations through nails

|  |  | 24 H | 48 H | 72 H |
|---|---|---|---|---|
| Water | Dose (µg) | 100 | 100 | 100 |
|  | Amount in receptor (µg) | 10.75 | 12.1 | 12.48 |
|  | Percent of dose permeated | 10.8% | 12.1% | 12.5% |
|  | Cumulative percent permeated | 10.8% | 11.4% | 11.8% |
| 50 mM Citrate Buffer, pH 4.0 | Dose (µg) | 100 | 100 | 100 |
|  | Amount in receptor (µg) | 13.5 | 41.72 | 58.66 |
|  | Percent of dose permeated | 13.5% | 41.7% | 58.7% |
|  | Cumulative percent permeated | 13.5% | 27.6% | 38.0% |
| 50 mM Citrate Buffer, pH 4.0, 20% v/v Ethanol, 0.5 mM EDTA | Dose (µg) | 100 | 100 |  |
|  | Amount in receptor (µg) | 18.97 | 53.33 |  |
|  | Percent of dose permeated | 19.0% | 53.3% |  |
|  | Cumulative percent permeated | 19.0% | 36.2% |  |

Example 8

Recombinant Expression of Plant Defensins Using *P. Pastoris*

The plant defensins HXL008, HXL008+ala, HXL004 and NaD1 were expressed in *Pichia pastoris* as described in the Methods.

The yield for various plant defensins from recombinant expression in *P. pastoris* is shown in Table 7. HXL008+ala was the most highly expressed protein with a yield of 7.5 mg/L.

TABLE 7

Defensin yields following protein expression and purification

| Protein | Protein purified per litre of culture (mg) |
|---|---|
| HXL008 + ala | 7.5 |
| HXL008 | 6.3 |
| HXL004 | 1.2 |
| NaD1 | 3.2 |

Example 9

Large Scale Expression and Purification of HXL008+Ala

The open reading frame (ORF) for HXL008+ala is cloned into the *Pichia* expression vector pPIC9. The ORF is inserted in frame with the α-factor secretion signal and directly downstream of the KEX2 cleavage site. The plasmid is then linearized in the HIS4 selection cassette using the restriction enzyme SalI and transformed into electrocompetent GS115 *Pichia pastoris* cells. Positive colonies are selected using media lacking histidine. Positive colonies are used to inoculate 5 mL of YPD and incubated for 25 h at 30° C. in a shaking incubator. Cells in culture are mixed with 20% glycerol, flash-frozen and stored at −80° C.

Cells from a glycerol stock are streaked onto YPD plates and allowed to grow at 30° C. for 48 h. Plates are then stored at 4° C. for up to 2 weeks.

Cells from a YPD plate (pPIC9-defensin, GS115) are used to inoculate 500 mL of BMG medium (described in the Invitrogen *Pichia* Expression Manual) in a 2.5 L flask and the culture is incubated for 2 days in a 28° C. shaking incubator (120 rpm). After 48 h, the culture is used to inoculate 20 L of Fermentation Basal Salts Media in a 30 L B Braun Fermenter. Temperature is maintained at 28° C. over the period of the ferment. The pH is maintained at 5.0 over the period of the ferment by addition of 25% v/v ammonia Solution in response to any decrease in pH. Dissolved oxygen (DO) is maintained at 30% during the fermentation period by increasing the agitation (minimum 500 rpm) or increasing the flow or oxygen.

The 20 L culture fed sterile 100% v/v glycerol at a rate of 3.6 mL/min until the cell density reaches 250-300 g/L. At this time, the glycerol feed is stopped and the culture is allowed to proceed until all the glycerol is consumed, as evidenced by a spike in DO. The culture is then fed sterile 100% v/v methanol containing 12 mL/L trace metals. The feed rate is accelerated over 8 h from 0.2 to 2.18 mL/min. A feed rate of 2.18 mL/min is then continued for an additional 48 h.

The expression medium is harvested and separated from cells by centrifugation (6000 rpm, 20 min, 4° C.). The medium is clarified by filtering through a 0.22 μm membrane The medium is diluted 1 in 5 in 50 mM acetate buffer pH 5.3. Diluted medium is then applied to an SP-Sepharose column (High Performance) that has been pre-equilibrated with 50 mM acetate buffer pH 5.3. The column is then washed with 20 column volumes of 50 mM acetate buffer pH 5.3. Bound HXL008 is eluted using a linear gradient of 0-100% v/v 50 mM acetate buffer pH 5.3 containing 1 M NaCl. Fractions containing protein (as identified by absorbance at 280 nm) are pooled and concentrated down to 200 mL before being subjected to size-exclusion chromatography. Proteins are loaded onto a 1800 mL Superdex 30 column (5 cm×92 cm XK50/100 column) and eluted using 50 mM sodium phosphate buffer, 150 mM NaCl, pH 7.2 at 15 mL/min Proteins eluting in the void volume are discarded and fractions containing HXL008+ala are identified using mass spectrometry. Fractions containing HXL008 are pooled and then desalted into sterile MilliQ water and concentrated using a 3000 MWCO spin column The resulting peptide solution was analysed by SDS-PAGE, RP-HPLC and mass spectrometry. The final yield was determined by measuring the peptide concentration using a BCA assay. A total of 1.436 g of HXL008+ala is produced and purified to greater than 99% purity.

Figure 10A:
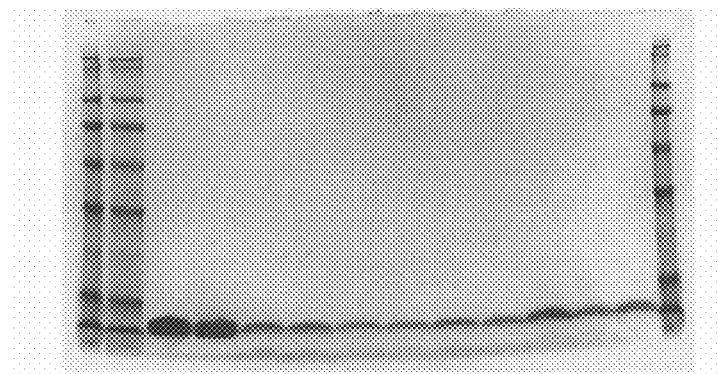
FIG. 10(A) is an SDS-PAGE gel of purified HXL008+ala. Lanes 1, 2 and 14 are molecular weight markers (SeeBlue® Plus 2). Lanes 3 and 4 are HXL008+ala standard (5 μg). Lanes 5 to 12 are samples from the pooled size exclusion fractions.
Figure 10B:
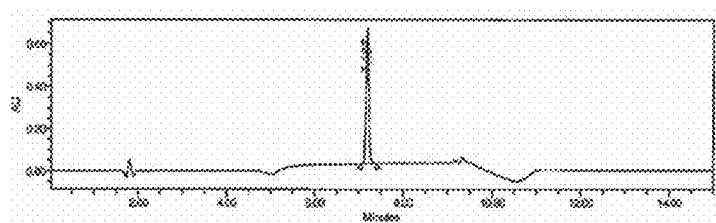
FIG. 10(B) is a RP-HPLC trace of the pooled elutions. A single peak is observed at ~7.1 mins
Figure 10C:
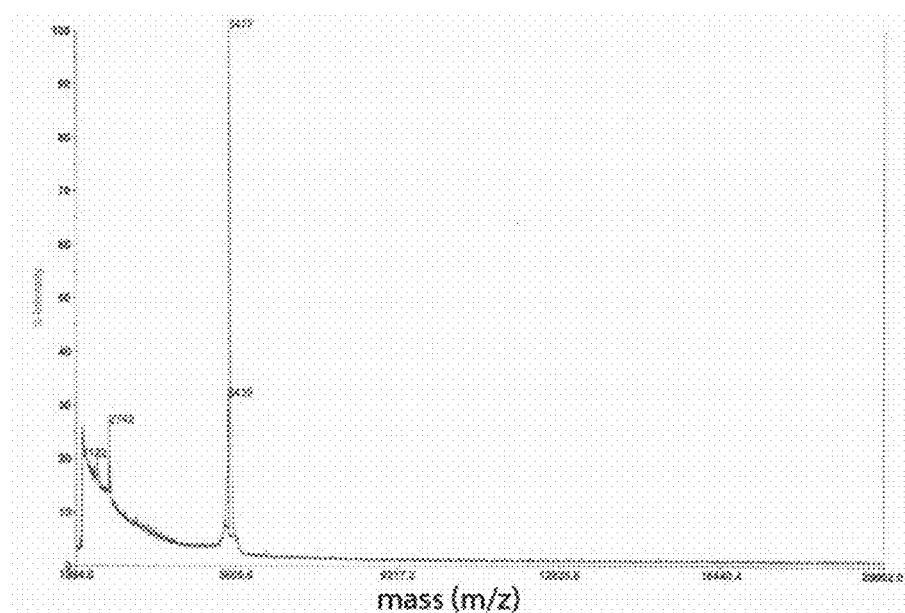
FIG. 10(C) is a MALDI-TOF mass spectrometry trace from 4 kDa to 20 kDa.

The results of the purification are shown in FIG. 10. FIG. 10A is an SDS-PAGE gel of purified HXL008+ala. Lanes 1, 2 and 14 are molecular weight markers (SeeBlue [registered trade mark] Plus 2). Lanes 3 and 4 are HXL008+ala standard (5 μg). Lanes 5 to 12 are samples from the pooled size exclusion fractions. FIG. 10B is a RP-HPLC trace of the pooled elutions. A single peak is observed at ~7.1 mins which is consistent with the expected retention time for HXL008+ala. Figure XC is a MALDI-TOF mass spectrometry trace from 4 kDa to 20 kDa. The observed mass (5477 Da) corresponds to the expected mas for HXL008+ala with all four disulphide bonds formed.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Altschul et al. (1997) *Nucl. Acids. Res.* 25:3389
Ausubel et al. (1994-1998) *In: Current Protocols in Molecular Biology*, John Wiley & Sons Inc
Bloch and Richardson (1991) *FEBS Lett* 279(1):101-104
Broekaert et al. (1990) *FEMS Microbiol Lett* 69:55-59
Cabral et al (2003) *Protein Express Purif* 31(1):115-122
Colilla et al. (1990) *FEBS Lett* 270(1-2):191-194
Elewski et al. (2012) Fungal diseases In: Bolognia, Jorizzo, Schaffer eds, *Dermatology* 3$^{rd}$ ed. Philadelphia, Pa.; Elsevier Saunders; chapter 77
Greco et al. (1995) *Pharmacol Rew* 47:331-385
Hayes et al. (2013) *Antimicrob Agents Ch* 57(8)3667-3675
Hui et al (2002) *J. Pharm Sci* 9(11): 189-195
Janssen et al. (2003) *Biochemistry* 42(27):8214-8222
Johnson et al., Peptide Turn Mimetics in Biotechnology and Pharmacy, Pezzuto et al., Eds., Chapman and Hall, New York, 1993
Kent (2002) *Genome Res* 12: 656-664
Khengar et al. (2007) *Pharm Res* 24(12):2207-2212
Kobayashi et al (2004) *Euro J Pharm Sci* 21:471-477
Langmead et al (2009) *Genome Biol* 10:R25
Li and Durbin (2010) *Bionformatics* 26:589-595
Malhotra and Zatz (2002) *J Pharm Sci* 91(2):312-323
Merten and Lippold (1997) *J Pharm Pharmacol* 49: 866-872
Murdan (2008) *Expert Opin Drug Deliv* 5(11):1267-1282
Murthy et al. (2009) *J Pharm Sci* 98(11):4264-4271
Nair et al. (2009) *J Pharm Pharmacol* 61(4):431-437
Rapini et al. (2007) *Dermatology:*2-volume set, St. Louis: Mosby
Reeves U.S. Pat. No. 6,391,879
Reid et al (2011) *Nature Review & Microbiol* 9: 27-38
Richer (1987) *Pestic Sci* 19:309-315
Sagaram et al., (2011) *PLoS One* 6.4: e18550
Sotiriou et al. (2010) *Acta Derm-Venereol* 9(2):216-217
Thevissen et al. (2012) *Mol Microbiol* 84(1):166-180
U.S. Pat. No. 6,911,577 (Pioneer Hi-Bred International, Inc. and E.I. DuPont DeNemours and Company)
U.S. Pat. No. 6,391,879 (Astan, Inc.)
van der Weerden et al. (2013) *Cell Molecule Life Sci* 70(19) 3545-3570
van der Weerden et al (2013) *Fungal Biol Rev* 26:121-131
Westerberg et al. (2013) *American Family Physician* 88(11): 762-770
Willers et al. European Patent No. 2664327

The invention claimed is:

1. A method for treating a fungal infection in a nail of a subject, said method comprising topically administering to the nail of the subject an effective amount of a synergistic combination of a plant defensin having the consensus amino acid sequence set forth in SEQ ID NO: 24 and an antifungal agent.

2. The method of claim 1 wherein the nail is a toe or finger nail.

3. The method of claim 2 wherein the infection is associated with onychomycosis.

4. The method of claim 2 wherein the infection is *tinea pedis* or fungal infection of cuticle tissue surrounding the nail.

5. The method of claim 1 wherein the subject is a human.

6. The method of claim 1 wherein the defensin is selected from the group consisting of SEQ ID NO:1, SEQ ID NO:2, SEQ ID NO:3, SEQ ID NO:25, SEQ ID NO:26 and SEQ ID NO:27.

7. The method of claim 6 wherein the defensin is defined by SEQ ID NO:1 or SEQ ID NO:25.

8. The method of claim 1 wherein the antifungal agent is a chemical fungicide selected from the group consisting of terbinafine, intraconazole, fluconazole, ciclopirox, clotrimazole, amorolfine, tavaborole, efinaconazole and butenafine.

9. The method of claim 1 wherein the fungal pathogen is a dermatophyte.

10. The method of claim 9 wherein the dermatophyte is selected from the group consisting of *Trichophyton rubrum, Trichophyton interdigitale, Trichophyton violaceum, Trichophyton tonsurans, Trichophyton soudanense, Trichophyton mentagrophytes, Microsporum fulvum, Epidermophyton floccosum* and *Microsporum gypseum*.

\* \* \* \* \*